(12) United States Patent
Raslambekov

(10) Patent No.: US 10,950,061 B1
(45) Date of Patent: Mar. 16, 2021

(54) SYSTEMS AND METHODS FOR PLANNING AN ORTHODONTIC TREATMENT

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 16/937,312

(22) Filed: Jul. 23, 2020

(51) Int. Cl.
| | |
|---|---|
| *G06T 19/20* | (2011.01) |
| *A61C 7/00* | (2006.01) |
| *G16H 50/50* | (2018.01) |
| *G16H 20/00* | (2018.01) |
| *G16H 10/60* | (2018.01) |
| *G16H 50/20* | (2018.01) |

(52) U.S. Cl.
CPC .............. *G06T 19/20* (2013.01); *A61C 7/002* (2013.01); *G16H 10/60* (2018.01); *G16H 20/00* (2018.01); *G16H 50/50* (2018.01); *A61C 2007/004* (2013.01); *G06T 2210/41* (2013.01); *G16H 50/20* (2018.01)

(58) Field of Classification Search
None
See application file for complete search history.

(56) References Cited

U.S. PATENT DOCUMENTS

| | | |
|---|---|---|
| 5,975,893 A | 11/1999 | Chishti et al. |
| 6,183,248 B1 | 2/2001 | Chishti et al. |
| 6,227,850 B1 | 5/2001 | Chishti et al. |
| 6,309,215 B1 | 10/2001 | Phan et al. |
| 6,318,994 B1 | 11/2001 | Chishti et al. |

(Continued)

FOREIGN PATENT DOCUMENTS

| | | |
|---|---|---|
| WO | 1998058596 A1 | 12/1998 |
| WO | 2000019928 A3 | 4/2000 |

(Continued)

OTHER PUBLICATIONS

Jin et al, 'A comparison of algorithms for vertex normal computation', The Visual Computer, vol. 21, pp. 71-82. (Year: 2005).*

(Continued)

*Primary Examiner* — Patrick F Valdez
(74) *Attorney, Agent, or Firm* — BCF LLP

(57) ABSTRACT

A method and a system for determining an orthodontic treatment for a subject are provided. The method comprises: acquiring a raw 3D representation of an arch form of the subject comprising a 3D mesh having a plurality of vertices further comprising: constrained vertices associated with a defined portion; unconstrained vertices initially associated with an undefined portion; generating a set of confirmed constrained vertices, including the constrained vertices, for providing the augmented 3D representation of the given tooth by: iteratively, for a given constrained vertex, identifying at least one associated unconstrained vertex which is adjacent to the given constrained vertex in the 3D mesh, and based on an angular difference between associated normal vectors, identifying the at least one associated unconstrained vertex either to be a constrained vertex or an unconstrained vertex; causing display of the augmented 3D representation of the given tooth based on the set of confirmed constrained vertices.

19 Claims, 26 Drawing Sheets

(56) References Cited

U.S. PATENT DOCUMENTS

| | | |
|---|---|---|
| 6,334,853 B1 | 1/2002 | Kopelman et al. |
| 6,386,878 B1 | 5/2002 | Pavlovskaia et al. |
| 6,398,548 B1 | 6/2002 | Chrishti et al. |
| 6,463,344 B1 | 10/2002 | Pavloskaia et al. |
| 6,471,511 B1 | 10/2002 | Chishti et al. |
| 6,554,611 B2 | 4/2003 | Chishti et al. |
| 6,602,070 B2 | 8/2003 | Miller et al. |
| 6,665,570 B2 | 12/2003 | Pavloskaia et al. |
| 6,685,470 B2 | 2/2004 | Chishti et al. |
| 6,688,886 B2 | 2/2004 | Hughes et al. |
| 6,705,863 B2 | 3/2004 | Phan et al. |
| 6,726,478 B1 | 4/2004 | Isiderio et al. |
| 6,739,870 B2 | 5/2004 | Lai et al. |
| 6,767,208 B2 | 7/2004 | Kaza |
| 6,979,196 B2 | 12/2005 | Nikolskiy et al. |
| 7,027,642 B2 | 4/2006 | Rubbert et al. |
| 7,040,896 B2 | 5/2006 | Pavlovskaia et al. |
| 7,059,850 B1 | 6/2006 | Phan et al. |
| 7,063,532 B1 | 6/2006 | Jones et al. |
| 7,123,767 B2 | 10/2006 | Jones et al. |
| 7,125,248 B2 | 10/2006 | Phan et al. |
| 7,134,874 B2 | 11/2006 | Chishti et al. |
| 7,220,122 B2 | 5/2007 | Chishti |
| 7,241,142 B2 | 7/2007 | Abolfathi et al. |
| 7,293,988 B2 | 11/2007 | Wen |
| 7,320,592 B2 | 1/2008 | Chishti et al. |
| 7,373,286 B2 | 5/2008 | Nikolskiy et al. |
| 7,377,778 B2 | 5/2008 | Chishti et al. |
| 7,428,481 B2 | 9/2008 | Nikolskiy et al. |
| 7,442,040 B2 | 10/2008 | Kuo |
| 7,637,740 B2 | 12/2009 | Knopp |
| 7,689,398 B2 | 3/2010 | Cheng et al. |
| 7,740,476 B2 | 6/2010 | Rubbert et al. |
| 7,771,195 B2 | 8/2010 | Knopp et al. |
| 7,826,646 B2 | 11/2010 | Pavlovskaia et al. |
| 7,841,858 B2 | 11/2010 | Knopp et al. |
| 7,844,429 B2 | 11/2010 | Matov et al. |
| 7,865,259 B2 | 1/2011 | Kuo et al. |
| 7,904,307 B2 | 3/2011 | Abolfathi et al. |
| 7,905,725 B2 | 3/2011 | Chishti et al. |
| 7,942,672 B2 | 5/2011 | Kuo |
| 7,993,134 B2 | 8/2011 | Wen |
| 8,038,444 B2 | 10/2011 | Kitching et al. |
| 8,044,954 B2 | 10/2011 | Kitching et al. |
| 8,108,189 B2 | 1/2012 | Chelnokov et al. |
| 8,131,393 B2 | 3/2012 | Matov et al. |
| 8,135,569 B2 | 3/2012 | Matov et al. |
| 8,244,390 B2 | 8/2012 | Kuo et al. |
| 8,439,672 B2 | 5/2013 | Matov et al. |
| 8,465,280 B2 | 6/2013 | Sachdeva et al. |
| 8,478,435 B2 | 7/2013 | Kuo et al. |
| 8,639,477 B2 | 1/2014 | Chelnokov et al. |
| 8,641,414 B2 | 2/2014 | Borovinskih et al. |
| 8,734,150 B2 | 5/2014 | Wen |
| 8,780,106 B2 | 7/2014 | Chishti et al. |
| 8,807,999 B2 | 8/2014 | Kuo et al. |
| 8,896,592 B2 | 11/2014 | Boltunov et al. |
| 8,897,902 B2 | 11/2014 | See et al. |
| 8,961,173 B2 | 2/2015 | Miller |
| 9,060,829 B2 | 6/2015 | Sterental et al. |
| 9,107,722 B2 | 8/2015 | Matov et al. |
| 9,161,823 B2 | 10/2015 | Morton et al. |
| 9,211,166 B2 | 12/2015 | Kuo et al. |
| 9,326,831 B2 | 5/2016 | Cheang |
| 9,345,557 B2 | 5/2016 | Anderson et al. |
| 9,375,293 B2 | 6/2016 | Taub et al. |
| 9,375,300 B2 | 6/2016 | Matov et al. |
| 9,414,897 B2 | 8/2016 | Wu et al. |
| 9,433,476 B2 | 9/2016 | Khardekar et al. |
| 9,529,970 B2 | 12/2016 | Andreiko |
| 9,592,103 B2 | 3/2017 | Taub et al. |
| 9,610,140 B2 | 4/2017 | Anderson et al. |
| 9,622,834 B2 | 4/2017 | Chapoulaud et al. |
| 9,792,413 B2 | 10/2017 | Badawi |
| 9,844,424 B2 | 12/2017 | Wu et al. |
| 10,011,050 B2 | 7/2018 | Kitching et al. |
| 10,076,389 B2 | 9/2018 | Wu et al. |
| 10,307,222 B2 | 6/2019 | Morton et al. |
| 10,332,164 B2 | 6/2019 | Abolfathi et al. |
| 10,335,251 B2 | 7/2019 | See et al. |
| 10,383,704 B2 | 8/2019 | Kitching |
| 10,405,947 B1 | 9/2019 | Kaza et al. |
| 10,405,951 B1 | 9/2019 | Kopelman et al. |
| 10,413,385 B2 | 9/2019 | Sherwood et al. |
| 10,433,934 B2 | 10/2019 | Kopelman |
| 10,463,452 B2 | 11/2019 | Matov et al. |
| 10,470,846 B2 | 11/2019 | Kopelman et al. |
| 10,524,880 B2 | 1/2020 | Wen |
| 10,553,309 B2 | 2/2020 | Trosien et al. |
| 10,561,476 B2 | 2/2020 | Matov et al. |
| 10,595,965 B2 | 3/2020 | Khardekar et al. |
| 10,617,489 B2 | 4/2020 | Grove et al. |
| 10,650,517 B2 | 5/2020 | Parpara et al. |
| 10,653,503 B2 | 5/2020 | Boltunov et al. |
| 10,783,629 B2 | 9/2020 | Parpara et al. |
| 10,792,127 B2 | 10/2020 | Kopelman et al. |
| 10,813,721 B2 | 10/2020 | Sterental et al. |
| 2005/0019732 A1* | 1/2005 | Kaufmann .......... G06T 7/12 433/213 |
| 2005/0089213 A1 | 4/2005 | Geng et al. |
| 2005/0244791 A1 | 11/2005 | Davis et al. |
| 2013/0095446 A1 | 4/2013 | Andreiko et al. |
| 2014/0288894 A1 | 9/2014 | Chishti et al. |
| 2016/0302885 A1 | 10/2016 | Matov et al. |
| 2017/0035536 A1 | 2/2017 | Alvarez Garcia et al. |
| 2017/0079748 A1 | 3/2017 | Andreiko |
| 2017/0367789 A1* | 12/2017 | Fujiwara .......... G16H 50/50 |
| 2018/0039755 A1 | 2/2018 | Matov et al. |
| 2018/0165818 A1 | 6/2018 | Tsai et al. |
| 2018/0304497 A1 | 10/2018 | Kitching et al. |
| 2019/0000592 A1 | 1/2019 | Cam et al. |
| 2019/0046295 A1 | 2/2019 | Morton et al. |
| 2019/0282333 A1 | 9/2019 | Matov et al. |
| 2019/0314117 A1 | 10/2019 | Morton et al. |
| 2019/0357997 A1 | 11/2019 | Shi et al. |
| 2020/0000551 A1 | 1/2020 | Li |
| 2020/0000552 A1 | 1/2020 | Mednikov et al. |
| 2020/0146776 A1 | 5/2020 | Matov et al. |
| 2020/0229900 A1 | 7/2020 | Cunliffe et al. |
| 2020/0297459 A1 | 9/2020 | Grove et al. |
| 2020/0306012 A1 | 10/2020 | Roschin et al. |

FOREIGN PATENT DOCUMENTS

| | | |
|---|---|---|
| WO | 2000019930 A1 | 4/2000 |
| WO | 2000019931 A1 | 4/2000 |
| WO | 2000069356 A1 | 11/2000 |
| WO | 2000069357 A1 | 11/2000 |
| WO | 2001074268 A2 | 10/2001 |
| WO | 2018085718 A2 | 5/2018 |
| WO | 2019089989 A3 | 6/2019 |

OTHER PUBLICATIONS

Kumar et al, 'Computer-Aided Design & Applications', 8(2), pp. 211-224. (Year: 2011).*

Sheng-hui, "Automatic Tooth Segmentation of Dental Mesh Based on Harmonic Fields", Biomed Res Intv.2015; 2015PMC4564592 | 10 pages | https://doi.org/10.1155/2015/187173.

Zhongyi Li, "Interactive Tooth Separation from Dental Model Using Segmentation Field", PLoS One. 2016; 11(8): e0161159, Published online Aug. 17, 2016. doi: 10.1371/journal.pone.0161159.

* cited by examiner

SYSTEMS AND METHODS FOR PLANNING AN ORTHODONTIC TREATMENT

The present technology relates to systems and methods for planning an orthodontic treatment for a patient, in general; and more specifically, to systems and methods for reconstructing crowns of teeth of the patient.

BACKGROUND

Orthodontic treatment plans for treating malocclusion disorders of a subject (or for assessing efficacy of an already ongoing one), typically use various anthropometric parameters associated with a subject's skull, such as those associated with a subject's teeth (including crown portions and root portions thereof), and a subject's gingiva. Such parameters may be, for example, obtained or otherwise, determined through analyzing corresponding image data.

For example, by applying intra-oral scanning techniques, 3D models of the crown portions of the subject's teeth may be obtained, and some of the anthropometric parameters associated therewith may be used for devising an orthodontic treatment. Broadly speaking, these parameters, for a given tooth, may include, for example, overall dimensions of a crown portion thereof, a number of cusps, and certain other anatomical features associated therewith, such as data indicative of lobes, developmental grooves, a marginal ridge, and the like. When planning the orthodontic treatment, such parameters may be used, for example, to determine a center of resistance (CR) point associated with the given tooth, which may further enable to model movements of the crown portion of the given tooth relative to crown portions of other of the subject's teeth to avoid collisions therewith, as an example. In another aspect, the parameters associated with the crown portion and determined, based on a 3D model thereof, may be used for generating a 3D model of the given tooth that may further be used for a more detailed analysis of tooth movements of the given tooth in the course of the orthodontic treatment.

However, the intra-oral scanning techniques may have specific drawbacks that may not allow generating an accurate 3D model of the crown portion. For example, an intra-oral scanner may be incapable of receiving all amount of light reflected off the crown portion while capturing an image thereof. This may result in generating, in the 3D model of the crown portion, certain image artefacts (also referred to herein as "digital garbage" or "undesired portions" of the 3D model), that is, portions of the 3D model of the crown portion forming no part of the actual configuration of the crown portion of the given tooth nor of other anatomical structures of the subjects, such as the subject's gingiva. For example, these image artefacts may typically be found in portions of the 3D model of the crown portions associated with interdental spaces.

The 3D model including such image artefacts may thus be referred to as a "raw 3D model" of the crown portion as inaccurately representing the crown portion of the given tooth. Consequently, the raw 3D model of the crown portion may not provide reliable input data for determining the orthodontic treatment for the subject as the parameters associated with the crown portion determined based thereon, as well as the 3D model of the given tooth generated based thereon may hence be considerably skewed. This may affect predictability and efficacy of the planned orthodontic treatment.

Certain prior art approaches have been proposed to tackle the above-identified technical problem, which are directed to automatic segmentation of 3D models of crown portions from a 3D model of a subject's arch form.

United States Patent Application Publication No.: 2005/0089213-A1 filed on Oct. 25, 2004, assigned to Technest Holdings Inc., and entitled "Method and Apparatus for Three-Dimensional Modeling via an Image Mosaic System" discloses an imaging method and system for 3D modeling of a 3D surface forms a mosaic from multiple uncalibrated 3D images, without relying on camera position data to merge the 3D images. The system forms the 3D model by merging two 3D images to form a mosaiced image, merging the mosaiced image with another 3D image, and repeating the merging process with new 3D images one by one until the 3D model is complete. The images are aligned in a common coordinate system via spatial transformation.

U.S. Pat. No. 10,335,251-B2 issued on Jul. 2, 2019, assigned to 3M Innovative Properties Co, and entitled "Orthodontic Digital Setups" discloses Methods for recognizing a virtual tooth surface, defining a virtual tooth coordinate system, and simulating a collision between virtual teeth. Methods include receiving input data specifying a point on the rendered surface model associated with a tooth, deriving a perimeter on the surface model of the tooth based on the input data, and analyzing the surface model along a plurality of paths outwardly extending from points on the perimeter along the three-dimensional surface to produce gingival margin data. Methods also include receiving point input data that defines a point on the virtual tooth, receiving axis input data that defines first and second axes associated with the virtual tooth, computing a substantially normal vector for a portion of the tooth surface surrounding the point, and computing a coordinate system based on the axis input and the computed vector. Methods also include receiving permissible movement input data directed to permissible movement of a first virtual tooth, simulating, in three dimensional space, bringing the first virtual tooth into contact with a second virtual tooth while constraining movement of the first virtual tooth based on the permissible movement input data, and displaying data resulting from the simulation.

U.S. Pat. No. 7,740,476-B2 issued on Jun. 22, 2010, assigned to Orametrix Inc., and entitled "Method and Workstation for Generating Virtual Tooth Models from Three-Dimensional Tooth Data" discloses a method for taking a three-dimensional virtual model of the dentition and associated anatomical structures of a patient and isolating individual teeth from the rest of the anatomical structure, e.g. gums, to thereby produce individual, virtual three-dimensional tooth objects. The individual tooth objects can be displayed on the display of an orthodontic workstation and moved independently from each other, and thereby form the basis of planning treatment for the patient. The individual, virtual three-dimensional tooth objects are created by comparing the virtual model of the dentition to virtual, three-dimensional template teeth that are stored in memory in a process described in detail herein. The template teeth can include roots as well as crowns. The template teeth can be stored objects acquired from some external source or alternatively developed from a database of patient scans. Virtual three-dimensional brackets are also stored in the memory of the workstation. The virtual brackets can be placed on the virtual teeth and moved relative to the teeth as needed in a preliminary step in treatment planning.

U.S. Pat. No. 7,027,642-B2 issued on Apr. 11, 2006, assigned to Orametrix Inc., and entitled "Methods for Registration of Three-Dimensional Frames to Create Three-Dimensional Virtual Models of Objects" discloses a method and system for constructing a virtual three-dimensional model of an object using a data processing system, and at least one machine-readable memory accessible to the data processing system. A set of at least two digital three-dimensional frames of portions of the object are obtained from a scanner or other source comprising a set of point coordinates in a three dimensional coordinate system providing differing information of the surface of the object. The frames provide a substantial overlap of the represented portions of the surface of the object, but do not coincide exactly. Data representing the set of frames are stored in the memory and processed by the data processing system so as to register the frames relative to each other to thereby produce a three-dimensional virtual representation of the portion of the surface of the object covered by the set of frames.

SUMMARY

It is an object of the present technology to ameliorate at least some of the inconveniences present in the prior art.

Developers of the present technology have devised methods and systems directed to automatic segmentation of raw 3D models from each other, and further smoothing surfaces thereof, thereby restoring a more accurate contour of each of the crown portions within a respective augmented 3D model thereof.

More specifically, the developers have appreciated that, within the raw 3D model of the crown portion, there may be identified a portion accurately representative of the crown portion—a so called "defined portion"—and at least one portion that may not be definitively identified as either forming part of the image artefacts or the crown portion—a so called "undefined portion". Further, the developers have realized that as the raw 3D model of the crown portion may be represented as a 3D mesh comprising a plurality of mesh elements (such as tringle mesh elements), an angular difference between normal vectors of two adjacent mesh elements, wherein a first mesh element is from the defined portion and a second mesh element is from the undefined portion, may be a metric of local smoothness within the raw 3D model of the crown portion. Thus, based on comparison of the angular difference with a predetermined threshold value, determination can be made as to whether the second mesh element should be included in an augmented 3D model of the crown portion of the given tooth, or should be identified as forming part of the image artefacts and thus be rejected.

By so doing, the methods and systems described herein can be said to be directed to "propagating" smoothness of the defined portion to the undefined portion. Therefore, the augmented 3D model of the crown portion free of the image artefacts may be representative of a more anatomically accurate contour thereof, which may hence allow for a more accurate modelling of movements of the crown portion of the given tooth within the subject's arch form, for example avoiding collisions thereof with other crown portions. Also, the so generated augmented 3D model of the crown portion may further allow generating a more accurate 3D model of the root portion, higher accuracy of which may enable to model the movements of the given tooth as a whole more predictably in the course of the orthodontic treatment.

Further, the developers have realized that for a more efficient and effective orthodontic treatment, it may be necessary to consider the subject's teeth in their entirety, that is, to determine certain other parameters associated with the root portions and that of the subject's gingiva as well.

However, the intra-oral scanning techniques cannot be used to obtain the image data representative of the root portion. Further, the intra-oral scanning techniques may not provide an accurate 3D model of the subject's gingiva as they can be limited to portions thereof accessible to the intra-oral scanner. Therefore, obtaining such image data requires the use of other imaging techniques such as computer tomography (CT), magnetic resonance (MR) imaging, or panoramic radiography, for example.

However, these techniques and the associated apparatus may not be readily available to the practitioners to obtain such data. Further, even if timely access to the additional image data is available, it could be computationally expensive to merge it with the augmented 3D model of the crown portion of the given tooth maintaining certain level of quality of the resulting orthodontic treatment, which may significantly reduce efficiency of such an approach.

Thus, the developers of the present technology have further devised methods and systems directed to (1) reconstructing the 3D model of the root portion of the given tooth, thereby reconstructing the 3D model of the given tooth, and (2) reconstructing an augmented 3D model of the subject's gingiva.

To that end, the developers have realized that the 3D model of the root portion may be a parametric equivalent model thereof, which may be indicative of certain specific parameters of the actual root portion of the given tooth currently needed to determine the orthodontic treatment. Further, the 3D model of the given tooth may further be generated by merging the parametric equivalent model of the root portion and the augmented 3D model of the crown portion of the given tooth. Accordingly, the so-generated 3D model of the given tooth may further be used, for example, for determining a force system to be imposed on the given tooth to cause it to move into a position associated with alignment thereof within a subject's arch form.

Thus, the 3D model of the given tooth may be used for modelling so determined movements of the given tooth in the course of the entire orthodontic treatment, and for accounting for interactions of the given tooth with other teeth adjacent thereto more comprehensively.

Further, the reconstructing the augmented 3D model of the subject's gingiva may be based on a raw 3D model thereof and so reconstructed 3D models of the crown portions, and may include restoring certain portions of the subject's gingiva that were not accessible to the imaging device at the moment of generating the raw 3D model. For example, access to these portions may be obstructed by other anatomical structures of the subject's skull, such as muscles, bones, and junctions, which may not allow for the raw 3D model of the subject's gingiva to be representative of actual overall dimensions thereof. As a result, modelling the movements of the subject's teeth, based on such a raw 3D model of the subject's gingiva, inaccurately representative thereof, may, for example, be associated with causing discomfort to the subject, or even damages to the subject's gingiva (including tissues around it, such as proximal blood vessels and nerve pathways, for example) during receiving the orthodontic treatment. Furthermore, using the raw 3D model of the subject's gingiva for producing aligners may result in low quality thereof.

Therefore, the 3D model of the subject's gingiva accurately representing an actual anatomical configuration thereof may allow for determining a safer and more effective orthodontic treatment for the subject.

Non-limiting embodiments of the present technology are directed to methods and systems for generating a comprehensive 3D model of the subject's arch form including (i) generating the augmented 3D model of the crown portion of the given tooth, based on the raw 3D model thereof, (ii) generating the parametric equivalent model for the root portion of the given tooth based on the augmented 3D model of the crown portion thereof and certain reference data associated therewith, and (iii) generating the augmented 3D model of the subject's gingiva based on the raw 3D model thereof. These methods and systems allow generating the comprehensive 3D model of the subject's arch form avoiding the need for obtaining the additional image data, for example, that representative of the root portion of the given tooth and hidden portions of the subject's gingiva, such as CT/MR scans or a panoramic radiograph, for example.

Therefore, such an approach to reconstructing the comprehensive 3D model of the subject's arch form allows manipulating the level of granularity and detail of the so reconstructed model depending on a specific task at hand associated with the orthodontic treatment determination process using a minimum of image data, which eventually allows for a more effective and efficient use of computational resources.

Therefore, according to a first broad aspect of the present technology, there is provided a method for providing an augmented 3D representation of a given tooth of a patient. The method is executable by a processor. The method comprises: acquiring a raw 3D representation of an arch form of the patient, the arch form comprising a gingiva and at least one tooth of the patient, the raw 3D representation comprising a defined portion forming part of a surface of the given tooth, and at least one undefined portion not forming part of the surface of the given tooth; the raw 3D representation comprising a 3D mesh having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector; generating a set of confirmed constrained vertices, including the constrained vertices associated with the defined portion, for providing the augmented 3D representation of the given tooth by: iteratively, for a given constrained vertex, identifying at least one associated unconstrained vertex which is adjacent to the given constrained vertex in the 3D mesh; determining an angular difference between the normal constrained vertex vector of the given constrained vertex and the normal unconstrained vertex vector of the at least one associated unconstrained vertex; in response to the angular difference being equal to or below a predetermined threshold value: identifying the at least one associated unconstrained vertex to be a constrained vertex associated with the defined portion for inclusion in the set of confirmed constrained vertices; in response to the angular difference being above the predetermined threshold value: identifying the at least one associated unconstrained vertex to be an unconstrained vertex associated with the undefined portion for exclusion from the set of confirmed constrained vertices; causing display of the augmented 3D representation of the given tooth based on the set of confirmed constrained vertices.

In some implementations of the method, the causing display of the augmented 3D representation comprises: performing a smoothing operation on the set of confirmed constrained vertices to generate a smooth surface of the given tooth.

In some implementations of the method, the method comprises: causing a filling of any gaps in the set of confirmed constrained vertices by the smoothing operation.

In some implementations of the method, the performing the smoothing operation comprises applying a Harmonic Function.

In some implementations of the method, the defined portion and the undefined portion are determined by applying an erosion function to the raw 3D representation.

In some implementations of the method, the defined portion is determined by: determining, based on the erosion function, an edge of the given tooth based on the raw 3D representation of the given tooth; and determining, based on the erosion function, a location of the defined portion by a predetermined distance, along a horizontal axis associated with the raw 3D representation of the given tooth, from at least one vertical edge of the raw 3D representation of the given tooth.

In some implementations of the method, the raw 3D representation is of a plurality of teeth of the patient including the given tooth, the method further comprising segmenting the raw 3D representation to separate the representation of the given tooth from other teeth of the plurality of teeth.

In some implementations of the method, the method further comprises providing a respective augmented 3D representation for other teeth of the plurality of teeth of the patient.

In some implementations of the method, the method further comprises generating an orthodontic treatment plan based on the augmented 3D representation of the given tooth.

In some implementations of the method, the raw 3D representation of the given tooth of the patient has a crown portion and a root portion, and the defined portion is based on one or more of the crown portion and the root portion.

According to a second broad aspect of the present technology, there is provided a system for providing an augmented 3D representation of a given tooth of a patient. The system comprises a processor configured to execute a method. The method comprises: acquiring a raw 3D representation of an arch form of the patient, the arch form comprising a gingiva and at least one tooth of the patient, the raw 3D representation comprising a defined portion forming part of a surface of the given tooth, and at least one undefined portion not forming part of the surface of the given tooth; the raw 3D representation comprising a 3D mesh having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector; generating a set of confirmed constrained vertices, including the constrained vertices associated with the defined portion, for providing the augmented 3D representation of the given tooth by: iteratively, for a given constrained vertex, identifying at least one associated unconstrained vertex which is adjacent to the given constrained vertex in the 3D mesh; determining an angular difference between the normal constrained vertex vector of the given constrained vertex and the normal unconstrained vertex vector of the at least one associated unconstrained vertex; in response to the angular difference being equal to or below a predetermined threshold value: identifying the at least one associated unconstrained vertex to be a constrained vertex associated with the defined portion for inclusion in the set of confirmed constrained vertices; in response to the angular difference being above the predetermined threshold value: identifying the at least one associated unconstrained vertex to be an unconstrained vertex associated with the undefined portion for exclusion from the set of confirmed constrained vertices; causing display of the augmented 3D representation of the given tooth based on the set of confirmed constrained vertices.

In some implementations of the system, the causing display of the augmented 3D representation comprises: performing a smoothing operation on the set of confirmed constrained vertices to generate a smooth surface of the given tooth.

In some implementations of the system, the method further comprises: causing a filling of any gaps in the set of confirmed constrained vertices by the smoothing operation.

In some implementations of the system, wherein the performing the smoothing operation comprises applying a Harmonic Function.

In some implementations of the system, the defined portion and the undefined portion are determined by applying an erosion function to the raw 3D representation.

In some implementations of the system, the defined portion is determined by: determining, based on the erosion function, an edge of the given tooth based on the raw 3D representation of the given tooth; and determining, based on the erosion function, a location of the defined portion by a predetermined distance, along a horizontal axis associated with the raw 3D representation of the given tooth, from at least one vertical edge of the raw 3D representation of the given tooth.

In some implementations of the system, the raw 3D representation is of a plurality of teeth of the patient including the given tooth, the method further comprising segmenting the raw 3D representation to separate the representation of the given tooth from other teeth of the plurality of teeth.

In some implementations of the system, the processor is further configured to provide a respective augmented 3D representation for other teeth of the plurality of teeth of the patient.

In some implementations of the system, the processor is further configured to generate an orthodontic treatment plan based on the augmented 3D representation of the given tooth.

According to a third broad aspect of the present technology, there is provided a method for determining an orthodontic treatment based on generating a 3D representation of a given tooth of a subject. The given tooth includes a crown portion and a root portion. The method is executable by a processor. The method comprises: acquiring a 3D representation of the crown portion of the given tooth, the 3D representation of the crown portion being associated with a predetermined longitudinal tooth axis; generating a 3D representation of the root portion of the given tooth by executing the steps of: determining a location of a root apex of the 3D representation of the root portion relative to the predetermined longitudinal tooth axis, the determining being based on a predetermined instruction for locating the root apex; generating, in a reference plane dissecting the predetermined longitudinal tooth axis and based on the 3D representation of the crown portion, a closed curve on the 3D representation of the crown portion, segmenting the closed curve into a plurality of sub-curves; for each one of the plurality of sub-curves, based on the root apex and the predetermined longitudinal tooth axis, generating a respective segment of a plurality of segments of the 3D representation of the root portion, the plurality of segments of the 3D representation of the root portion comprising a totality thereof; merging the 3D representation of the crown portion with the 3D representation of the root portion, thereby generating the 3D representation of the given tooth; and determining, based on the 3D representation of the given tooth, the orthodontic treatment for the subject.

In some implementations of the method, the predetermined longitudinal tooth axis is a central tooth axis of the given tooth having been predetermined based on the 3D representation of the crown portion.

In some implementations of the method, the predetermined instruction for locating the root apex is based on reference data associated with the given tooth, the reference data comprising data of an approximate root length associated with the given tooth.

In some implementations of the method, the 3D representation of the crown portion comprises a 3D mesh having a plurality of vertices, and the generating, in the reference plane, the closed curve further comprising: projecting each of the plurality of vertices into the reference plane, thereby generating a plurality of projected vertices; and generating the closed curve on and around the 3D representation of the crown portion to include most distant ones of the plurality of projected vertices from the predetermined longitudinal tooth axis.

In some implementations of the method, the reference plane is perpendicular to the predetermined longitudinal tooth axis.

In some implementations of the method, the reference plane is positioned along the predetermined longitudinal tooth axis at a predetermined distance based on a height of the 3D representation of the crown portion.

In some implementations of the method, each one of the plurality of sub-curves is of a same length.

In some implementations of the method, the generating the respective segment of the 3D representation of the root portion is based on a respective Bezier curve extending between one of edges associated with the respective one of the plurality of sub-curves and the root apex.

In some implementations of the method, the respective segment of the 3D representation of the root portion is a segment of a revolution surface generated by revolving the respective Bezier curve about the predetermined longitudinal tooth axis.

In some implementations of the method, the method comprises augmenting the 3D representation of the root portion based on a respective parametric root model associated with the given tooth; and causing display of the 3D representation of the given tooth.

In some implementations of the method, the given tooth is one of a plurality of teeth of the subject, and the method further comprises: generating a respective 3D representation of each of the plurality of teeth of the subject to be included in a 3D representation of a subject's arch form; and executing a collision prevention algorithm for preventing intersection of the 3D representation of the given tooth with a 3D representation of an adjacent thereto one of the plurality of teeth within the 3D representation of the subject's arch form.

According to a fourth broad aspect of the present technology, there is provided a system for determining an orthodontic treatment based on generating a 3D representation of a given tooth of a subject. The given tooth includes a crown portion and a root portion. The system comprises a processor configured to execute a method comprising: acquiring a 3D representation of the crown portion of the given tooth, the 3D representation of the crown portion being associated with a predetermined longitudinal tooth axis; generating a 3D representation of the root portion of the given tooth by executing the steps of: determining a location of a root apex of the 3D representation of the root portion relative to the predetermined longitudinal tooth axis, the determining being based on a predetermined instruction for locating the root apex; generating, in a reference plane dissecting the tooth axis and based on the 3D representation of the crown portion, a closed curve on or around the 3D representation of the crown portion, segmenting the closed curve into a plurality of sub-curves; for each one of the plurality of sub-curves, based on the root apex and the predetermined longitudinal tooth axis, generating a respective segment of a plurality of segments of the 3D representation of the root portion, the plurality of segments of the 3D representation of the root portion comprising a totality thereof; merging the 3D representation of the crown portion with the 3D representation of the root portion, thereby generating the 3D representation of the given tooth; and determining, based on the 3D representation of the given tooth, the orthodontic treatment for the subject.

In some implementations of the system, the predetermined longitudinal tooth axis is a central tooth axis of the given tooth having been predetermined based on the 3D representation of the crown portion.

In some implementations of the system, the predetermined instruction for locating the root apex is based on reference data associated with the given tooth, the reference data comprising data of an approximate root length associated with the given tooth.

In some implementations of the system, wherein the 3D representation of the crown portion comprises a 3D mesh having a plurality of vertices, and the generating, in the reference plane, the closed curve further comprising: projecting each of the plurality of vertices into the reference plane, thereby generating a plurality of projected vertices; and generating the closed curve on and around the 3D representation of the crown portion to include most distant, from the predetermined longitudinal tooth axis, ones of the plurality of projected vertices.

In some implementations of the system, the reference plane is perpendicular to the predetermined longitudinal tooth axis; and the reference plane is further translated along the predetermined longitudinal tooth axis at a predetermined distance determined based on a height of the 3D representation of the crown portion.

In some implementations of the system, each one of the plurality of sub-curves is of a same length.

In some implementations of the system, the generating the respective segment of the 3D representation of the root portion is based on a respective Bezier curve extending between one of edges associated with the respective one of then plurality of sub-curves and the root apex; and the respective segment of the 3D representation of the root portion is a segment of a revolution surface generated by revolving the respective Bezier curve about the predetermined longitudinal tooth axis.

In some implementations of the system, the processor is further configured to: augment the 3D representation of the root portion based on a respective parametric root model associated with the given tooth; and cause display of the 3D representation of the given tooth.

In some implementations of the system, the given tooth is one of a plurality of teeth of the subject, and the processor being further configured: generate a respective 3D representation of each of the plurality of teeth of the subject to be included in a 3D representation of a subject's arch form; and execute a collision prevention algorithm for preventing intersection of the 3D representation of the given tooth with a 3D representation of an adjacent thereto one of the plurality of teeth within the 3D representation of the subject's arch form.

According to a fifth broad aspect of the present technology, there is provided a method for reconstructing a 3D representation of a gingiva associated with an arch form of a subject. The method is executed by a processor. The method comprises: acquiring a 3D representation of an arch form associated with the subject, the 3D representation including a representation of the gingiva and a plurality of teeth of the subject; the 3D representation of the arch form including data of a transverse plane associated with a skull of the subject; the transverse plane being associated with a common median axis lying therein and a common vertical axis perpendicular thereto; segmenting, in the 3D representation of the arch form, associated representations of the plurality of teeth and the gingiva to generate a plurality of segmentation loops, each segmentation loop being respectively associated with each tooth of the plurality of teeth and representing an interface of a given tooth with the gingiva; determining, between each adjacent two segmentation loops of the plurality of segmentation loops, a midpoint, thereby generating a plurality of primary midpoints for the plurality of segmentation loops; based on the plurality of midpoints, generating a primary central curve. Thus, the primary central curve may be bisected by the common median axis. The method further comprises: generating, based on the primary central curve, a first inner mesh curve and a first outer mesh curve, the first inner mesh curve positioned along a first horizontal plane and the first outer mesh curve positioned along a second horizontal plane, both the first horizontal plane and the second horizontal plane being parallel to the transverse plane and being vertically offset, along the common vertical axis, from a highest vertex of the plurality of segmentation loops; the first inner mesh curve being offset along the common median axis posteriorly relative to the primary central curve along the first horizontal plane; and the first outer mesh curve being offset along the common median axis anteriorly relative to the primary central curve along the second horizontal plane; projecting the plurality of primary midpoints onto the first inner mesh curve and the first outer mesh curve, thereby generating a first plurality of inner midpoints and a first plurality of outer midpoints; generating a first segment of the reconstructed 3D representation of the gingiva by joining each one from the plurality of primary midpoints with respective ones from the first plurality of inner midpoints and from the first plurality of outer midpoints; and causing display of the first segment of the reconstructed 3D representation of the gingiva.

In some implementations of the method, the first horizontal plane and the second horizontal plane comprise a same horizontal plane.

In some implementations of the method, the first horizontal plane and the second horizontal plane are vertically offset, along the common vertical axis, relative to each other.

In some implementations of the method, the projecting the plurality of primary midpoints onto the first inner mesh curve and the first outer mesh curve is based on respective proportional coefficients, a given one of the respective proportional coefficients being indicative of a ratio between a length of the primary central curve and that of a respective one of the first inner mesh curve and the first outer mesh curve.

In some implementations of the method, the method further comprises generating a second segment of the reconstructed 3D representation of the gingiva by: generating, based on the primary central curve, a second inner mesh curve and a second outer mesh curve, the second inner mesh curve being positioned along a third horizontal plane and the second outer mesh curve being positioned along a fourth horizontal plane, the third horizontal plane being parallel to and vertically offset from the first horizontal plane and the fourth horizontal plane being parallel to and vertically offset from the second horizontal plane; the second inner mesh curve being offset along the common median axis posteriorly relative to the primary central curve along the third horizontal plane; and the second outer mesh curve being offset along the common median axis anteriorly relative to the primary central curve along the fourth horizontal plane; projecting the plurality of primary midpoints onto the second inner mesh curve and the second outer mesh curve, thereby generating a second plurality of inner midpoints and a second plurality of outer midpoints; and generating a second segment of the reconstructed 3D representation of the gingiva by joining each one from the plurality of primary midpoints with respective ones from the second plurality of inner midpoints and from the second plurality of outer midpoints.

In some implementations of the method, the method further comprises causing display of the first and second segments of the reconstructed 3D representation of the gingiva.

In some implementations of the method, each segmentation loop of the plurality of segmentation loops is generated by: generating a preliminary segmentation loop based on segmentation of respective representations of the gingiva and the plurality of teeth on the 3D representation of the arch form; identifying in the preliminary segmentation loop a plurality of vertices; and adjusting a distance between at least some of the vertices, to generate the segmentation loop.

In some implementations of the method, the segmenting comprises applying one or more of the following functions: thresholding, clustering, edge detection, smoothing, and closing the loop.

In some implementations of the method, the method further comprises generating, between a given pair of adjacent segmentation loops of the plurality of segmentation loops, an outer arc and an inner arc for interconnecting the given pair of adjacent segmentation loops, thereby generating a primary border curve.

In some implementations of the method, the method further comprises generating, between the given pair of adjacent segmentation loops of the plurality of segmentation loops, a tween curve originating in a respective one of the plurality of primary midpoints, the tween curve extending through the outer arc and the inner arc, thereby generating a plurality of tween curves; and wherein the joining each one from the plurality of primary midpoints with respective ones from the first plurality of inner midpoints and from the first plurality of outer midpoints is based on a respective one of the plurality of tween curves.

In some implementations of the method, the distance between the at least some of the vertices is adjusted to be equal.

In some implementations of the method, the primary central curve is generated using a Bezier curve.

In some implementations of the method, the method further comprises using the reconstructed 3D representation of the gingiva to plan an orthodontic treatment.

In some implementations of the method, the 3D representation of the gingiva comprises a plurality of mesh elements which are not ordered, and wherein the generated 3D representation of the gingiva comprises a plurality of ordered mesh elements.

Finally, according to a sixth broad aspect of the present technology, there is provided a system for reconstructing a 3D representation of a gingiva associated with an arch form of a subject. The system comprises a processor configured to execute a method. The method comprises: acquiring a 3D representation of an arch form associated with the subject, the 3D representation including a representation of the gingiva and a plurality of teeth of the subject; the 3D representation of the arch form including data of a transverse plane associated with a skull of the subject; the transverse plane being associated with a common median axis lying therein and a common vertical axis perpendicular thereto; segmenting, in the 3D representation of the arch form, associated representations of the plurality of teeth and the gingiva to generate a plurality of segmentation loops, each segmentation loop respectively associated with each tooth of the plurality of teeth and representing an interface of a given tooth with the gingiva; determining, between each adjacent two segmentation loops of the plurality of segmentation loops, a midpoint, thereby generating a plurality of primary midpoints for the plurality of segmentation loops; based on the plurality of midpoints, generating a primary central curve. Thus, the primary central curve may be bisected by the common median axis. The method further comprises: generating, based on the primary central curve, a first inner mesh curve and a first outer mesh curve, the first inner mesh curve positioned along a first horizontal plane and the first outer mesh curve positioned along a second horizontal plane, both the first horizontal plane and the second horizontal plane being parallel to the transverse plane and being vertically offset, along the common vertical axis, from a highest vertex of the plurality of segmentation loops; the first inner mesh curve being offset along the common median axis posteriorly relative to the primary central curve along the first horizontal plane; and the first outer mesh curve being offset along the common median axis anteriorly relative to the primary central curve along the second horizontal plane; projecting the plurality of primary midpoints onto the first inner mesh curve and the first outer mesh curve, thereby generating a first plurality of inner midpoints and a first plurality of outer midpoints; generating a first segment of the reconstructed 3D representation of the gingiva by joining each one from the plurality of primary midpoints with respective ones from the first plurality of inner midpoints and from the first plurality of outer midpoints; and causing display of the first segment of the reconstructed 3D representation of the gingiva.

In some implementations of the system, the processor is further configured to generate a second segment of the reconstructed 3D representation of the gingiva by: generating, based on the primary central curve, a second inner mesh curve and a second outer mesh curve, the second inner mesh curve and the second outer mesh curve being positioned along a third horizontal plane and a fourth horizontal plane, both the third horizontal plane and the fourth horizontal plane being parallel to and vertical offset from the first horizontal plane and the second horizontal plane, respectively; the second inner mesh curve being offset along the common median axis posteriorly relative to the primary central curve along the third horizontal plane; and the second outer mesh curve being offset along the common median axis anteriorly relative to the primary central curve along the fourth horizontal plane; projecting the plurality of primary midpoints onto the second inner mesh curve and the second outer mesh curve, thereby generating a second plurality of inner midpoints and a second plurality of outer midpoints; and generating a second segment of the reconstructed 3D representation of the gingiva by joining each one from the plurality of primary midpoints with respective ones from the second plurality of inner midpoints and from the second plurality of outer midpoints.

In some implementations of the system, the processor is further configured to cause display of the first and second segments of the reconstructed 3D representation of the gingiva.

In some implementations of the system, each segmentation loop of the plurality of segmentation loops is generated by: generating a preliminary segmentation loop based on segmentation of respective representations of the gingiva and the plurality of teeth on the 3D representation of the arch form; identifying in the preliminary segmentation loop a plurality of vertices; and adjusting a distance between at least some of the vertices, to generate the segmentation loop.

In some implementations of the system, the processor is further configured to generate, between a given pair of adjacent segmentation loops of the plurality of segmentation loops, an outer arc and an inner arc for interconnecting the given pair of adjacent segmentation loops, thereby generating a primary border curve.

In some implementations of the system, the processor is further configured to generate, between the given pair of adjacent segmentation loops of the plurality of segmentation loops, a tween curve originating in a respective one of the plurality of primary midpoints, the tween curve extending through the outer arc and the inner arc, thereby generating a plurality of tween curves; and wherein the joining each one from the plurality of primary midpoints with respective ones from the first plurality of inner midpoints and from the first plurality of outer midpoints is based on a respective one of the plurality of tween curves.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

In the context of the present specification, the term "parametric equivalent model" of a given tooth (or of a specific portion thereof, such as a root portion thereof, for example) refers to a mathematical model of the given tooth (such as a 3D mesh representation, for example) indicative of certain parameters of the given tooth determined either statistically or analytically, such as, without limitation: overall dimensions of the given tooth, anatomical features thereof (a number of root branches, curvature thereof), solidity, and the like. Typically, the parametric equivalent model is indicative only of a limited number of the parameters associated with the given tooth, needed at a present phase of the orthodontic treatment for further planning thereof, Thus, the parametric equivalent model may be referred to as a simplified model of the given tooth, as opposed to an anatomically accurate 3D model of the given tooth. Accordingly, using the parametric equivalent model of the given tooth for determining the orthodontic treatment may allow computational resource efficiency.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
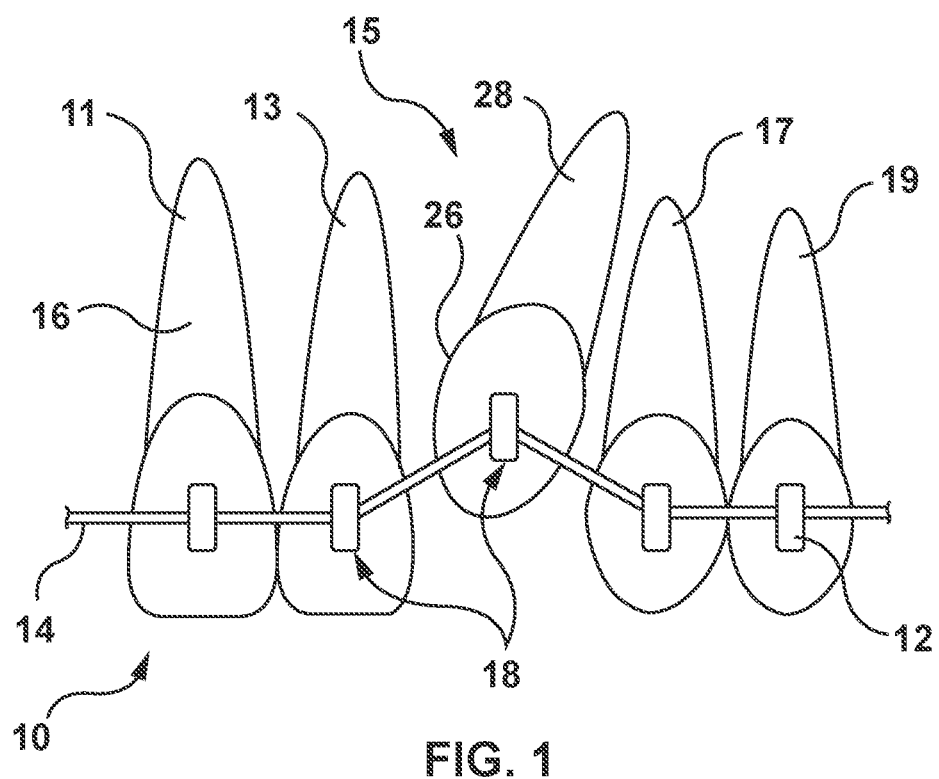
FIG. 1 depicts a schematic diagram of an orthodontic appliance attached to five teeth of a plurality of teeth of a subject.

Certain aspects and embodiments of the present technology are directed to methods of and systems for generating an augmented 3D representation of a crown portion for a given tooth based on segmenting a received raw 3D representation thereof from a 3D representation of an arch from of a subject. The subject may be receiving, or soon to receive, an orthodontic treatment. An accurate reconstruction of the augmented 3D representation of the crown portion may allow for a more accurate planning of the orthodontic treatment, which can in turn improve overall effectiveness and efficacy of the orthodontic treatment.

Further, it should be expressly understood that, in the context of the present specification, the term "orthodontic treatment" is broadly referred to as any type of medical intervention aimed at correcting malocclusions associated with the subject, including surgical and non-surgical manipulations, such as, but not limited to, using aligners. Further, the orthodontic treatment, as referred to herein, may be determined by a professional practitioner in the field of dentistry (such as an orthodontist, a maxillofacial surgeon, for example), or automatically by a specific software, based on respective image data and input parameters associated with the subject.

Certain non-limiting embodiments of the present technology minimize, reduce or avoid some of the problems noted in association with the prior art. For example, by implementing certain embodiments of the present technology in respect of generating the augmented 3D representation of the crown portion for the given tooth, some or all of the following advantages may be obtained: a more efficient and accurate approach to modelling forces imposed on the given tooth, and thus a more accurate modelling of the respective movements thereof in the course of the orthodontic treatment. This is achieved in certain non-limiting embodiments of the present technology by (1) generating the augmented 3D representation of the crown portion only based on raw image data (that is, a raw 3D representation of the crown portion) indicative thereof obtained through conventional imaging techniques currently used in orthodontics (such as the intra-oral scanning techniques), without the need for obtaining and processing additional image data associated with the subject, including, for example, CT and/or MR scans, or panoramic radiographs representative of the arch form of the subject including those of the given tooth; and (2) generating the augmented 3D representation of the crown portion, which has a smooth surface representative of the actual anatomical configuration of the crown portion and derived from portions of the raw 3D representation of the crown portion having been established to be accurately representative thereof.

Thus, methods and systems provided herein, according to certain non-limiting embodiments of the present technology, allow achieving a higher accuracy in planning and predictability of orthodontic treatments, and consequently, resolving malocclusions more efficiently and effectively whilst using more commonly available imaging techniques for generating the image data associated with the subject. For example, the image data used for planning the orthodontic treatment, in some non-limiting embodiments of the present technology, may include images indicative of a surface of the subject's gingiva and respective surfaces of the subject's teeth, such as those obtained with intraoral scans. Images of the roots of the subject s teeth or interdental spaces may not be required. This may also allow for a faster processing of such image data by a processor.

According to some non-limiting embodiments of the present technology, the methods for generating the augmented 3D representation of the crown portion described herein may be considered as a separate process. However, in other non-limiting embodiments of the present technology, these methods may be part of a more general process of reconstructing a comprehensive 3D representation of a subject's arch form (also referred to herein as an "augmented" 3D representation thereof), which is further used for determining the orthodontic treatment, for example, by displaying the reconstructed tooth to a practitioner using a display or by using a computer algorithm to generate the treatment plan based on the reconstructed representation. In these embodiments, the comprehensive 3D representation of the subject's arch form is generated based on a raw 3D representation thereof (that is an unprocessed representation thereof, directly obtained, for example, surface imaging techniques such as intra-oral scanning techniques, as will be explained further below).

Broadly speaking, according to the non-limiting embodiments of the present technology, methods for generating the comprehensive 3D representation of the subject's arch form may include:
  acquiring image data indicative of the raw 3D representation of the subject's arch form including at least a raw 3D representation of the crown portion of the given tooth and a raw 3D representation of a gingiva;
  augmenting the raw 3D representation of the crown portion by segmentation thereof from respective raw 3D representations of crown portions of adjacent teeth and that of the gingiva, thereby generating an augmented 3D representation of the crown portion of the given tooth (which is the object of the present document);
  reconstructing, based on the augmented 3D representation of the crown portion, the 3D representation of the root portion for the given tooth, thereby generating a 3D representation of the given tooth; and
  augmenting, based at least on the 3D representation of the crown portion, the raw 3D representation of the gingiva, thereby generating a comprehensive 3D representation thereof.

As it may become apparent, the last step may further include merging the 3D representation of the given tooth with the comprehensive 3D representation of the gingiva, whereby the comprehensive 3D representation of the subject's arch form may be generated. It should be also noted that the order of steps listed above can be changed without departing from the scope of the non-limiting embodiments of the present technology.

Thus, the description of the non-limiting embodiments of the present technology directed to reconstruction of the augmented 3D representation of the crown portion will be provided in concert with description of the above-listed steps for the generating the comprehensive 3D representation of the subject's arch form.

Orthodontic Treatment

Figure 2:
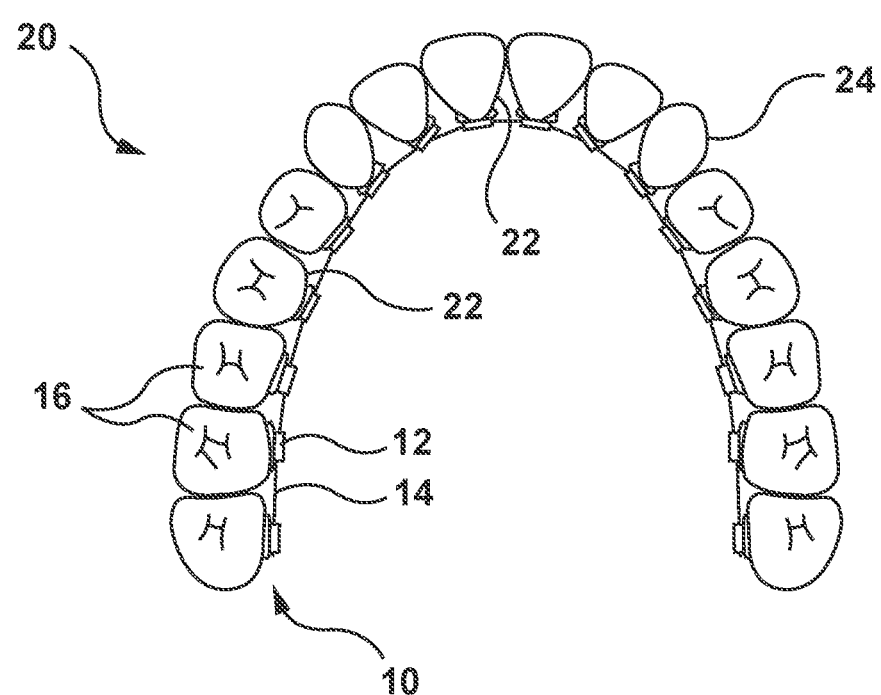
FIG. 2 depicts a schematic diagram of an upper arch form of the subject of FIG. 1 showing the orthodontic appliance of FIG. 1 attached thereto.

Referring initially to FIGS. 1 and 2, there is depicted an example orthodontic appliance 10 as part of the orthodontic treatment, to which certain aspects and embodiments of the present technology can be applied. Generally speaking, the orthodontic appliance 10 comprises brackets 12 and an archwire 14. The archwire 14 is made of a shape memory alloy such as Nitinol™, but can also be made of any other shape memory alloy or material having certain elasticity properties. The brackets 12 are respectively provided on some of upper teeth 16 (depicted individually as 11, 13, 15, 17, and 19), and the archwire 14 extends between, and is connected to each of the brackets 12. In the depicted embodiments of FIG. 1, the orthodontic treatment is aimed at misalignment of the tooth 15; hence the orthodontic appliance 10 is configured to cause the tooth 15 to move in a predetermined direction (such as downwardly) for alignment thereof with neighbouring ones of the upper teeth 16, that is, teeth 11, 13, 17, and 19.

As it can be appreciated from FIG. 1, the tooth 15 includes a crown portion 26 and a root portion 28. The archwire 14 imposes a given force, caused by bends 18, on the tooth 15 at a respective one of the brackets 12 having been installed on the crown portion 26. Thus, due to the shape memory effect of the archwire 14, the tooth 15 will gradually move to an aligned position relative to the other one of the upper teeth 16.

With reference to FIG. 2, as one non-limiting example, the orthodontic appliance 10 has been applied to all the upper teeth 16 of an upper arch form 20 of the subject, with the brackets 12 being attached to an internal surface 22 of the upper teeth 16. However, it should be noted that, in another non-limiting example, the orthodontic appliance 10 may be configured to be installed on an external surface 24 of the upper teeth 16.

It is contemplated that, according to some non-limiting embodiments of the present technology, the orthodontic appliance 10 may comprise orthodontic appliances of different types, shapes, sizes and configurations, such as, without limitation, multi-strand wires, strips, retainers, and plates. Furthermore, the bends 18 in the archwire 14 may comprise rounded corners or loops. It will also be appreciated that the orthodontic appliance 10 may be used for treating any type of teeth misalignment or malocclusion, including but not limited to closing gaps ("space closure"), creating/widening gaps, tooth rotation, tooth intrusion/extrusion, and translation, to name a few.

It is contemplated that, before installing the orthodontic appliance 10 onto the upper teeth 16 for the alignment of the tooth 15, movements thereof, in the course of the orthodontic treatment, should be modelled to ensure that the tooth 15 will eventually reach the aligned position over an expected period. To that end, image data indicative of crown portions (such as the crown portion 26 of the tooth 15) of the upper teeth 16 may be used to model the given force to be applied onto the tooth 15, which may include, without being limited to: a magnitude of the given force, a direction thereof, and an application point thereof within the crown portion 26. Accordingly, based on the image data indicative of the crown portions, the modelling may, for example, allow avoiding collisions between the crown portion 26 of the tooth 15 with any one of those teeth of the upper teeth 16 adjacent thereto.

However, in certain cases, the modelling of the tooth movements may be conducted to prevent other undesired effects of the orthodontic treatment. For example, the modelling may allow ensuring that the current orthodontic treatment would not cause damage to any of the upper teeth 16 at the level of their root portions, as well as to other structures associated therewith, such as tissues of an upper gingiva (such as an upper gingiva 36 depicted in FIG. 6), those of a maxillary alveolar bone (not depicted), proximal nerve pathways and blood vessels (not depicted), and the like. Further, when modelling tooth movements, considerations can be made in respect of overall comfort of the orthodontic treatment for the subject, on which his or her tolerance and adherence to the orthodontic treatment may depend.

Figure 3:
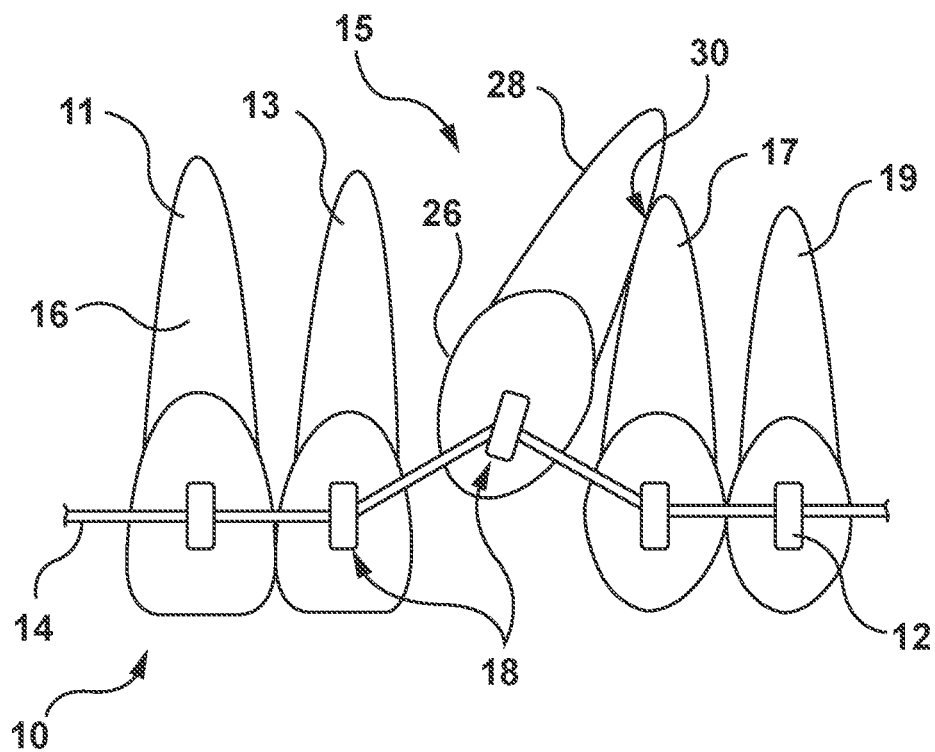
FIG. 3 depicts a schematic diagram of an intermediate phase of the orthodontic treatment including applying the orthodontic appliance of FIG. 1, in accordance with certain non-limiting embodiments of the present technology.

For example, with reference to FIG. 3, there is depicted a schematic diagram of a phase of the orthodontic treatment based on applying the orthodontic appliance 10 to the upper teeth 16, in accordance with certain non-limiting embodiments of the present technology. The depicted phase may be an intermediate phase or an initial phase, for example.

As it can be appreciated, at the phase depicted in FIG. 3, the root portion 28 of the tooth 15, in the course of the movement thereof towards the aligned position, collides with a root portion (not separately labelled) of the tooth 17 adjacent thereto, thereby forming a collision area 30. Accordingly, the collision area 30 may be associated with undesired effects, such as damage of one of the tooth 15 and the tooth 17, or discomfort (pain, for example) caused to the subject.

In another example (not depicted), the collision may occur between the crown portion 26 of the tooth 15 and a crown portion (not separately labelled) of the tooth 17, which may result in damage (such as chipping or cracks) to at least one of the crown portion 26 and the crown portion, or also pain to the subject from pressure therebetween.

In yet another example (not depicted), the root portion 28 may deviate in another direction causing damage to the upper gingiva 36, which may result in the root portion 28 protruding through the upper gingiva 36 causing to the subject, for example, an aesthetic defect or, again, pain from using the orthodontic appliance 10.

Overall, the image data solely indicative of the crown portion 26 may be insufficient for a comprehensive analysis of the movements and determining intermediate positions of the tooth 15, as a whole, during the orthodontic treatment, which may hence require image data indicative of the root portion 28 thereof and that indicative of the upper gingiva 36, for example. Such comprehensive analysis may allow for a more accurate planning of the orthodontic treatment of the subject, aimed at mitigating the risks of at least some of the undesired effects thereof. How the raw image data indicative of the crown portion 26 may be used for generating the augmented 3D representation thereof will be described below with reference to FIGS. 7 to 12. Further, how the augmented 3D representation of the crown portion 26 may be used for generating image data indicative of the root portion 28 will be described further below with reference to FIGS. 13 to 21. Finally, how the so generated image data may be used, along with the raw 3D representation of the upper gingiva 36, to generate the comprehensive 3D model thereof will be described with reference to FIGS. 22 to 35.

System

Figure 4:
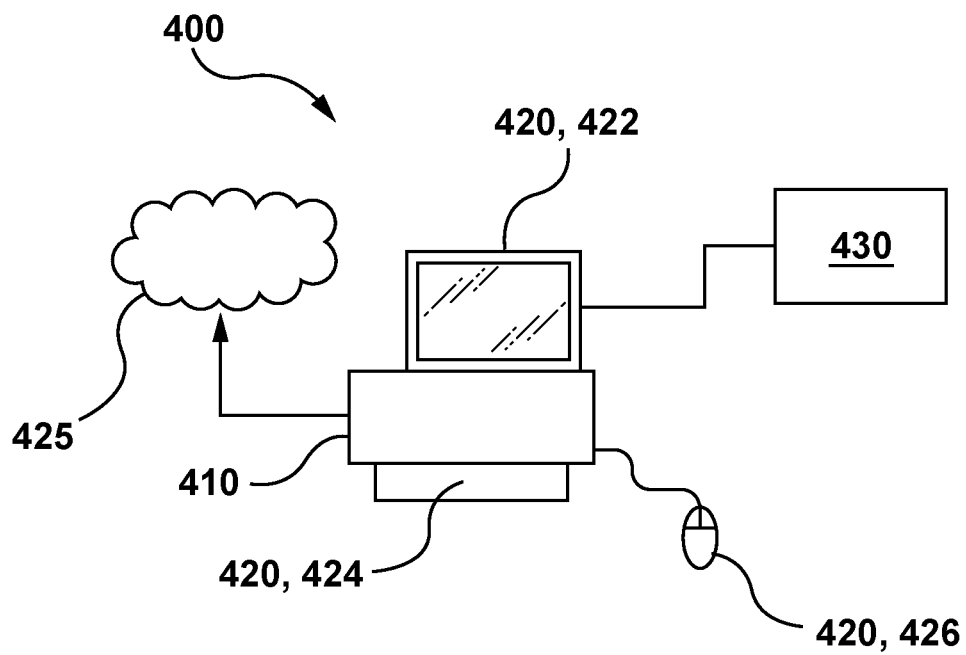
FIG. 4 depicts a schematic diagram of a system for reconstructing 3D representations of root portions associated with the plurality of teeth of the subject of FIG. 1 based on associated 3D representations of crown portions for determining the orthodontic treatment, in accordance with certain embodiments of the present technology.
Figure 5:
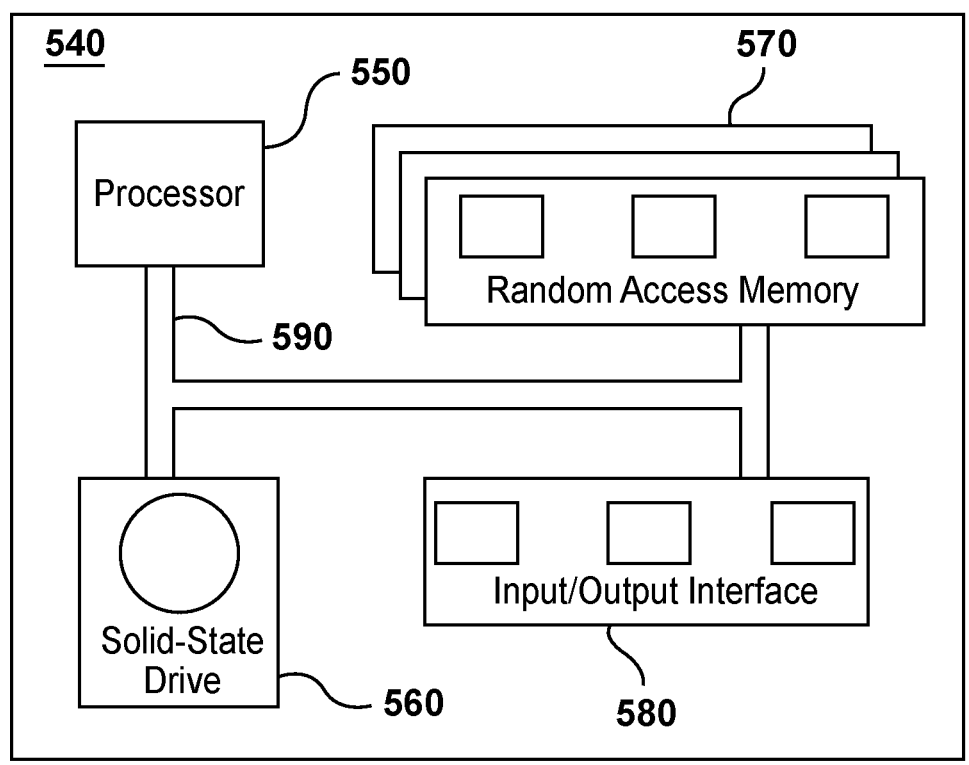
FIG. 5 depicts a schematic diagram of a computing environment of the system of FIG. 4, in accordance with certain embodiments of the present technology.

Referring to FIGS. 4 and 5, there is depicted a schematic diagram of a system 400 suitable for determining root reconstructions such as for determining the orthodontic treatment for the subject, in accordance with certain non-limiting embodiments of the present technology.

It is to be expressly understood that the system 400 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 400 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 400 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 400 of FIG. 4 comprises a computer system 410. The computer system 410 may be configured, by pre-stored program instructions, to generate, based on image data associated with the subject, a comprehensive arch form 3D representation of the upper arch form 20 including: (i) augmented crown 3D representations, (ii) root 3D representations for the upper teeth 16 thereby generating respective tooth 3D representations, and (iii) a comprehensive gingiva 3D representation of the upper gingiva 36, according to certain non-limiting embodiments of the present technology. In some non-limiting embodiments of the present technology, the computer system 410 may further be configured to determine, based at least on one of the respective tooth 3D representations and the comprehensive gingiva 3D representation, the orthodontic treatment for the subject, as will be described further It should be noted that in various non-limiting embodiments of the present technology, the computer system 410 may be configured to execute the steps (i), (ii), and (iii) separately and/or independently. Further, the order of these steps may be changed without departing from the scope of the present technology.

To that end, in some non-limiting embodiments of the present technology, the computer system 410 is configured to receive image data pertaining to the subject or to a given orthodontic treatment. For example, the computer system 410 may be configured to process the received image data to generate the comprehensive 3D representation of the subject's arch form. According to some non-limiting embodiments of the present technology, the computer system 410 may receive the image data via local input/output interface (such as USB, as an example, not separately depicted). In other non-limiting embodiments of the present technology, the computer system 410 may be configured to receive the image data over a communication network 425, to which the computer system 410 is communicatively coupled.

In some non-limiting embodiments of the present technology, the communication network 425 is the Internet and/or an Intranet. Multiple embodiments of the communication network may be envisioned and will become apparent to the person skilled in the art of the present technology. Further, how a communication link between the computer system 410 and the communication network 425 is implemented will depend, inter alia, on how the computer system 410 is implemented, and may include, but is not limited to, a wire-based communication link and a wireless communication link (such as a Wi-Fi communication network link, a 3G/4G communication network link, and the like).

It should be noted that the computer system 410 can be configured for receiving the image data from a vast range of devices. Some of such devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 410 may be configured to receive the image data associated with the subject directly from an imaging device 430 communicatively coupled thereto. Broadly speaking the imaging device 430 may be configured (for example, by a processor 550 depicted in FIG. 5) to capture and/or process the image data of the upper teeth 16 and the periodontium (not depicted) of the subject. In certain non-limiting embodiments of the present technology, the image data may include, for example, one or more of: (1) images of external surfaces of respective crown portions (such as the crown portion 26 of the tooth 15) of the upper teeth 16, (2) images of an external surface of the periodontium including those of the upper gingiva (not depicted), the alveolar maxillary bone (not depicted), and images of superficial blood vessels and nerve pathways associated with the upper teeth 16; and (3) images of an oral region. By doing so, the imaging device 430 may be configured, for example, to capture image data of the upper arch form 20 of the subject. In another example, the imaging device may also be configured to capture and/or process image data of a lower arch form (such as the lower arch form 21 depicted in FIG. 6) associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 430 may comprise an intra-oral scanner enabling to capture direct optical impressions of the upper arch form 20 of the subject.

In a specific non-limiting example, the intraoral scanner can be of one of the types available from MEDIT, corp. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 430 may comprise a desktop scanner enabling to digitize a mold representing the upper arch form 20. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from Dental Wings, Inc. of 2251, ave Letourneux, Montréal (QC), Canada, H1V 2N9. It should be expressly understood that the desktop scanner can be implemented in any other suitable equipment.

Further, it is contemplated that the computer system 410 may be configured for processing of the received image data. The resulting image data of the upper arch form 20 received by the computer system 410 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 410 may further comprise a corresponding computing environment.

With reference to FIG. 5, there is depicted a schematic diagram of a computing environment 540 suitable for use with some implementations of the present technology. The computing environment 540 comprises various hardware components including one or more single or multi-core processors collectively represented by the processor 550, a solid-state drive 560, a random access memory 570 and an input/output interface 580. Communication between the various components of the computing environment 540 may be enabled by one or more internal and/or external buses 590 (e.g. a PCI bus, universal serial bus, IEEE 1394 "Firewire" bus, SCSI bus, Serial-ATA bus, ARINC bus, etc.), to which the various hardware components are electronically coupled.

The input/output interface 580 allows enabling networking capabilities such as wire or wireless access. As an example, the input/output interface 580 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 580 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 560 stores program instructions suitable for being loaded into the random access memory 570 and executed by the processor 550, according to certain aspects and embodiments of the present technology. For example, the program instructions may be part of a library or an application.

In some non-limiting embodiments of the present technology, the computing environment 540 is implemented in a generic computer system which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 540 can be implemented may be envisioned without departing from the scope of the present technology.

Referring back to FIG. 4, the computer system 410 has at least one interface device 420 for providing an input or an output to a user of the system 400, the interface device 420 being in communication with the input/output interface 580. In the embodiment of FIG. 4, the interface device is a screen 422. In other non-limiting embodiments of the present technology, the interface device 420 may be a monitor, a speaker, a printer or any other device for providing an output in any form such as an image form, a written form, a printed form, a verbal form, a 3D model form, or the like.

In the depicted embodiments of FIG. 4, the interface device 420 also comprises a keyboard 424 and a mouse 426 for receiving input from the user of the system 400. Other interface devices 420 for providing an input to the computer system 410 can include, without limitation, a USB port, a microphone, a camera or the like.

The computer system 410 may be connected to other users, such as through their respective clinics, through a server (not depicted). The computer system 410 may also be connected to stock management or client software which could be updated with stock when the orthodontic treatment has been determined and/or schedule appointments or follow-ups with clients, for example.

Image Data

As previously alluded to, according to the non-limiting embodiments of the present technology, the processor 550 may be configured to: (1) receive the image data associated with the subject's teeth (such as the upper teeth 16); and (2) based on the received image data, determine, for each of the upper teeth 16, the orthodontic treatment for the subject. For example, based on the received data, the processor 550 may be configured to determine tooth movements of the tooth 15 towards the aligned position thereof within the other ones of the upper teeth 16, as described above with reference to FIGS. 1 to 3.

According to some non-limiting embodiments of the present technology, having received the image data, the processor 550 may be configured to generate 3D models of arch forms of the subject.

Figure 6:
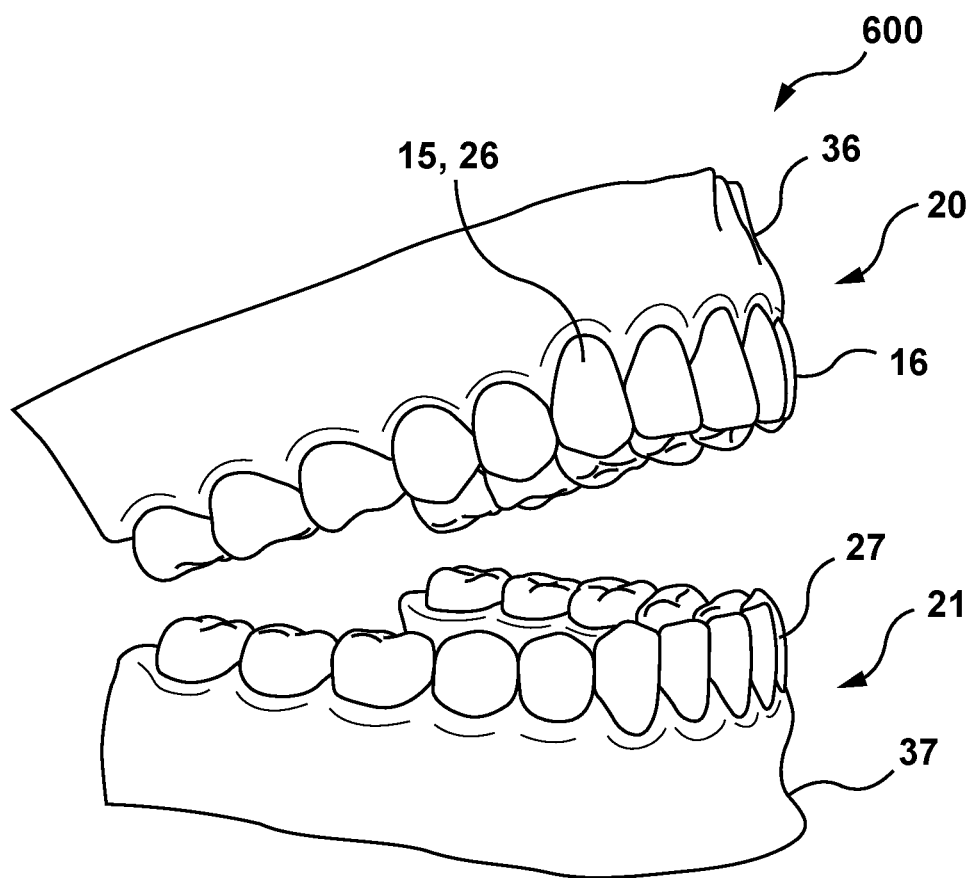
FIG. 6 depicts a perspective view of a 3D model of the upper arch form and a lower arch form of the subject of FIG. 1, in accordance with certain non-limiting embodiments of the present technology.

With reference to FIG. 6, there is depicted a perspective view of a 3D model 600 representing a current configuration of the upper arch form 20 (also referred to herein as "maxillary arch form") and the lower arch form 21 (also referred to herein as "mandibular arch form") of the subject, in accordance with the non-limiting embodiments of the present technology.

According to the non-limiting embodiments of the present technology, the upper arch form 20 comprises the upper teeth 16 (also referred to herein as "maxillary teeth") and the upper gingiva 36, and the lower arch form 21 comprises lower teeth 27 (also referred to herein as "mandibular teeth") and a lower gingiva 37. As it can be appreciated, the upper teeth 16 and the lower teeth 27 are represented, in the 3D model 600, by respective crown portions associated therewith, such as the crown portion 26 of the tooth 15.

It should be expressly understood that, although the description herein below will be given in respect of the upper arch form 20 of the subject (and associated therewith the upper teeth 16 and the upper gingiva 36) for the sake of clarity and simplicity thereof, and in no way as a limitation, the non-limiting embodiments of the present technology can also apply to the lower teeth 27 with certain alterations, which will be explicitly indicated below where necessary.

Figure 10:
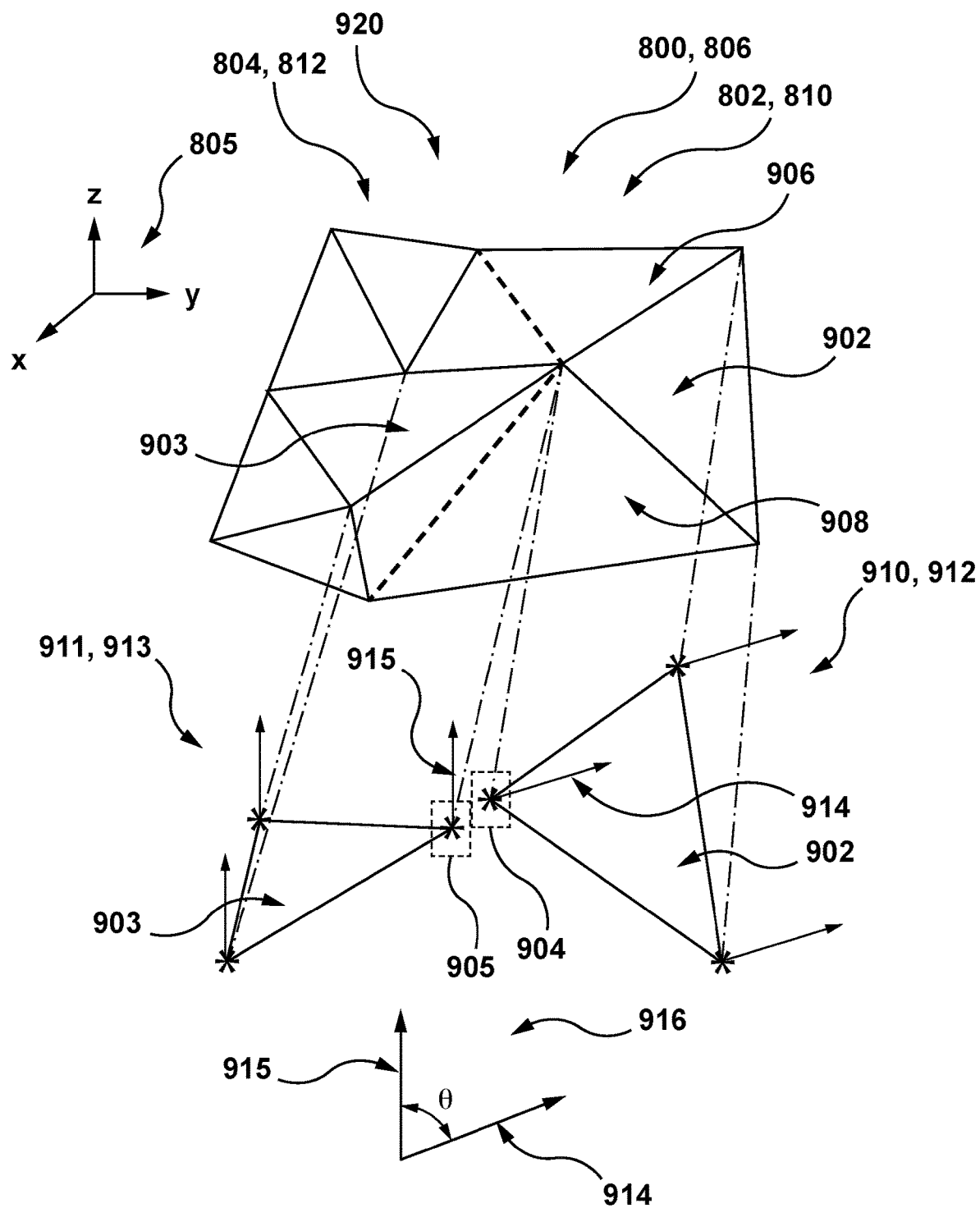
FIG. 10 depicts a schematic diagram of a step in the method of FIG. 8 executed by the processor of FIG. 5 for identifying and removing the digital garbage forming part of the raw crown 3D representation of FIG. 9 to generate a refined crown 3D representation associated with the given one of the plurality of teeth present in FIG. 1, in accordance with certain non-limiting embodiments of the present technology.

Further, according to some non-limiting embodiments of the present technology, in order to determine the orthodontic treatment, the processor 550 may be configured to isolate, in the 3D model 600, a 3D representation of the crown portion 26 (such as an augmented crown 3D representation 1020 depicted in FIG. 10, for example) from 3D representations of crown portions associated with other ones of the upper teeth 16, and from that of the upper gingiva 36. Further, the processor 550 may be configured to reconstruct, based on the 3D representation of the crown portion 26, a 3D representation of the root portion 28 (such as a root 3D representation 1620 depicted in FIG. 17, for example), thereby generating a complete 3D representation of the tooth 15 (such as a tooth 3D representation 1720 depicted in FIG. 17, for example), which complete 3D representation may be used for determining the orthodontic treatment.

However, the so generated 3D model 600 may not be accurately representative of actual configuration of at least some of the upper teeth 16. For example, the imaging device 430 of FIG. 4 may not be able to capture interdental spaces between each of the teeth accurately, for example, due to an inability thereof to reliably receive light having been reflected off the interdental spaces. This may result in the processor 550 generating the 3D model 600 including image artefacts (also known as "digital garbage") instead of data indicative of actual interdental spaces between the teeth of the subject, which may further render the 3D model 600 unreliable for further processing.

Figure 7:
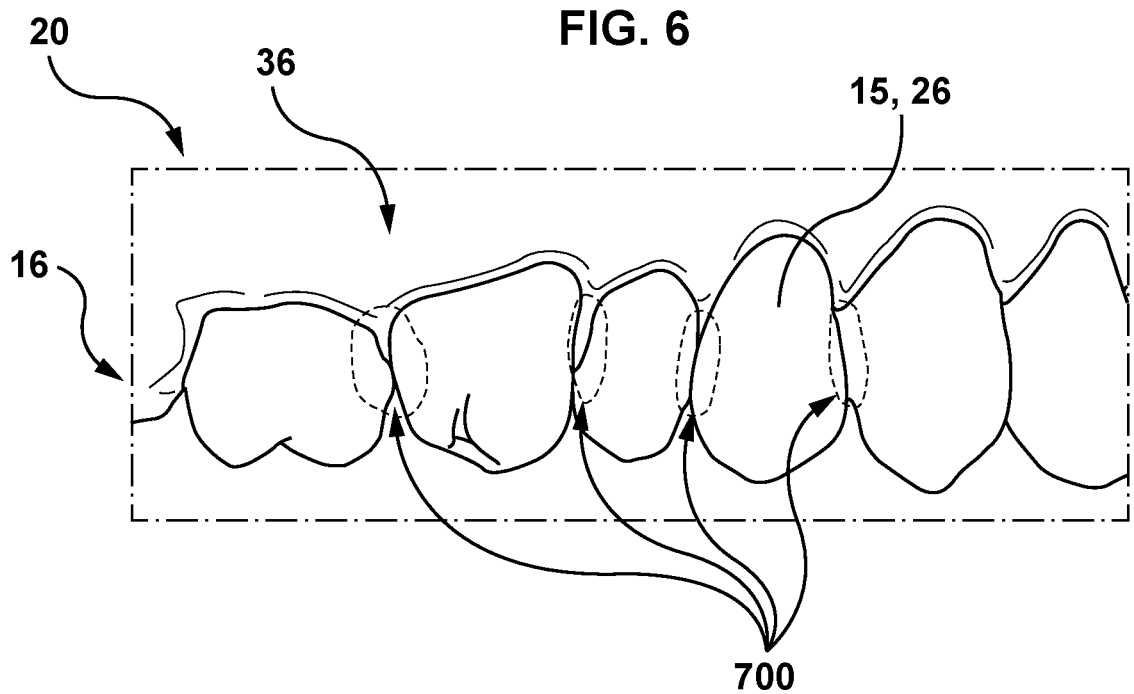
FIG. 7 depicts a portion of the 3D model of FIG. 6 including digital garbage to be removed therefrom, in accordance with certain non-limiting embodiments of the present technology.

With reference to FIG. 7, there is depicted a magnified view of the 3D model 600 representing a portion of the upper arch form 20 with some of the upper teeth 16 including image artefacts 700 instead of respective representations of interdental spaces therebetween, in accordance with certain non-limiting embodiments of the present technology.

In the context of the present specification, the term "image artefacts" of an image (such as the 3D model 600) representative of a real object (such as the upper arch form 20) broadly refers to portions of the image forming no part of the real object and generated, for example, due to imperfection of technical means (such as the imaging device 430) used for taking the image. As such, for a more accurate representation of the real object, the image artefacts need to be identified and removed from the image.

As it can be appreciated from FIG. 7, the image artefacts 700 represent anomalies in representing the upper teeth 16 and the upper gingiva 36 forming no part of the actual configuration thereof. Therefore, the 3D model 600 including the image artefacts 700 may not enable the generation of the 3D representation of the crown portion 26 indicative of actual surface thereof at a desired level of detail, providing instead a raw 3D representation thereof (such as a raw crown 3D representation 800 depicted in FIG. 8). This may, in turn, result in an inaccurate 3D representation of the root portion 28.

Thus, in certain non-limiting embodiments of the present technology, the processor 550 may be configured to execute a method 100 for identifying, in the 3D model 600, the image artefacts 700 and effectively eliminating them, thereby segmenting individual 3D representations of crown portions of the upper teeth 16 from each other and from that of the upper gingiva 36. By doing so, the processor 550 may be configured to restore, in the 3D model 600, an actual contour of a respective surface of each of the crown portions, thereby generating an augmented crown 3D representation (such as the augmented crown 3D representation depicted in FIG. 11) of the crown portion 26 of the tooth 15. How these non-limiting embodiments can be implemented will be described with reference to FIGS. 9 to 12.

Automatic Tooth Segmentation

Figure 8:
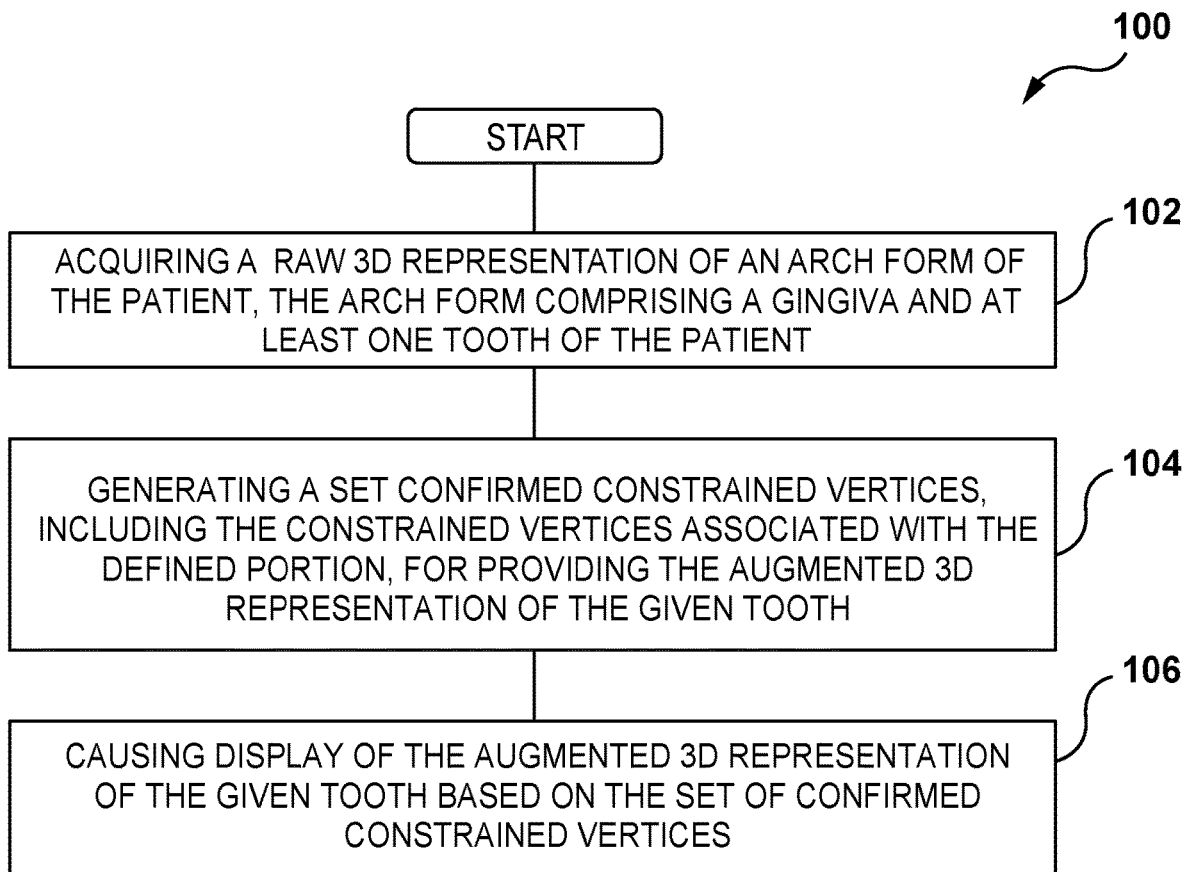
FIG. 8 depicts a flowchart diagram of a method for generating an augmented crown 3D representation of the crown portion of a given one of the plurality of teeth present in FIG. 1, in accordance with certain non-limiting embodiments of the present technology.

With reference to FIG. 8, there is depicted a flowchart diagram of the method 100 for generating the augmented crown 3D representation 1020 of the crown portion 26. According to certain non-limiting embodiments of the present technology, the method 100 can be executed by the processor 550 of the computer system 410.

Step 102: Acquiring a Raw 3D Representation of an Arch Form of the Patient, the Arch Form Comprising a Gingiva and at Least One Tooth of the Patient The method 100 commences at step 102 with acquiring a raw 3D representation of the upper arch form 20, such as that forming part of the 3D model 600, the process of receiving which is described hereinabove with reference to FIGS. 6 and 7.

Figure 9:
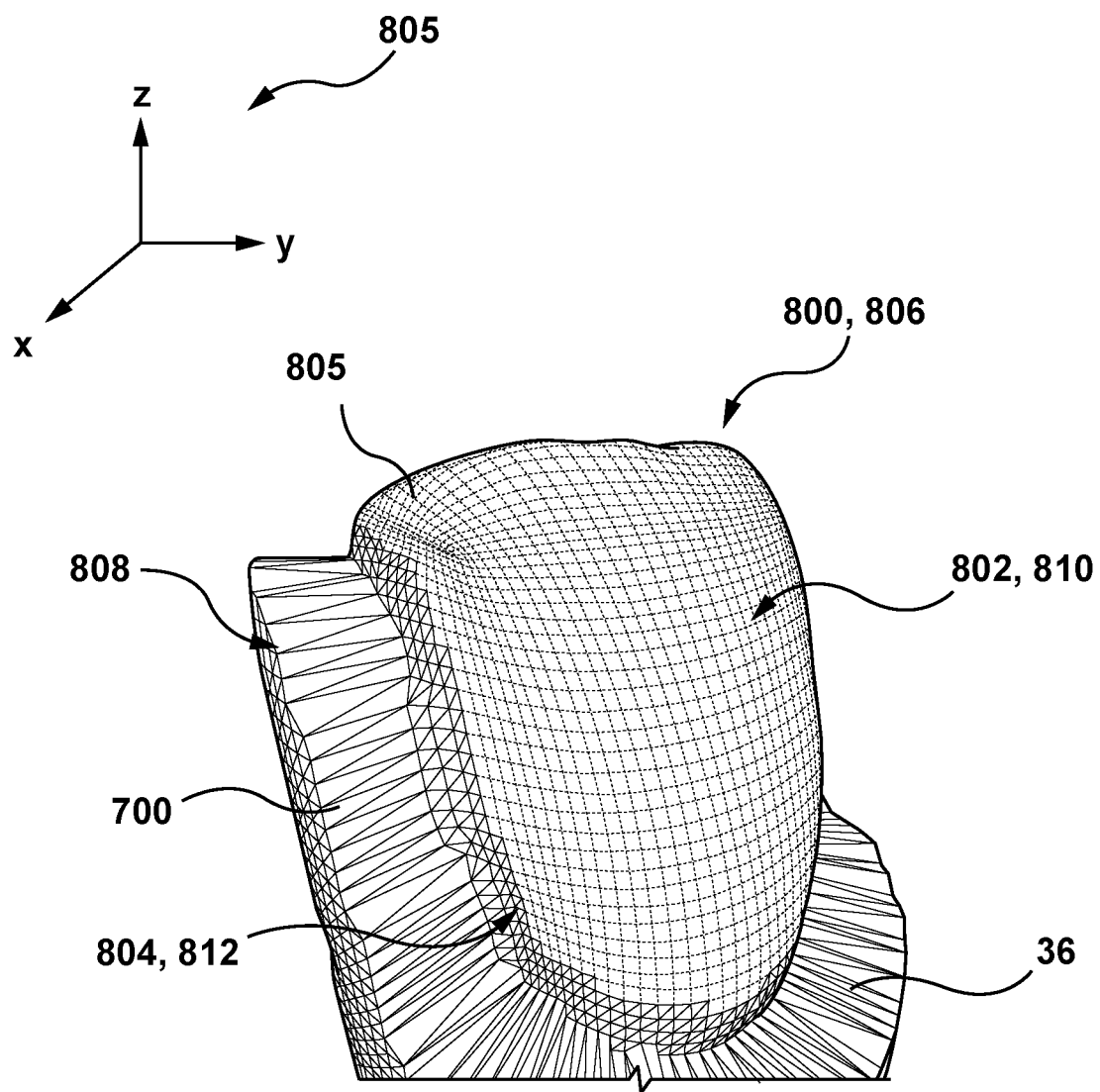
FIG. 9 depicts a raw crown 3D representation associated with the given one of the plurality of teeth present in FIG. 1, segmented from the 3D model of FIG. 6, and including some of the digital garbage, in accordance with certain non-limiting embodiments of the present technology.

Further, with reference to FIG. 9, there is depicted the raw crown 3D representation 800 of the crown portion 26, in accordance with certain non-limiting embodiments of the present technology. For example, in some non-limiting embodiments of the present technology, the processor 550 may be configured to isolate, from the 3D model 600, the raw crown 3D representation 800 of the crown portion 26 based on reference data associated with the tooth 15. The reference data may be based on historic data of a number of subjects, such as average maximum possible dimensions of crown portions. In alternative non-limiting embodiments of the present technology, to generate the raw crown 3D representation 800, the processor 550 may have been configured to use algorithms for analyzing changes of curvature within the 3D model 600.

In some non-limiting embodiments of the present technology, the processor 550 may be configured to generate the raw crown 3D representation 800 comprising a plurality of mesh elements 806. Although in the depicted embodiments of FIG. 9 each of the plurality of mesh elements 806 is a triangular mesh element, it should be expressly understood that in other non-limiting embodiments of the present technology, the plurality of mesh elements 806 may be represented by quadrilateral mesh elements, convex polygonal mesh elements, or even concave polygonal mesh elements, as an example, without departing from the scope of the present technology.

As can be appreciated from FIG. 9, the raw crown 3D representation 800 includes the image artefacts 700, which may impede the accurate determination of actual boundaries of the crown portion 26 of the tooth 15. Thus, the processor 550 may be configured to: (1) identify the image artefacts 700 in the raw crown 3D representation 800 of the crown portion 26; (2) remove image artefacts 700 therefrom; and (3) smooth the resulting surface thereof, thereby generating an augmented crown 3D representation of the crown portion 26. The augmented crown 3D representation may be further used to determine the orthodontic treatment for the subject.

Certain non-limiting embodiments of the present technology have been developed based on developers' appreciation that the image artefacts 700 may be identified based on a pre-defined portion of the raw crown 3D representation 800 known to accurately represent a respective actual portion of the crown portion 26 of the tooth 15—such as a defined portion 802 thereof as depicted in FIG. 9. To that end, the defined portion 802 of the raw crown 3D representation 800 may be used, by the processor 550, to determine overall smoothness of a surface of the augmented crown 3D representation 1020 of the crown portion 26, thereby identifying: (1) portions of the raw crown 3D representation 800 that correspond to the surface of the augmented crown 3D representation 1020, and that should thus be included therein; and (2) portions of the raw crown 3D representation 800 that do not correspond to the surface of the augmented crown 3D representation 1020. According to some non-limiting embodiments of the present technology, the processor 550 may further be configured to identify the latter as portions indicative of the image artefacts 700, which should be removed from the raw crown 3D representation 800.

In some non-limiting embodiments of the present technology, the processor 550 may be configured to determine the defined portion 802 based on a predetermined horizontal distance from at least one vertical edge of the raw crown 3D representation 800—such as a vertical edge 808—along a horizontal axis (not depicted) associated therewith.

In some non-limiting embodiments of the present technology, the horizontal axis associated with the raw crown 3D representation 800 may be defined, for example, based on a transverse anatomical plane (not separately depicted) associated with the subject's skull. In other non-limiting embodiments of the present technology, the horizontal axis may be defined as an axis extending between a most distant distal vertex (not depicted) of the plurality of mesh elements 806 and a most mesial vertex (not depicted) of the plurality of mesh elements 806, which may have been predetermined within the defined portion 802 of the raw crown 3D representation 800. Further, based on the so defined horizontal axis, the processor 550 may be configured to generate a coordinate system 805 for the raw crown 3D representation 800 of the crown portion 26.

According to some non-limiting embodiments of the present technology, to determine the predetermined horizontal distance, the processor 550 may be configured to execute (or otherwise have access to) an erosion function. In the context of the present specification, the term "erosion" broadly refers to morphological image processing developed in the field of mathematical morphology, and denotes a function configured to remove structural elements (such as some of the plurality of mesh elements 806) from boundaries of an image (such as the raw crown 3D representation 800 of the crown portion 26) based on a predetermined structuring element comprising a predetermined number of the structural elements, on whose configuration the output of the erosion function depends. In this regard, the configuration of the structuring element may include a size and a shape thereof, and certain image parameters associated with the structural elements of the image, such as light intensity or colour, for example. Accordingly, the structuring element can be said to move within the image akin to a sliding window, removing portions thereof that do not correspond to the configuration of the structuring element. By so doing, the erosion function may be configured to isolate only a substantive portion of the image.

Thus, broadly speaking, a value of the predetermined horizontal distance, determined by the processor 550 based on the erosion function, may be variable along the vertical edge 808 of the raw crown 3D representation 800. Thus, by applying the predetermined horizontal distance, the processor 550 may be configured to identify a plurality of constrained mesh elements 810 representing the defined portion 802, and the remainder—as a plurality of unconstrained mesh elements 812 representing an undefined portion 804 of the raw 3D representation 800 of the crown portion.

The method 100 hence advances to step 104.

Step 104: Generating a Set of Confirmed Constrained Vertices, Including the Constrained Vertices Associated with the Defined Portion, for Providing the Augmented 3D Representation of the Given Tooth At step 104, according to certain non-limiting embodiments of the present technology, having identified the defined portion 802 and the undefined portion 804 of the raw crown 3D representation 800, the processor 550 may be configured to identify the image artefacts 700 in the raw crown 3D representation 800. To that end, the processor 550 may be configured to use the plurality of constrained mesh elements 810 for determining if a given adjacent one of the plurality of unconstrained mesh elements 812 should be re-identified as one of the plurality of constrained mesh elements 810 and transferred thereto, or else be identified as forming part of the image artefacts 700 and removed from the raw crown 3D representation 800. By so doing, the processor 550 may be configured to generate a plurality of confirmed constrained mesh elements (such as the plurality of confirmed constrained mesh elements 920 depicted in FIGS. 10 and 11) representing the augmented crown 3D representation 1020 of the crown portion 26, as will be explained in greater detail below.

In some non-limiting embodiments of the present technology, the processor 550 may be configured to determine if the given one of the plurality of unconstrained mesh elements 812 should be included in the plurality of confirmed constrained mesh elements 920 based on analyzing a spatial position thereof relative to a respective one of the plurality of constrained mesh elements 810 within the coordinate system 805.

With reference to FIG. 10, there is depicted a schematic diagram of executing, by the processor 550, step 104 for identifying each one of the plurality of unconstrained mesh elements 812 as being representative of the crown portion 26 or of the image artefacts 700, thereby generating the plurality of confirmed constrained mesh elements 920, in accordance with certain non-limiting embodiments of the present technology.

According to certain non-limiting embodiments of the present technology, the processor 550 may be configured to determine if an unconstrained mesh element 903 is to be included in the plurality of confirmed constrained mesh elements 920 or to be considered part of the image artefacts 700 by determining an angular position thereof relative to a first constrained mesh element 902 adjacent thereto. Thus, the processor 550 may be configured to include, in the plurality of confirmed constrained mesh elements 920, those, from the plurality of unconstrained mesh elements 812, having certain degree of smoothness relative to the plurality of constrained mesh elements 810.

To that end, the processor 550 may be configured to first determine, at each vertex of each one of the plurality of mesh elements 806, an associated vertex normal vector. Thus, by determining angular difference between a pair of immediately adjacent vertex normal vectors defined at respective vertices of two adjacent mesh elements of the plurality of mesh elements 806, discontinuity of smoothness between the two adjacent mesh elements may be detected, as will be explained below.

It should be expressly understood that how the processor 550 can be configured to determine the associated vertex normal vector is not limited, and, typically, may include analyzing spatial positions of associated edges of a respective one of the plurality of mesh elements 806, face normal vectors associated therewith (not depicted), and the like, within the coordinate system 805. In this regard, as it will be appreciated by one skilled in the art, the processor 550 may be configured to apply one of the following techniques to determine the associated vertex normal vector: a mean weighted equality algorithm, a mean weighted by angle algorithm, a mean weighted by sine and edge length reciprocal algorithm, a mean weighted by areas of adjacent mesh elements, and the like. Details of implementation of some of these algorithms may be obtained, for example, from an article titled "A Comparison of Algorithms for Vertex Normal Computation" by Shuangshuang Jin, Robert R. Lewis, David West, and published by Washington State University, the content of which is incorporated herein by reference in its entirety.

Thus, with continued reference to FIG. 10, the first constrained mesh element 902 may be represented by a plurality of constrained vertices 910, at each of which the processor 550 may be configured to determine a respective one of a plurality of constrained vertex normal vectors 912. By the same token, the unconstrained mesh element 903 may be represented by a plurality of unconstrained vertices 911, for each of which the processor 550 may be configured to determine a respective one of a plurality of unconstrained vertex normal vectors 913.

Further, as can be appreciated from FIG. 10, a given constrained vertex 904 is adjacent to a given unconstrained vertex 905 within the plurality of mesh elements 806. In turn, the given constrained vertex 904 is associated with a given constrained vertex normal vector 914, and the given unconstrained vertex 905 is associated with a given unconstrained vertex normal vector 915. Thus, by determining an angular difference 916, θ, within the coordinate system 805, between the given constrained vertex normal vector 914 and the unconstrained vertex normal vector 915, the processor 550 may be configured to determine the degree of smoothness between the first constrained mesh element 902 and the unconstrained mesh element 903.

For example, the processor 550 may be configured to compare the angular difference 916 to a predetermined angular difference threshold value, such that: (1) in response to the angular difference 916 being equal to or below the predetermined angular difference threshold value, the processor 550 may be configured to identify the unconstrained mesh element 903 as being smooth with respect to the first constrained mesh element 902, thereby including the unconstrained mesh element in the plurality of confirmed constrained mesh elements 920; or (2) in response to the angular difference 916 being greater than the predetermined angular difference threshold value, the processor 550 may further be configured to identify the given unconstrained vertex 905 as a point of discontinuity of smoothness between the first constrained mesh element 902 and the unconstrained mesh element 903, thereby rejecting it from the plurality of confirmed constrained mesh elements 920. Accordingly, in the latter case, the rejecting the unconstrained mesh element 903 from inclusion thereof in the plurality of confirmed constrained mesh elements 920 would result in forming a gap in the augmented crown 3D representation 1020 of the crown portion 26.

In some non-limiting embodiments of the present technology, the predetermined angular difference threshold value can be determined based on experimental data. For example, the predetermined angular difference threshold value can be determined based on a particular configuration of the crown portion 26 and/or a desired level of smoothness of the augmented crown 3D representation 1020 thereof. In a specific example, the predetermined angular difference threshold value may be selected from an interval from 0 to 10 degrees, or from 10 to 20 degrees.

As the given unconstrained vertex 905 may be adjacent to other constrained vertices (not separately labelled), such as those, respectively defining a second constrained mesh element 906 and a third constrained mesh element 908, in other non-limiting embodiments of the present technology, the processor 550 may be configured to examine each of constrained vertex normal vectors associated therewith with respect to the given unconstrained vertex normal vector 915 as described hereinabove. To that end, the processor 550 may be configured to include the unconstrained mesh element 903 in the plurality of confirmed constrained mesh elements 920 based on a number of the associated constrained vertex normal vectors, with which a respective angular difference between the given unconstrained vertex normal vector 915 is equal to or below than the predetermined angular difference threshold value. For example, the processor 550 may be configured to allow the unconstrained mesh element 903 if at least two adjacent constrained vertex normal vectors associated with the first constrained mesh element 902, the second constrained mesh element 906, and the third constrained mesh element 908 form a respective angular difference with the given unconstrained vertex normal vector 915 which is equal to or below the predetermined angular difference threshold value. Conversely, the processor 550 may be configured to reject the unconstrained mesh element 903 from inclusion in the plurality of confirmed constrained mesh elements 920 if the at least two adjacent constrained vertex normal vectors associated with the first constrained mesh element 902, the second constrained mesh element 906, and the third constrained mesh element 908 form the respective angular difference with the given unconstrained vertex normal vector 915 which is greater than the predetermined angular difference threshold value.

In yet other non-limiting embodiments of the present technology, to make such determination, the processor 550 may further be configured to consider a maximum one of respective angular differences formed by one of the first constrained mesh element 902, the second constrained mesh element 906, and the third constrained mesh element 908 with the given unconstrained vertex normal vector 915, as an example.

In certain non-limiting embodiments of the present technology, the processor 550 may be configured to determine if the unconstrained mesh element 903 is to be included in the plurality of confirmed constrained mesh elements for further processing or rejected by applying an Expectation Maximization (EM) algorithm. To that end, the processor 550 may be configured to predetermine initial statistical parameters, such as means and variances, for example, of respective distributions of constrained vertices within the plurality of constrained mesh elements 810 and unconstrained vertices within the plurality of unconstrained mesh elements 812. In specific non-limiting embodiments of the present technology, the processor 550 may be configured to predetermine the initial statistical parameters by using a Machine Learning Algorithm (MLA) having been specifically trained for determining statistical parameters of distribution of vertices within associated pluralities of mesh elements.

In this regard, by using the EM algorithm, the processor 550 may be configured to determine a likelihood value that the given unconstrained vertex 905 and the unconstrained mesh element 903 defined thereby forms part of either (i) the augmented crown 3D representation 1020 of the crown portion 26, and thus should be included in the plurality of confirmed constrained mesh elements 920, or (ii) the image artefacts 700, and thus should be rejected.

Thus, according to certain non-limiting embodiments of the present technology, iteratively identifying, from the plurality of unconstrained mesh elements 812, those associated with the image artefacts 700 and rejecting them, the processor 550 may be configured to generate a refined crown 3D representation of the crown portion 26.

Figure 11:
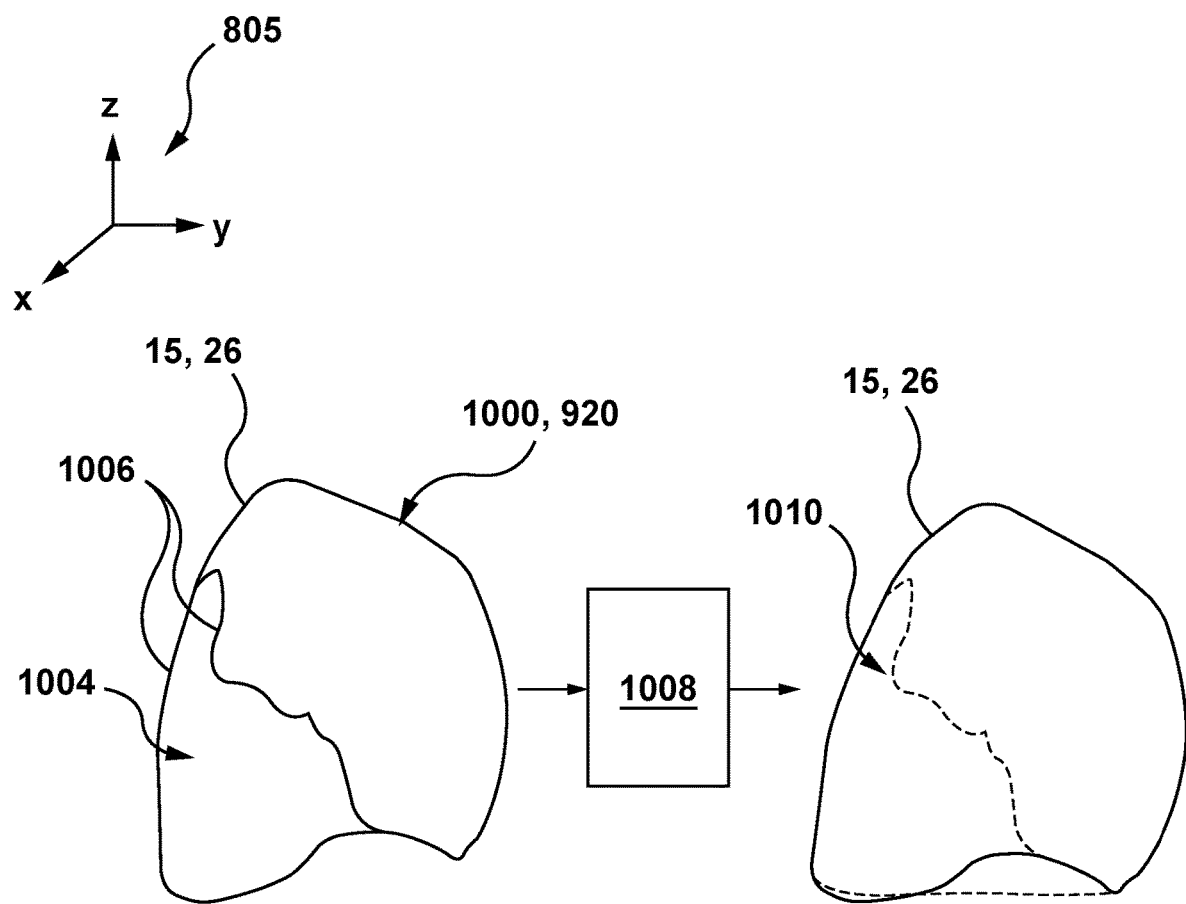
FIG. 11 depicts a schematic diagram of a step in the method of FIG. 8, executed by the processor of FIG. 5, for smoothing, using a Harmonic function, a surface of the refined crow 3D representation of FIG. 10 to generate the augmented crown 3D representation associated with the given one of the plurality of teeth present in FIG. 1, in accordance with certain non-limiting embodiments of the present technology.

With reference to FIG. 11, there is depicted a schematic diagram of a refined crown 3D representation 1000 of the crown portion 26 generated by excluding the image artefacts 700 from the raw crown 3D representation 800, in accordance with certain non-limiting embodiments of the present technology.

As mentioned earlier with reference to FIGS. 9 and 10, determining, by the processor 550, the plurality of confirmed constrained mesh elements 920 representative of the refined crown 3D representation 1000 by rejecting therefrom those of the plurality of unconstrained mesh elements 812 representative of the image artefacts 700, may form gaps in the refined crown 3D representation 1000.

Thus, with reference to FIG. 11, according to certain non-limiting embodiments of the present technology, the processor 550 may be configured to smooth a surface of the refined crown 3D representation 1000 filling in gaps 1004, thereby generating the augmented crown 3D representation 1020 of the crown portion 26.

To that end, according to specific non-limiting embodiments of the present technology, the processor 550 may be configured to apply one or more Harmonic functions 1008 to the refined crown 3D representation 1000 of the crown portion 26, thereby restoring a smooth surface 1010 within the gaps 1004.

In the context of the present specification, the term "Harmonic function" relates to the field of mathematical physics and denotes a function that satisfies Laplace's equation. Accordingly, applying the one or more Harmonic functions 1008 for restoring the smooth surface 1010 within the gaps 1004 may be associated with setting certain boundary conditions.

Thus, according to some non-limiting embodiments of the present technology, the boundary conditions for the one or more Harmonic functions 1008 may comprise vertex coordinates and respective vertex normal vectors (not separately depicted in FIG. 11) defined at respective vertices of those of the plurality of confirmed mesh elements 1002, which are located at a boundary 1006 of the refined crown 3D representation 1000. By doing so, the processor 550, using the one or more Harmonic functions 1008, can be said to be configured to "propagate" smoothness of the refined crown 3D representation 1000 to the augmented crown 3D representation 1020 of the crown portion 26, in a sense, "patching" the gaps 1004 with the smooth surface 1010.

Additionally, according to certain non-limiting embodiments of the present technology, after restoring the smooth surface 1010 within the refined crown 3D representation 1000 of the crown portion 26, the processor 550 may be configured to redefine mesh elements associated with the augmented crown 3D representation 1020 generating a plurality of augmented crown mesh elements 1022. According to some non-limiting embodiments of the present technology, the plurality of augmented crown mesh elements 1022 may be generated in such a way that vertices thereof (not separately depicted) are distributed therewithin substantially uniformly.

Thus, according to certain non-limiting embodiments of the present technology, the augmented crown 3D representation 1020 of the crown portion 26, not including any digital garbage (that is, the image artefacts 700) may further be used, by the processor 550, for a more accurate modelling of the movements of the tooth 15 when determining the orthodontic treatment.

The method 100 hence advances to step 106.

Step 106: Causing Display of the Augmented 3D Representation of the Given Tooth Based on the Set of Confirmed Constrained Vertices.

Figure 12:
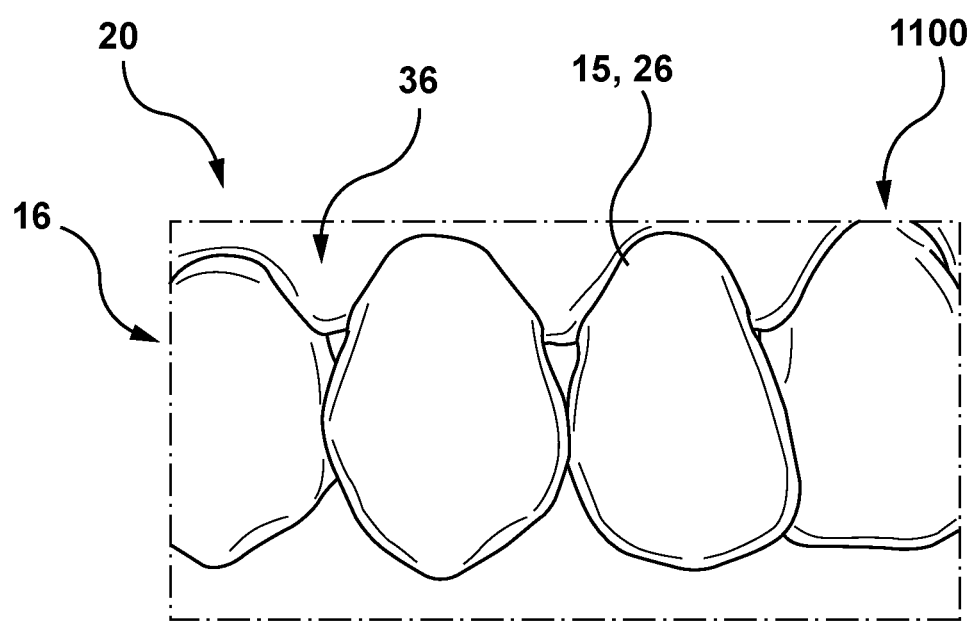
FIG. 12 depicts the portion of the 3D model of FIG. 7 with the digital garbage removed, in accordance with certain non-limiting embodiments of the present technology.

With reference to FIG. 12, at step 106, having applied the method 100 for identifying and eliminating the image artefacts 700 between all tooth 3D representations of the upper teeth 16 in the 3D model 600, the processor 550 may further be configured to generate an augmented 3D model 1100 of the upper arch form 20, in accordance with certain non-limiting embodiments of the present technology. As it can be appreciated, the augmented 3D model 1100 of the upper arch form 20 does not include the image artefacts 700 in the interdental spaces between respective tooth 3D representations of the upper teeth 16 clearly depicting a contour of each crown portion thereof (such as the crown portion 26 of the tooth 15).

Accordingly, in these embodiments, the processor 550 may be configured to determine, based on the augmented 3D model 1100 of the upper arch from 20, the orthodontic treatment for the subject by modelling respective movements of each of the upper teeth 16 in an aggregate fashion, which may allow, for example, for more accurate and effective detection and avoidance of potential collisions between the associated crown portions of the upper teeth 16 in the course of the orthodontic treatment. Further, the processor 550 may be configured to output the augmented 3D model 1100 in the screen 422 of the computer system 410 for professional control of the so determined orthodontic treatment by the practitioner, as an example.

Needless to say that, in other non-limiting embodiments of the present technology, the processor 550 may be configured to apply the same method as described above, mutatis mutandis, within the 3D model 600, to tooth representations of the lower teeth 27, thereby generating an augmented 3D model (not separately depicted) of the lower arch form 21 of the subject for subsequent generation of an orthodontic treatment therefor.

In other non-limiting embodiments of the present technology, the augmented crown 3D representation 1020 of the crown portion 26 so segmented from the 3D model 600 may further be used, by the processor 550, for reconstructing the root 3D representation 1620 of the root portion 28 of the tooth 15. This may further allow, for example, for detection and avoidance of potential collisions of the root portion 28 with root portions of the adjacent teeth or damages to the upper gingiva 36, for example, as will be described immediately below.

Thus, certain embodiments of the method 100 allow for more efficient and accurate reconstruction of a 3D representation of the crown portion 26 of the tooth 15 (such as the augmented crown 3D representation 1020) using raw image data indicative thereof provided by a conventional intraoral scanner, without the need for acquiring and further merging additional image data generated by methods of CT- and/or MR-imaging. Accordingly, such an approach allows for a more accurate modelling of the tooth movements of the tooth 15 in the course of the planned orthodontic treatment considering the movements the crown portion 26 relative to crown portions of the respective ones of the upper teeth 16 at an expected level of accuracy. In certain embodiments, this allows developing safer and more effective orthodontic treatments with limited computational resources and inaccessibility of additional image data.

The method 100 hence terminates.

Root Portion Reconstruction

As alluded to above, according to certain non-limiting embodiments of the present technology, the processor 550 may be configured to use the augmented crown 3D representation 1020 of the crown portion 26 generated in accordance with the method 100 to generate the root 3D representation 1620 of the root portion 28; further merge the augmented crown 3D representation 1020 with the root 3D representation 1620, thereby generating the tooth 3D representation 1720 of the tooth 15. The tooth 3D representation 1720 of the tooth 15 may hence be used for a more accurate planning of the orthodontic treatment allowing taking into account spatial positions of the root portion 28 within the upper gingiva 36, which may further enable avoiding possible collisions thereof with root portions with other of the upper teeth 16 and damage to the upper gingiva 36, whether permanent or not.

Figure 13:
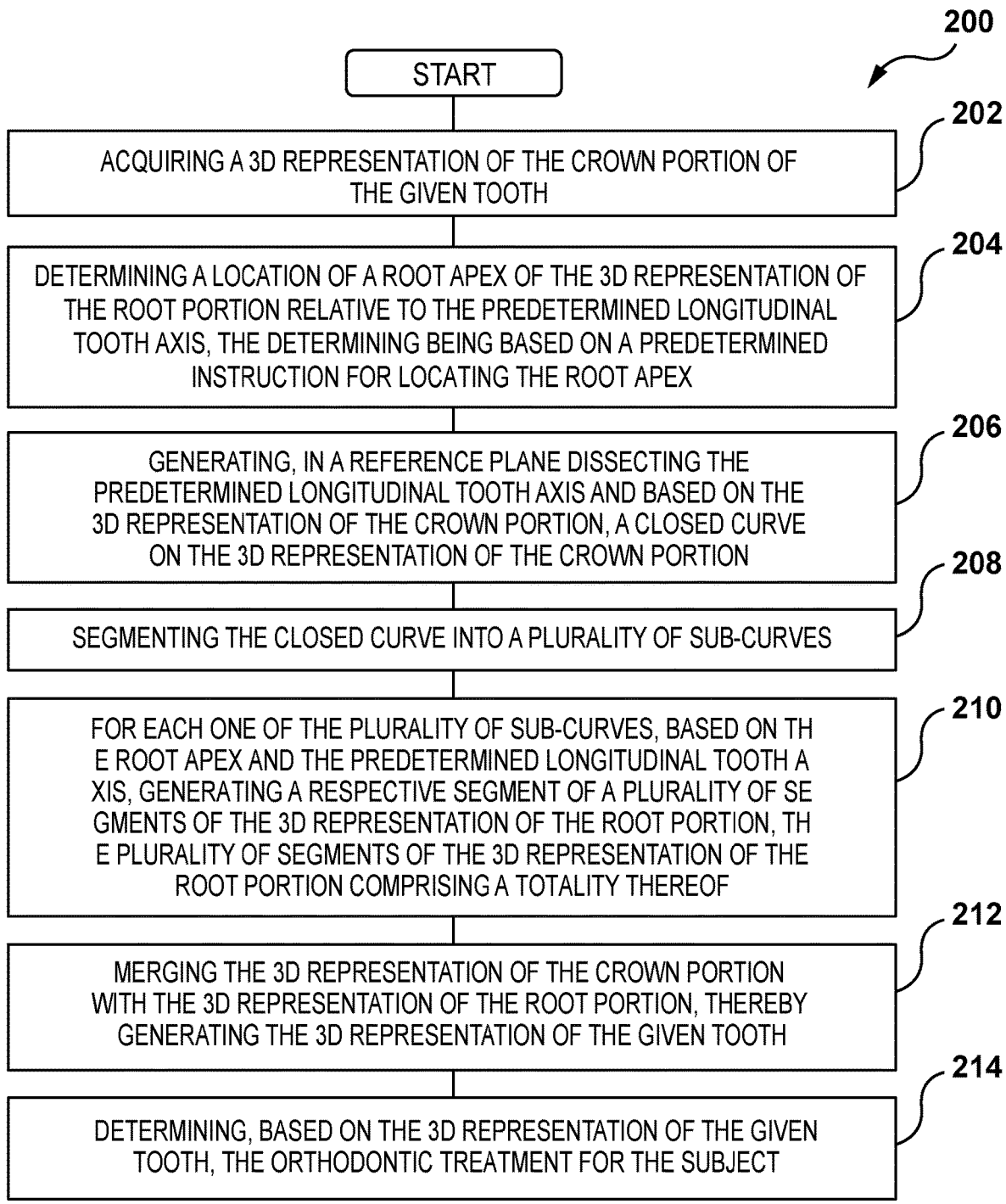
FIG. 13 depicts a flowchart diagram of a method for reconstructing, by the processor of FIG. 5, a root 3D representation of a root portion of the given one of the plurality of teeth present in FIG. 1, in accordance with certain non-limiting embodiments of the present technology.

To that end, according to some non-limiting embodiments of the present technology, the processor 550 may be configured to execute a method 200 for reconstructing a root 3D representation of a root portion associated with the tooth 15 (such as the root 3D representation 1620 of the root portion 28), a flowchart diagram of which is depicted in FIG. 13.

Step 202: Acquiring a 3D Representation of the Crown Portion of the Given Tooth At step 202, according to some non-limiting embodiments of the present technology, the processor 550 may be configured to acquire a 3D crown representation associated with the tooth 15, such as the augmented crown 3D representation 1020 of the crown portion 26.

Further, according to certain non-limiting embodiments of the present technology, the processor 550 may be configured to acquire reference data of the tooth 15. In these non-limiting embodiments, the reference data of the tooth 15 may comprise, without limitation, at least one of a number of root branches of the root portion 28; approximate overall dimensions of the tooth 15 including those of the crown portion 26 and of the root portion 28. To that end, the approximate overall dimensions for the tooth 15 may comprise respective dimensions of the tooth 15 averaged over a sample of subjects, and variations thereof within the sample, as an example.

Figure 14:
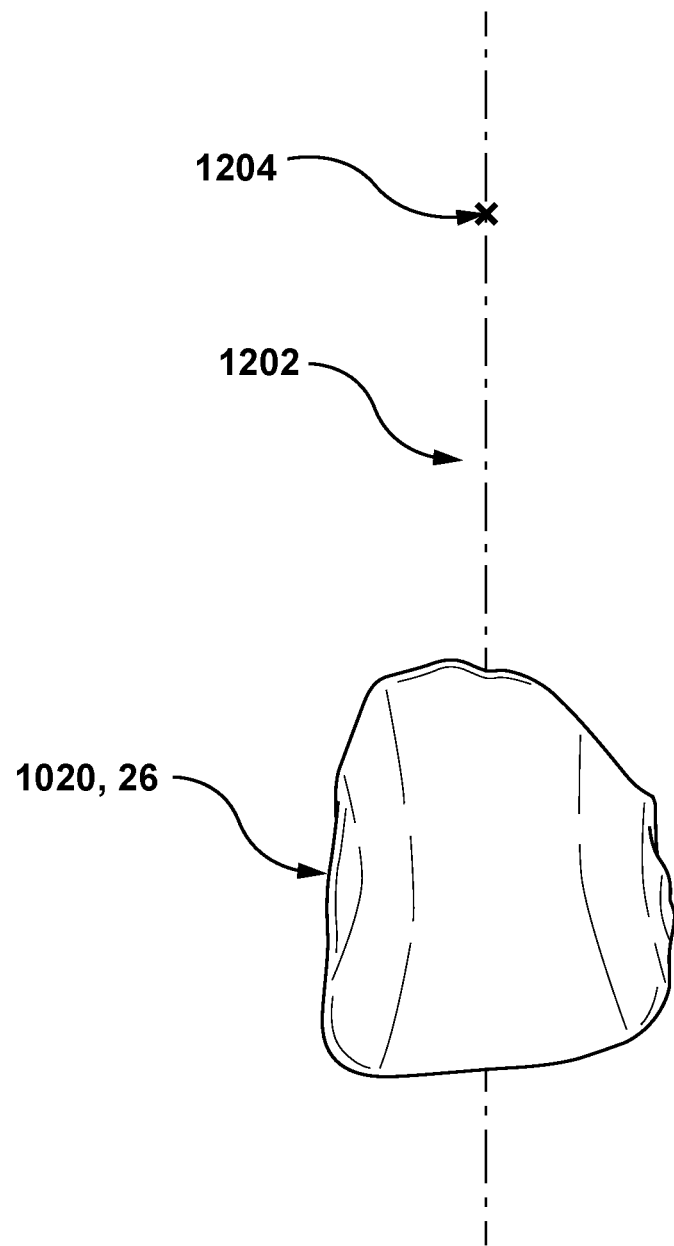
FIG. 14 depicts the augmented crown 3D representation of FIG. 11 used by the processor of FIG. 5 for reconstructing the root 3D representation of the root portion associated with the given one of the plurality of teeth present in FIG. 1, in accordance with certain non-limiting embodiments of the present technology.

With reference to FIG. 14, there is depicted a schematic diagram of the augmented crown 3D representation 1020 used by the processor 550 to reconstruct the root 3D representation 1620 of the root portion 28, in accordance with certain non-limiting embodiments of the present technology.

Certain non-limiting embodiments of the present technology are based on a premise that the augmented crown 3D representation 1020 may be pre-associated with a longitudinal tooth axis 1202 defining a direction for generating the root 3D representation. In some non-limiting embodiments of the present technology, the longitudinal tooth axis 1202 may be predetermined, by the processor 550, based on data indicative of specific anatomical features of crown portion 26 which includes, without being limited to: lobes, developmental grooves, and marginal ridges, as an example. In these embodiments, the data indicative of the specific anatomical features of the crown portion 26 may be part of the reference data indicative of the tooth 15 and include data of spatial positions and dimensions of at least some of the above-listed anatomical features of the crown portion 26 averaged over the sample of subjects.

In specific non-limiting embodiments of the present technology, the longitudinal tooth axis 1202 may be a central tooth axis associated with the tooth 15 having been determined, by the processor 550, based on the augmented crown 3D representation 1020 as described in a co-owned U.S. patent application Ser. No. 16/877,972, entitled "SYSTEMS AND METHODS FOR DETERMINING TOOTH CENTER OF RESISTANCE", the content of which is hereby incorporated by reference in its entirety.

The method 200 hence advances to step 204.

Step 204: Determining a Location of a Root Apex of the 3D Representation of the Root Portion Relative to the Predetermined Longitudinal Tooth Axis, the Determining being Based on a Predetermined Instruction for Locating the Root Apex With continued reference to FIG. 14, at step 204, according to certain non-limiting embodiments of the present technology, based on the reference data of the tooth 15, the processor 550 may be configured to determine, along the longitudinal tooth axis 1202, a location of a root apex 1204 of the root 3D representation of the root portion 28.

The method advances to step 206.

Step 206: Generating, in a Reference Plane Dissecting the Predetermined Longitudinal Tooth Axis and Based on the 3D Representation of the Crown Portion, a Closed Curve on the 3D Representation of the Crown Portion According to some non-limiting embodiments of the present technology, the processor 550 may be configured to reconstruct the root 3D representation 1620 based on curvature features of the augmented crown 3D representation 1020 of the crown portion 26. To that end, to acquire certain data of the curvature of the augmented crown 3D representation 1020, at step 206, the processor 550 may be configured to construct a closed curve around it.

Figure 15:
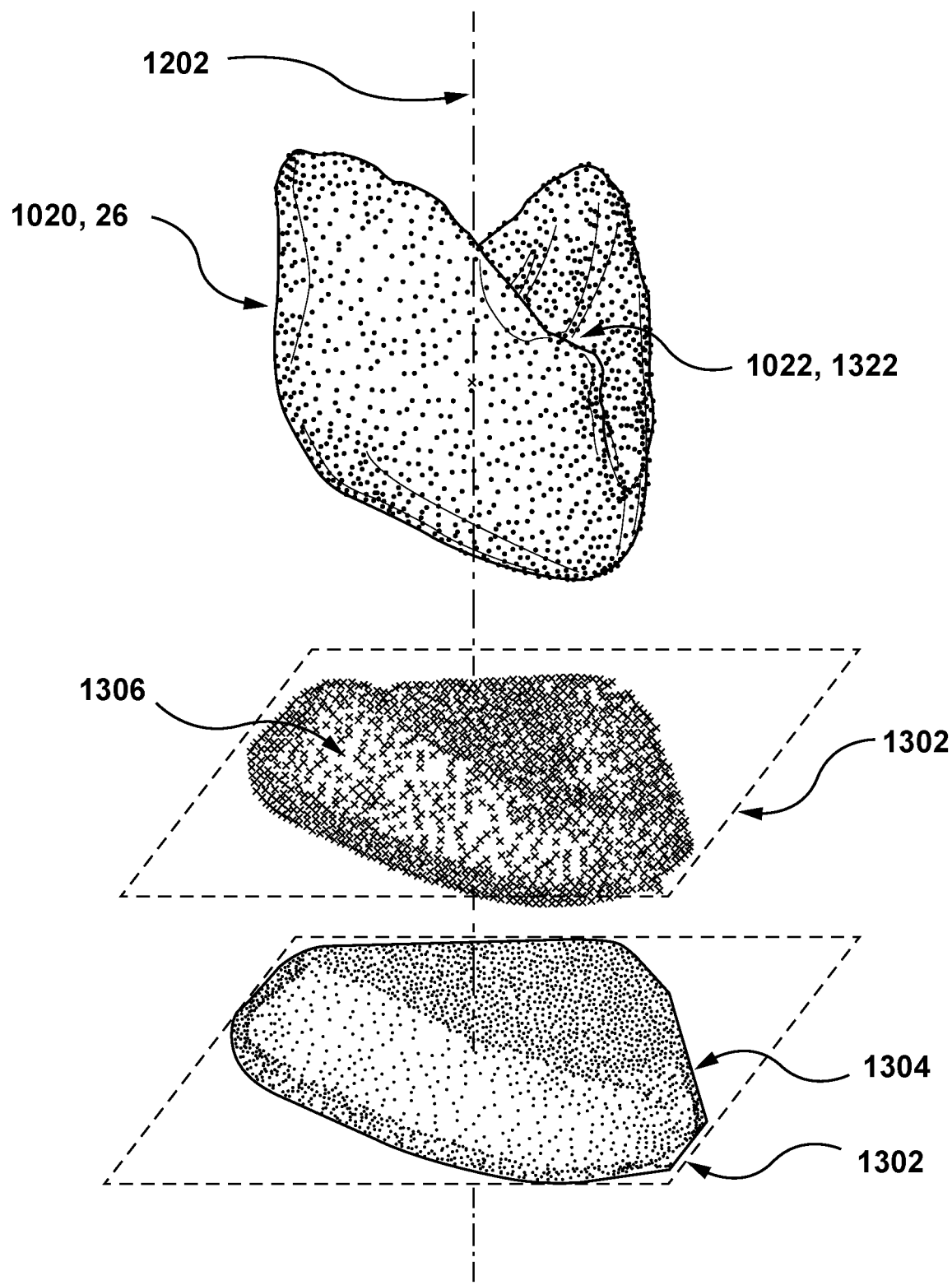
FIGS. 15 and 16 depict schematic diagrams of steps of the method of FIG. 13, executed by the processor of FIG. 5, for generating a closed curve forming a border between the augmented crown 3D representation of FIG. 11 and the root 3D representation, in accordance with certain non-limiting embodiments of the present technology.

With reference to FIG. 15, there is depicted a schematic diagram of executing, by the processor 550, the step 206 of the method 200 to construct a closed curve 1304 around the augmented crown 3D representation 1020 of the crown portion 26, in accordance with certain non-limiting embodiments of the present technology.

According to some non-limiting embodiments of the present technology, the processor 550 may be configured to construct the closed curve 1304 in a horizontal reference plane 1302 intersecting the longitudinal tooth axis 1202. How the horizontal reference plane 1302 may be defined is not particularly limited and may, for example, be defined as being perpendicular to the longitudinal tooth axis 1202. However, other spatial positions of the horizontal reference plane 1302 may also be envisioned by one of skill in the art. For example, the horizontal reference plane 1302 may be defined as extending through points of the augmented crown 3D representation 1020 indicative of contact regions of the tooth 15 with other ones of the upper teeth 16 adjacent thereto, or as being parallel to such a plane.

As previously mentioned, in some non-limiting embodiments of the present technology, the augmented crown 3D representation 1020 may be represented by the plurality of augmented crown mesh elements 1022, wherein each mesh element is defined by respective vertices of a plurality of crown vertices 1322. Thus, in some non-limiting embodiments of the present technology, the processor 550 may be configured to project each one of the plurality of crown vertices 1322 onto the horizontal reference plane 1302, thereby generating a set of projected vertices 1306.

Further, in some non-limiting embodiments of the present technology, the processor 550 may be configured to determine the closed curve 1304 as extending through those of the set of projected vertices 1306 located at the boundary thereof. In other words, the closed curve 1304 may comprise those points from the set of projected vertices 1306 having most distant locations from the longitudinal tooth axis 1304.

Additionally, in some non-limiting embodiments of the present technology, the processor 550 may further be configured to smooth the closed curve 1304. To that end, the processor 550 may be configured to execute one or more smoothing algorithms, which may include, without being limited to: a kernel smoothing algorithm (such as an exponential kernel algorithm, for example), a polynomial smoothing algorithm, a Bezier smoothing algorithm, and the like.

Figure 16:
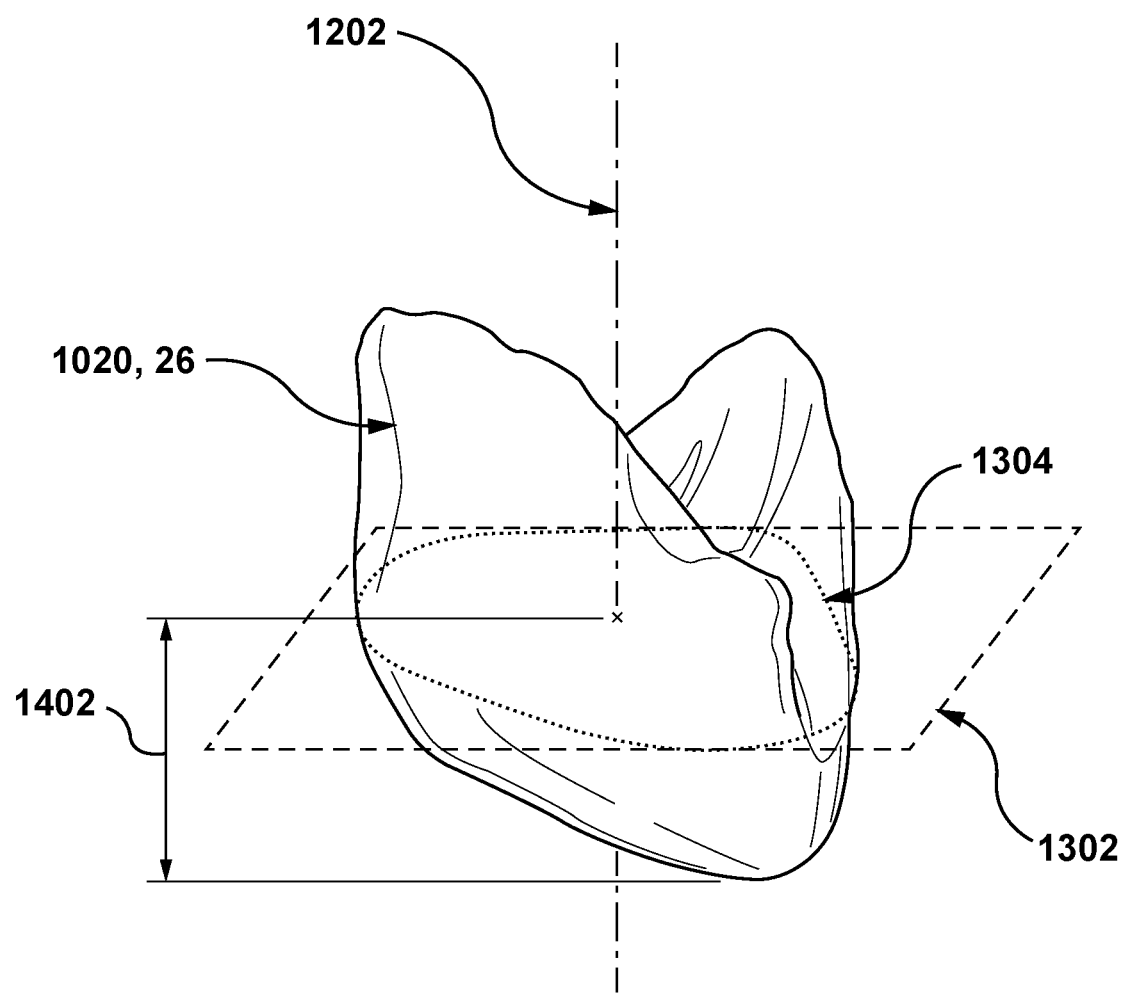

Finally, the processor 550 may be configured to translate the horizontal reference plane 1302 containing the closed curve 1304 along the longitudinal tooth axis 1202 to a predetermined height level 1402 of the augmented crown 3D representation 1020, as depicted in FIG. 16, in accordance with some non-limiting embodiments of the present technology. In some non-limiting embodiments of the present technology, the predetermined height level may comprise a half of a height of the augmented crown 3D representation 1020 of the crown portion 26. However, in other non-limiting embodiments of the present technology, the predetermined height level 1402 may be determined based on coefficients other than 0.5 applied to the height of the augmented crown 3D representation 1020, such as 0.3, 0.4, 0.6, or 0.7, as being optimal for a particular implementation of the present technology.

How a height of the augmented crown 3D representation 1020 for executing such translation is determined is not limited, and may be determined, for example, in accordance with one of the techniques described in the co-owned U.S. patent application Ser. No. 16/877,972.

By doing so, the processor 550 may be configured to construct the closed curve 1304 around the augmented crown 3D representation 1020, points of which may be located either directly on a surface of the augmented crown 3D representation 1020 or beyond it. Thus, the closed curve 1304 may be said to be indicative of curvature of the augmented crown 3D representation 1020 at its overall dimensions along the longitudinal tooth axis 1202. Further, as it can be appreciated, the closed curve 1304 so positioned along the longitudinal tooth axis 1202 may be said to define a boundary between the augmented crown 3D representation 1020 and the root 3D representation 1620 within the tooth 3D representation 1720 to be further constructed by the processor 550.

The method 200 hence advances to step 208.

Step 208: Segmenting the Closed Curve into a Plurality of Sub-Curves

At step 208, according to some none limiting embodiments of then present technology, the processor 550 may be configured to segment the closed curve 1304 into a plurality of sub-curves to form a respective segment of the root 3D representation 1620.

Figure 17A:
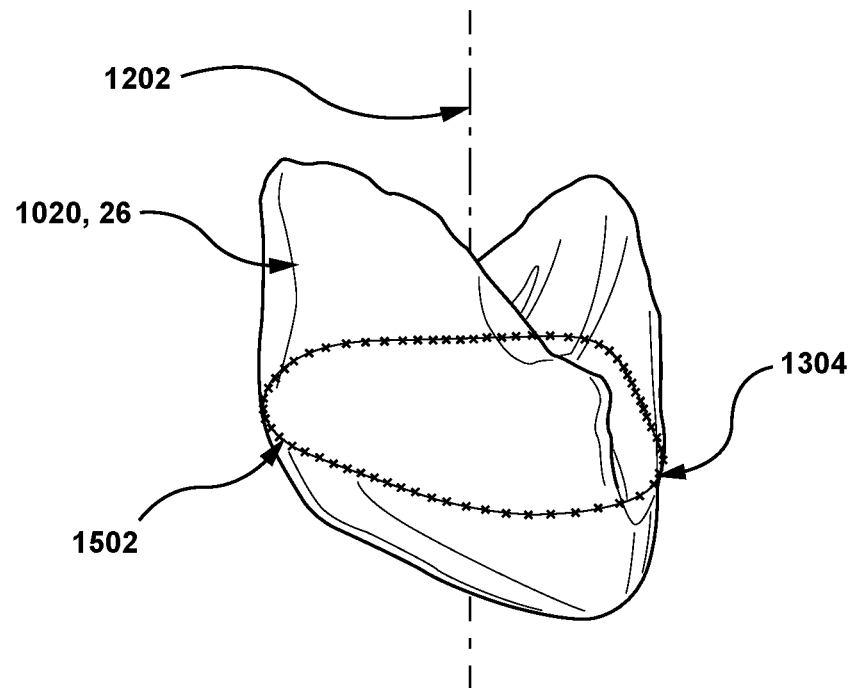
FIGS. 17A and 17B depict schematic diagrams of steps of the method of FIG. 13, executed by the processor of FIG. 5, for segmenting the closed curve of FIG. 16 into a plurality of sub-curves used for generating a respective segment of the root 3D representation, in accordance with certain non-limiting embodiments of the present technology.
Figure 17B:
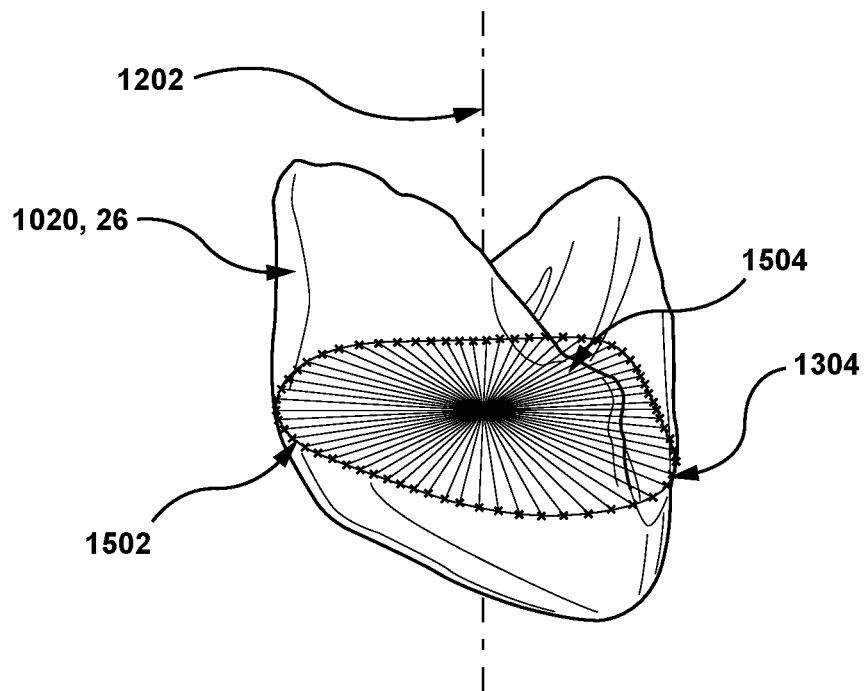

With reference to FIGS. 17A and 17B, there is depicted a schematic diagram of example execution, by the processor 550, of the step 208 for segmenting the closed curve 1304 into a plurality of sub-curves 1502, in accordance with certain non-limiting embodiments of the present technology.

According to some non-limiting embodiments of the present technology, the processor 550 may be configured to generate the plurality of sub-curves 1502 including a predetermined constant number thereof (such as 32 or 64, for example), where each one of the plurality of sub-curves 1502 has an equal length, as depicted in FIG. 17A. However, this might not be the case for implementing each and every non-limiting embodiment of the present technology, and non-equal length sub-curves are possible.

For example, in alternative non-limiting embodiments of the present technology, each one of the plurality of sub-curves 1502 may be generated by the processor 550, to form a same central angle relative to the longitudinal tooth axis 1202 within the closed curve 1304. In other words, in these embodiments, the closed curve 1304 can be said to be segmented into the plurality of sub-curves 1502 by a plurality of lines 1504 originating at a point of an intersection of the longitudinal tooth axis 1202 and the horizontal reference plane 1302 and extending therewithin, where angles between each two consecutive ones of the plurality of lines 1504 are equal, as depicted in FIG. 17B. Further, a number of the plurality of lines 1504 may be selected to segment the closed curve 1304 into the predetermined constant number of sub-curves as mentioned above.

The method 200 hence proceeds to step 210.

Figure 18:
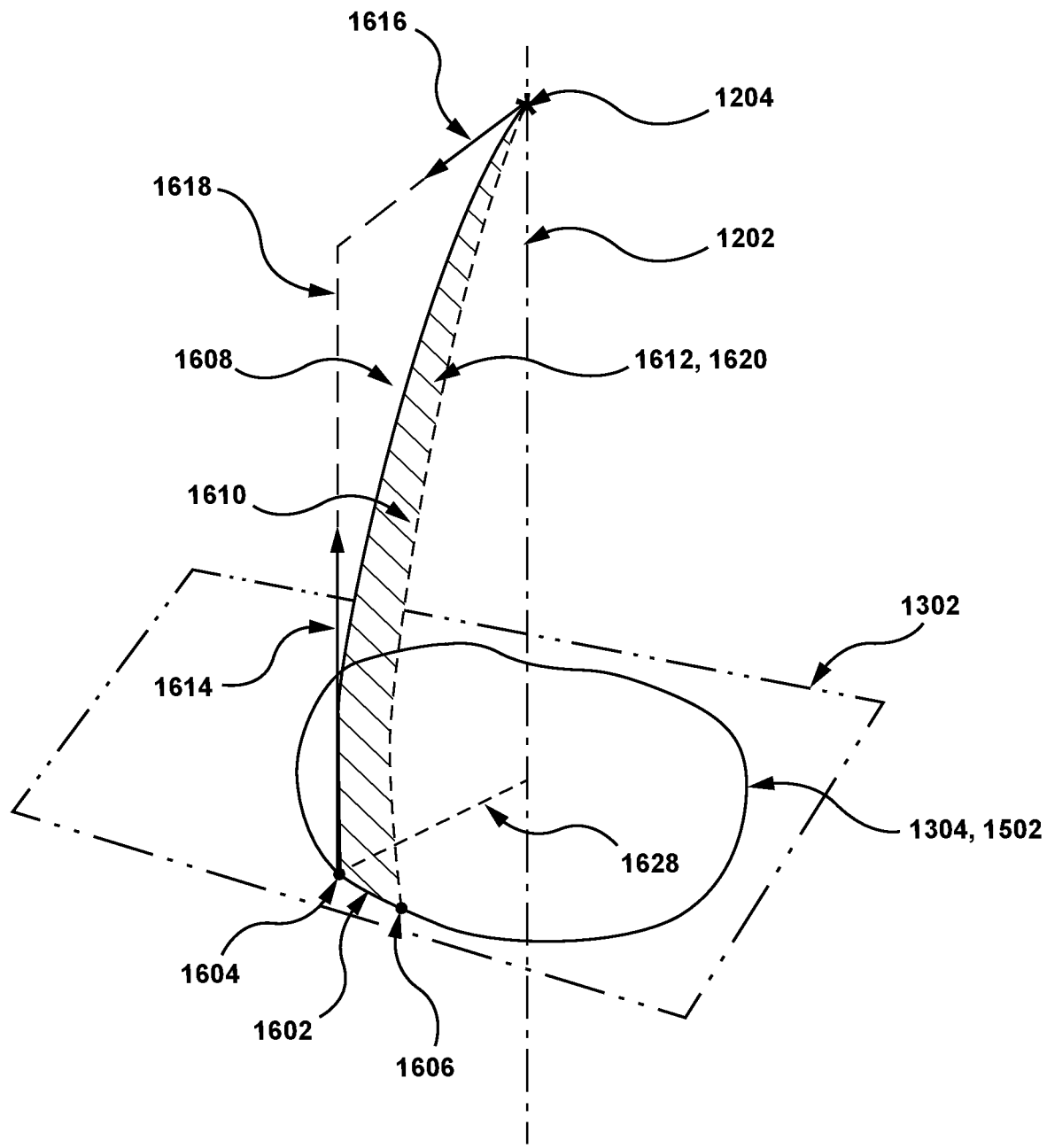
FIG. 18 depicts a schematic diagram of a step of the method of FIG. 13, executed by the processor of FIG. 5, for generating the respective segment of the root 3D representation, in accordance with certain non-limiting embodiments of the present technology.

Step 210: For Each One of the Plurality of Sub-Curves, Based on the Root Apex and the Predetermined Longitudinal Tooth Axis, Generating a Respective Segment of a Plurality of Segments of the 3D Representation of the Root Portion, the Plurality of Segments of the 3D Representation of the Root Portion Comprising a Totality Thereof At step 210, having generated the plurality of sub-curves 1502, the processor 550 may further proceed to generate the root 3D representation 1620. With reference to FIG. 18, there is depicted a schematic diagram of executing, by the processor 550, the step 210 of the method 200 1600 to generate a given segment 1612 of the root 3D representation 1620 based on a given sub-curve 1602 of the plurality of sub-curves 1502, in accordance with certain non-limiting embodiments of the present technology.

First, according to some non-limiting embodiments of the present technology, the processor 550 may be configured to identify a start point 1604 and an end point 1606 of the given sub-curve 1602. Further, the processor 550 may be configured to construct a Bezier curve 1608 extending between the start point 1604 of the given sub-curve 1602 and the root apex 1204.

How the Bezier curve 1608 is defined is not particularly limited; and in some non-limiting embodiments of the present technology, the Bezier curve 1608 may be initialized by a pair of tangent vectors originating in its boundary points—that is, a first tangent vector 1614 originating in the start point 1604 of the given sub-curve 1602, and a second tangent vector 1616 originating in the root apex 1204. In these embodiments, both the first tangent vector 1614 and the second tangent vector 1616 may be predefined to be mutually perpendicular, such that the first tangent vector 1614 may be parallel to the longitudinal tooth axis 1202, and the second tangent vector 1616 may be parallel to the horizontal reference plane 1302 (and thus perpendicular to the longitudinal tooth axis 1202). In turn, respective absolute values of the first tangent vector 1614 and the second tangent vector 1616 may be predetermined based on respective orthogonal distances between the start point 1604 and the root apex 1204. Thus, for example, a first absolute value of the first tangent vector may be a half of a first orthogonal distance 1618; and a second absolute value of the second tangent vector 1616 may be a half of a second orthogonal distance 1628. It should be noted that, in other non-limiting embodiments of the present technology, other coefficients, such as 0.3 or 0.8, may be respectively applied to the first orthogonal distance 1618 and the second orthogonal distance 1628 to determine the absolute values of the first tangent vector 1614 and the second tangent vector 1616.

Further, the processor 550 may be configured to revolve the Bezier curve 1608 about the longitudinal tooth axis 1202 from the start point 1604 to the end point 1606 of the given sub-curve 1602, thereby generating the given segment 1612 of the root 3D representation 1620. Thus, the given segment 1612 can be said to be a segment of a revolution surface formed by revolving the Bezier curve 1608 about the longitudinal tooth axis 1202.

The method 200 hence proceeds to step 212.

Figure 19:
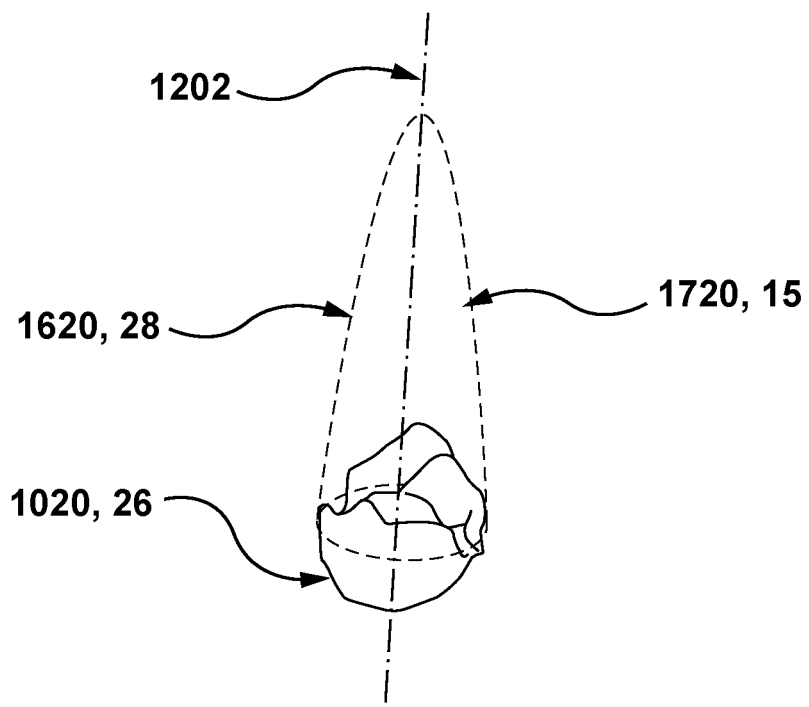
FIG. 19 depicts a schematic diagram of a step of the method of FIG. 13, executed by the processor of FIG. 5, for merging the augmented crown 3D representation of FIG. 11 with the root 3D representation of FIG. 18 for generating a tooth 3D representation of the given one of the plurality of teeth present in FIG. 1, in accordance with certain non-limiting embodiments of the present technology.

Step 212: Merging the 3D Representation of the Crown Portion with the 3D Representation of the Root Portion, Thereby Generating the 3D Representation of the Given Tooth According to certain non-limiting embodiments of the present technology, a totality of segments so generated based on the respective ones of the plurality of sub-curves 1502 may thus form the root 3D representation 1620 of the root portion 28, as depicted in FIG. 19.

Further, at step 212, the processor 550 may be configured to merge the root 3D representation 1620 with the augmented crown 3D representation 1020, thereby generating a tooth 3D representation 1720 of the tooth 15.

The method 200 further proceeds to step 214.

Step 214: Determining, Based on the 3D Representation of the Given Tooth, the Orthodontic Treatment for the Subject At step 214, having applied the method 200, as described above with respect to reconstructing the tooth 3D representation 1720 of the root portion 28 of the tooth 15, to other ones of the upper teeth 16, the processor 550 may further be configured to generate respective root 3D representations therefor, thereby completing the augmented 3D model 1100 (depicted in FIG. 12) of the upper arch form 20. By so doing, in certain non-limiting embodiments of the present technology, the processor 550 may further be configured to generate the orthodontic treatment plan for the subject causing the tooth 15 to move towards the aligned position that would account not only for movements of the crown portion 26, but would also consider spatial positions of the root portion 28 within the upper arch form 20. This may allow for avoidance of collisions between the root portion 28 and root portions of the upper teeth 16 adjacent to the tooth 15 as well as prevent permanent damage to the upper gingiva 36 and other tissues surrounding the tooth 15.

Additionally, the processor 550 may be configured to cause the computer system 410 to display the so generated tooth 3D representations of the upper teeth 16 on the screen 422.

In some non-limiting embodiments of the present technology, before causing display of the tooth 3D representations of the upper teeth 16, the processor 550 may be configured to augment their associated root portions for a more anatomically detailed representation of the upper arch form 20. More specifically, the processor 550 may be configured to replace, within the tooth 3D representation 1720 of the tooth 15, the root 3D representation 1620 of the root portion 28 with an augmented root 3D representation thereof, as will be immediately described below.

Figure 20:
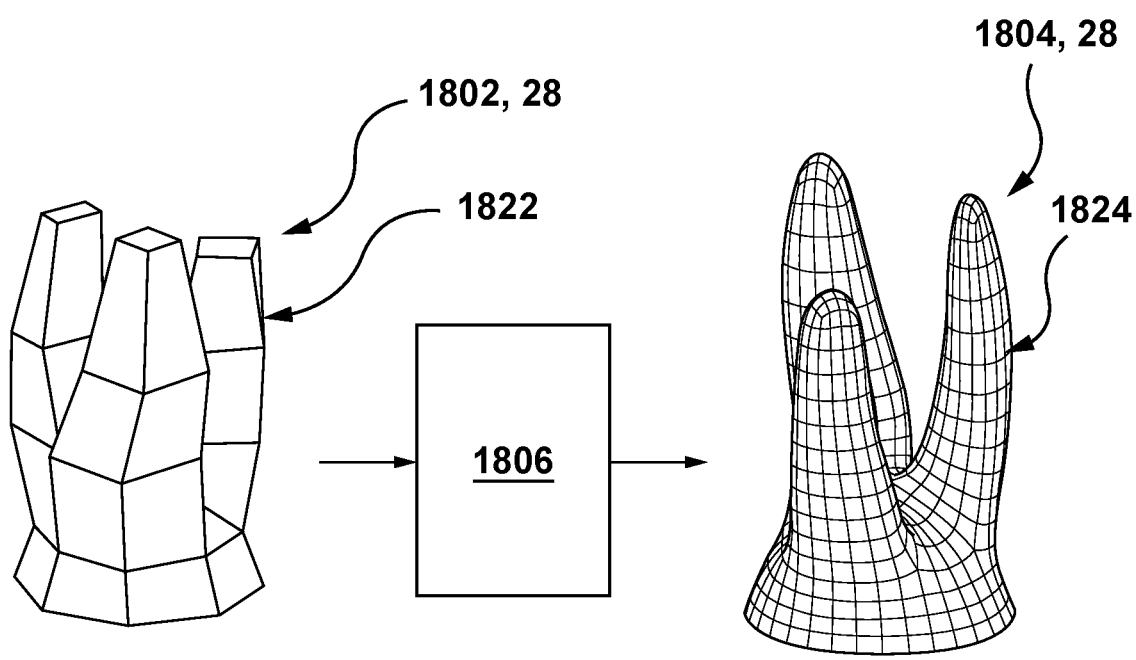
FIG. 20 depicts a base parametric model associated with the root portion of given one of the plurality of teeth present in FIG. 1 and a schematic diagram of smoothing it for augmenting, by the processor of FIG. 5, the root 3D representation of the FIG. 19, in accordance with certain non-limiting embodiments of the present technology.

According to certain non-limiting embodiments of the present technology, the reference data associated with the tooth 15 may further include a base parametric 3D model of the root portion 28. With reference to FIG. 20, there is depicted a base parametric 3D model 1802 for the root portion 28 used, by the processor 550, for generating an augmented root 3D representation 1804 thereof, in accordance with certain non-limiting embodiments of the present technology.

According to certain non-limiting embodiments of the present technology, the base parametric 3D model 1802 may comprise a plurality of coarse root mesh elements 1822 that may further be smoothed, by the processor 550, thereby generating the augmented root 3D representation 1804 of the root portion 28.

In some non-limiting embodiments of the present technology, the smoothing may be based on a subdivision surface algorithm 1806, to which the processor 550 may be provided access. Broadly speaking, the subdivision surface algorithm 1806 may be configured to iteratively subdivide each one of the plurality of coarse root mesh elements 1822 into smaller ones of a plurality of augmented root mesh elements 1824, which is generated to correspond to the plurality of augmented crown mesh elements 1022.

In specific non-limiting embodiments of the present technology, the subdivision surface algorithm 1806 may be a Catmull-Clark subdivision surface algorithm; however, in other non-limiting embodiments of the present technology, the subdivision surface algorithm 1806 may further include a Doo-Sabin subdivision surface algorithm, a Loop subdivision surface algorithm, a Midedge subdivision surface algorithm, and a Kobbelt subdivision surface algorithm, as an example.

According to certain non-limiting embodiments of the present technology, the processor 550 may be configured to recursively apply the subdivision surface algorithm 1806 as long as a distribution of vertices along the plurality of augmented root mesh elements 1824 of the augmented root 3D representation 1804 corresponds to that of vertices of the plurality of augmented crown mesh elements 1022 of the augmented crown 3D representation 1020 depicted in FIG. 11.

It should further be noted that the processor 550 may be configured to verify, at each iteration of applying the subdivision surface algorithm 1806, if dimensions of the augmented root 3D representation 1804 correspond to the approximate overall dimensions of the root portion 28 (such as a length thereof, for example) received as part of the reference data of the tooth 15, and adjust discrepancies therebetween.

Figure 21:
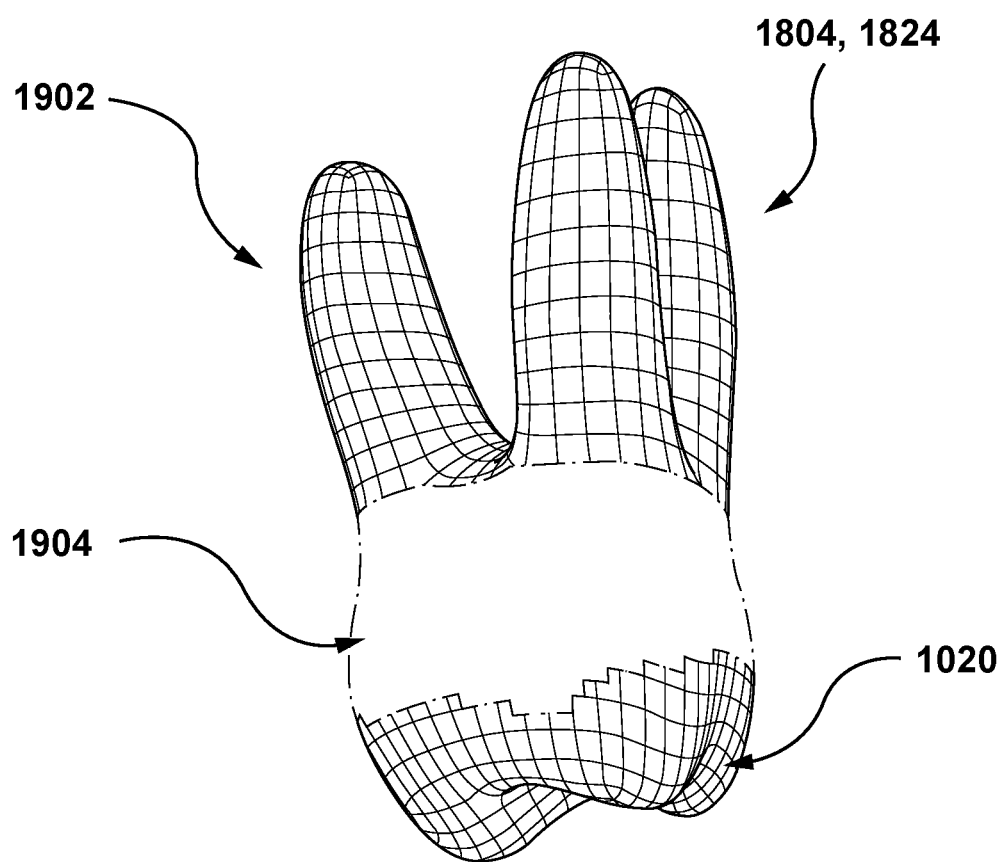
FIG. 21 depicts a schematic diagram of a step of the method of the method of FIG. 13, executed by the processor of FIG. 5, for merging the augmented crown 3D representation of FIG. 11 with the augmented root 3D representation of FIG. 20 to generate an augmented tooth 3D representation associated with the given one of the plurality of teeth present in FIG. 1, in accordance with certain non-limiting embodiments of the present technology.

Further, the processor 550 may be configured to merge the augmented root 3D representation 1804 with the augmented crown 3D representation 1020 generating an augmented tooth 3D representation 1902 depicted in FIG. 21, in accordance with certain non-limiting embodiments of the present technology.

In some non-limiting embodiments of the present technology, the merging the augmented root 3D representation 1804 and the augmented crown 3D representation 1020 may produce an undefined region 1904 that may further be smoothed, by the processor 550, using the one or more Harmonic functions 1008 as described above with reference to FIG. 11.

Thus, the processor 550 may be configured to generate a respective augmented tooth 3D representation for each of the upper teeth 16 and further cause display thereof on the screen 422 of the computer system 410.

Additionally, in some non-limiting embodiments of the present technology, to prevent intersections between the respective augmented tooth 3D representations of the upper teeth 16 and hence generate more realistic interdental spaces therebetween, the processor 550 may be configured to apply a collision detection and prevention method described in a co-owned U.S. patent application Ser. No. 16/703,424 entitled "SYSTEMS AND METHODS FOR DETERMINING ORTHODONTIC TREATMENTS", and filed on Dec. 4, 2019; the content of which is hereby incorporated by reference in its entirety.

Thus, certain embodiments of the method 200 allow for more efficient and accurate reconstruction of a 3D representation of the root portion 28 of the tooth 15 based on a respective 3D representation of the crown portion 26 (such as the augmented crown 3D representation 1020) using image data indicative thereof provided by a conventional intraoral scanner, without the need for acquiring and further merging additional image data generated by methods of CT- and/or MR-imaging. Accordingly, such an approach allows for a more comprehensive modelling of the tooth movements of the tooth 15 in the course of the planned orthodontic treatment considering the movements not only of the crown portion 26 thereof, but also spatial positions of the root portion 28 relative, for example, to other ones of the upper teeth 16 and those within the upper gingiva 36. In certain embodiments, this allows developing safer and more effective orthodontic treatments with limited computational resources and inaccessibility of additional image data.

The method 200 hence terminates.

Finally, to complete the generation of the comprehensive 3D representation of the upper arch form 20 (such as a comprehensive 3D representation 3200 depicted in FIG. 35), after the generating the augmented tooth 3D representation 1902, the processor 550 may further be configured to generate a comprehensive gingiva 3D representation of the upper gingiva 36, as will be described immediately below.

Gingiva Reconstruction

As previously mentioned, for determining a more effective and efficient orthodontic treatment plan, it may be necessary to consider tooth movements of the tooth 15 within the subject's arch form (such as the upper arch form 20) in its entirety. For example, this may be the case when considering movements of the root portion 28 within the upper gingiva 36 during the orthodontic treatment to prevent permanent damage thereof or to tissues related thereto (such as proximal nerve pathways and blood vessels). In another example, more accurate image data of an actual anatomy of the upper gingiva 36 (such as overall dimensions thereof) may allow for a more efficient process for producing the orthodontic appliance 10 (described above with reference to FIGS. 1 and 2), quality of which may be directly connected with the overall quality of the planned orthodontic treatment.

Figure 34:
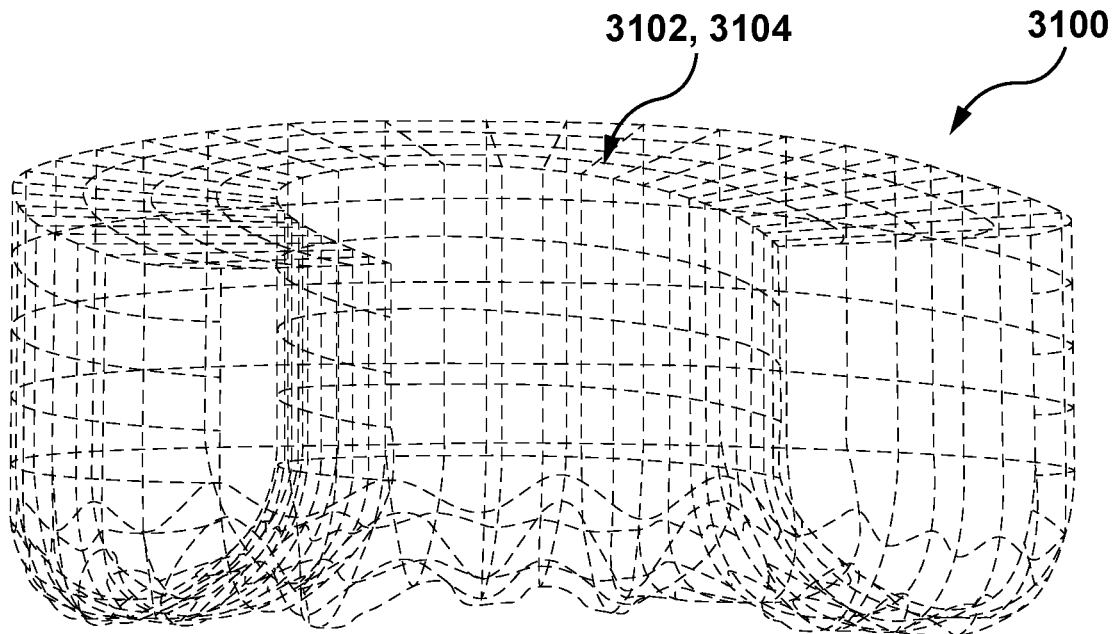
FIG. 34 depicts a base gingiva cage representative of the comprehensive gingiva 3D representation associated with upper arch form of FIG. 2 having been generated by the processor of FIG. 5, by repeatedly applying the steps of FIGS. 32A, 32B, and 33, in accordance with certain non-limiting embodiments of the present technology.

However, intra-oral scanning techniques (such as those described hereinabove in respect of the imaging device 430 of FIG. 4) may not be effective in capturing the comprehensive gingiva 3D representation (such as a comprehensive gingiva 3D representation 3100 depicted in FIGS. 34 and 35) of the upper gingiva 36 as they may be limited only to visually accessible portions thereof, which may not be sufficient for considering the aspects of the orthodontic treatment mentioned above.

Figure 22:
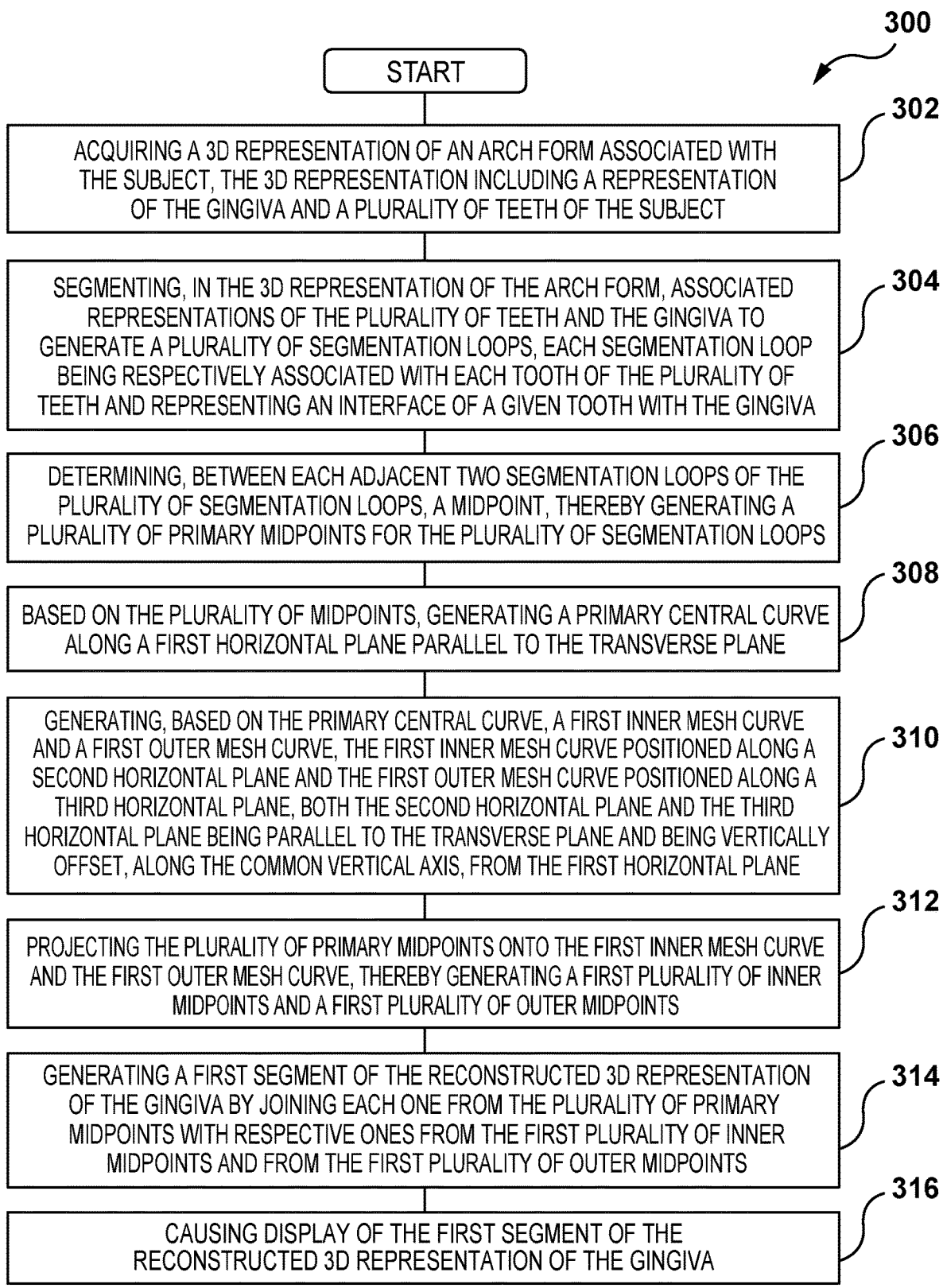
FIG. 22 depicts a flowchart diagram of a method for reconstructing a comprehensive gingiva 3D representation of a gingiva associated with the upper arch form of FIG. 2, in accordance with certain non-limiting embodiments of the present technology.

Thus, according to certain non-limiting embodiments of the present technology, the processor 550 may be configured to execute a method 300 for reconstructing a gingiva 3D representation of the upper gingiva 36 for the upper arch form 20, a flowchart diagram of which is depicted in FIG. 22.

Figure 23:
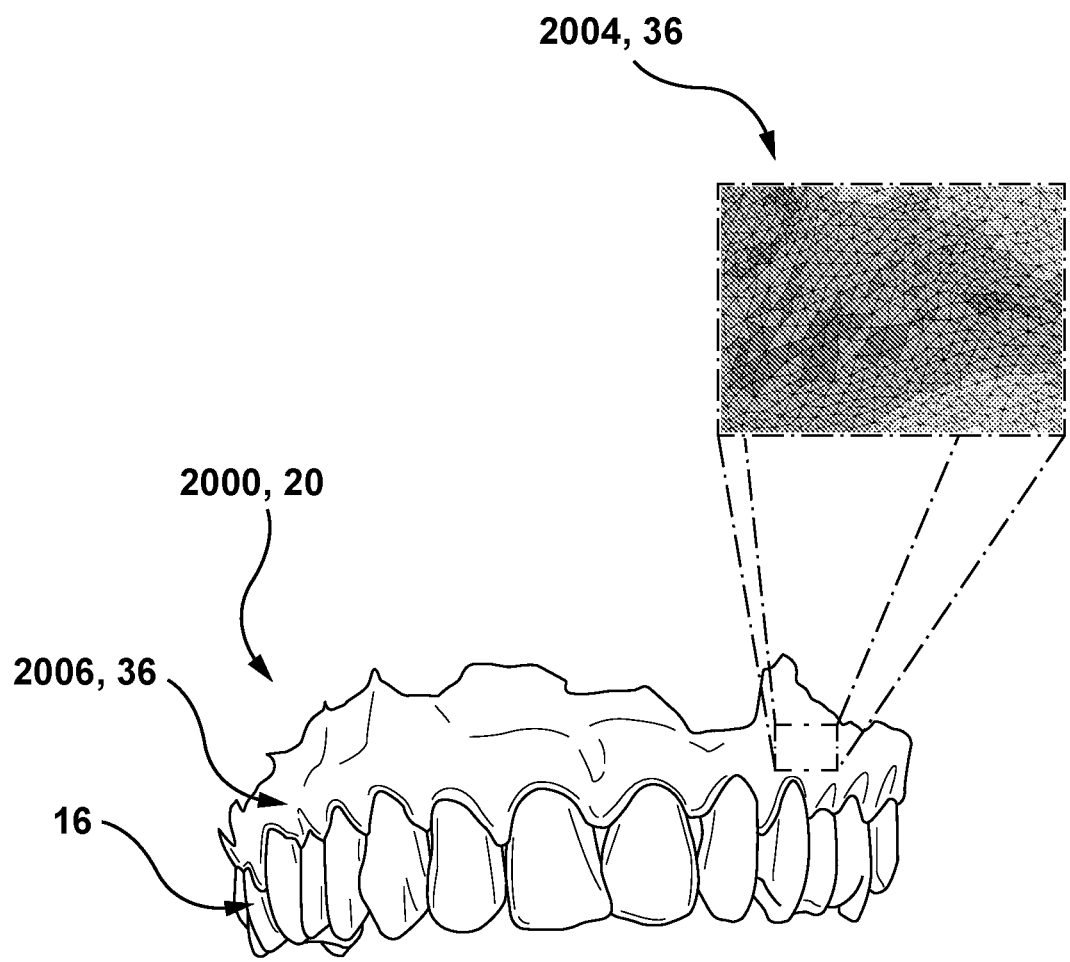
FIG. 23 depicts a portion of the 3D model of FIG. 6 representative of a raw 3D representation of the upper arch form of FIG. 2 used, by the processor of FIG. 5, to generate the comprehensive gingiva 3D representation associated therewith, in accordance with certain non-limiting embodiments of the present technology.

Step 302: Acquiring a 3D Representation of an Arch Form Associated with the Subject, the 3D Representation Including a Representation of the Gingiva and a Plurality of Teeth of the Subject The method 300 commences at step 302 with the processor 550 acquiring a raw 3D representation of the upper arch form 20 of the subject. With reference to FIG. 23, there is depicted a portion of the 3D model 600 of FIG. 6 representative of frontal view of a raw arch form 3D representation 2000 of the upper arch form 20 including a raw gingiva 3D representation 2006 of the upper gingiva 36 received, by the processor 550, from the imaging device 430, in accordance with certain non-limiting embodiments of the present technology.

As it can be appreciated, the raw gingiva 3D representation 2006 has an uneven contour, which may be indicative that a significant portion of the upper gingiva 36 was not accessible to the imaging device 430 for capturing at the moment of generating the raw gingiva 3D representation 2006.

Further, in some non-limiting embodiments of the present technology, the imaging device 430 may be configured to generate the raw gingiva 3D representation 2006 comprising a plurality of raw mesh elements 2004. To that end, the plurality of raw mesh elements 2004 may be chaotically distributed on a surface of the raw gingiva 3D representation 2006, whose coordinates should be determined by the processor 550 for further processing. However, the process for determining these coordinates may be computationally costly, and as a result, this may pose additional challenges to apply textures and colours onto the raw gingiva 3D representation 2006 depicting anatomical features of the upper gingiva 36 for effective visualization thereof on the screen 422 of the computer system 410. Accordingly, this may compromise accuracy of the orthodontic treatment of the upper arch form 20 of the subject.

Thus, certain non-limiting embodiments of the present technology are directed to methods and systems for reconstructing the comprehensive gingiva 3D representation of the upper gingiva 36 used for determining a safer and more effective orthodontic treatment, which will be described immediately below.

Figure 24:
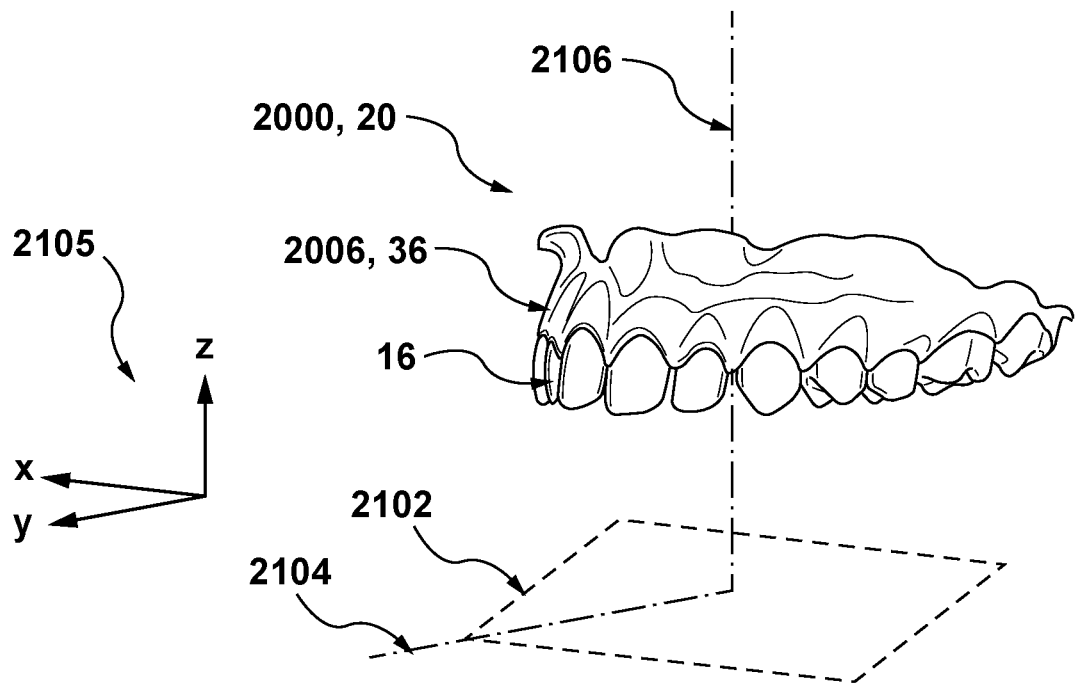
FIG. 24 depicts a schematic diagram of a step of the method of FIG. 22, executed by the processor of FIG. 5, for determining a jaw coordinate system associated with the raw 3D representation of the upper arch form of FIG. 2, in accordance with certain non-limiting embodiments of the present technology.

With reference to FIG. 24, there is depicted a perspective view of the raw arch form 3D representation 2000 of the upper arch form 20, in accordance with certain non-limiting embodiments of the present technology.

According to certain non-limiting embodiments of the present technology, the processor 550 may first be configured to determine a jaw coordinate system 2105 associated with the raw arch form 3D representation 2000. To that end, along the image data indicative of the upper arch form 20, the processor 550 may be configured to receive data indicative of a transverse plane 2102 associated with a subject's skull. In the context of the present disclosure, the term "transverse" plane relates to the field of anatomy of vertebrates (including humans) and denotes an imaginary plane dividing a body into superior and inferior parts. The transverse plane 2102, as referred to herein, is perpendicular to a coronal plane and a sagittal plane associated with the subject's skull. In other non-limiting embodiments of the present technology, the transverse plane 2102 may be a Frankfort horizontal plane associated with the subject's skull.

Further, the processor 550 may be configured to receive data of a common median axis 2104. In the context of the present disclosure, the term "common median axis" is to denote a line extending within the transverse plane 2102 and parallel to an imaginary line extending between either central ones of the upper teeth 16 or central ones of the lower teeth 27 (not separately numbered) of the subject, which may also be referred to herein a midline of the upper arch form 20 or a midline of the lower arch form 21, respectively. Thus, for example, those of the upper teeth 16 located towards the common median axis 2104 may be referred to as mesial teeth; and those of the upper teeth 16 located away from the common median axis may be referred to as distal teeth.

Finally, the processor 550 may be configured to generate a common vertical axis 2106 to be parallel to the common median axis 2104. Thus, the processor 550 may be configured to determine the jaw coordinate system 2105, where an XY plane is parallel to the transverse plane 2102, a Y axis is parallel to the common median axis 2104, and a Z axis is parallel to the common vertical axis 2106.

The method 300 thus proceeds to step 304.

Step 304: Segmenting, in the 3D Representation of the Arch Form, Associated Representations of the Plurality of Teeth and the Gingiva to Generate a Plurality of Segmentation Loops, Each Segmentation Loop being Respectively Associated with Each Tooth of the Plurality of Teeth and Representing an Interface of a Given Tooth with the Gingiva At step 304, according to certain non-limiting embodiments of the present technology, the processor 550 may be configured to isolate the raw gingiva 3D representation 2006 from the raw arch form 3D representation 2000. To that end, the processor 550 may be configured to determine contours of the respective tooth 3D representations of the upper teeth 16 in the raw arch form 3D representation 2000 and remove them therefrom. Thus, in some non-limiting embodiments of the present technology, the processor 550 may be configured to apply a tooth segmentation technique described in the section Automatic Tooth Segmentation of the present document. In other non-limiting embodiments of the present technology, the processor 550 may be configured to apply another automatic tooth segmentation technique, for example, one, which is described in a co-owned U.S. patent application Ser. No. 16/703,471 filed Dec. 4, 2019, entitled "METHOD AND SYSTEM FOR DENTAL BOUNDARY DETERMINATION", the content of which is hereby incorporated by reference in its entirety.

Figure 25:
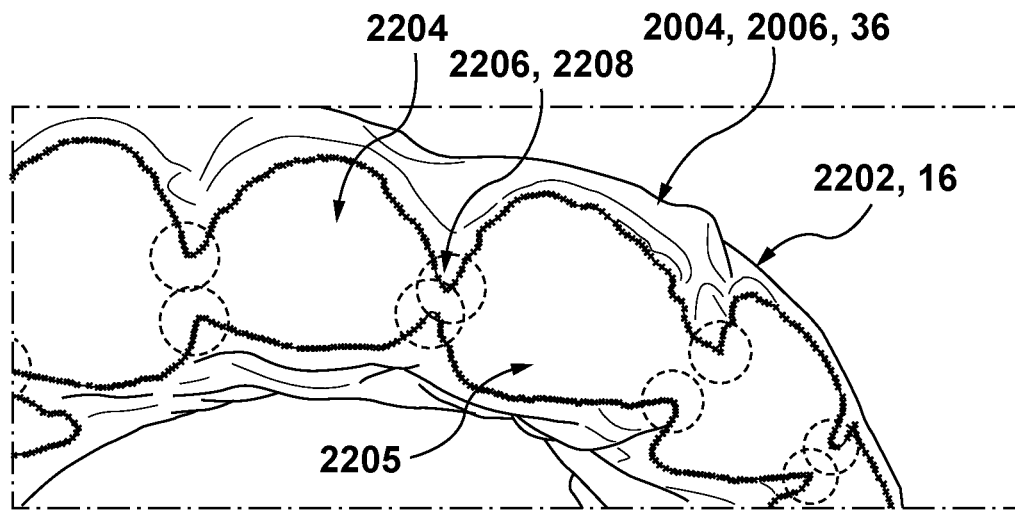
FIGS. 25 to 28 depict schematic diagrams of steps of the method of FIG. 22, executed by the processor of FIG. 5, respectively for generating a plurality of segmentation loops by segmenting 3D tooth representations of the plurality of teeth present in FIG. 1 from the raw 3D representation of FIG. 23, in accordance with certain non-limiting embodiments of the present technology.

With reference to FIG. 25, there is depicted the raw gingiva 3D representation 2006 including a plurality of preliminary segmentation loops 2202 representing interface for upper teeth 16 and generated, by the processor 550, by segmenting the tooth 3D representations of the in the raw arch form 3D representation 2000, in accordance with certain non-limiting embodiments of the present technology.

In some non-limiting embodiments of the present technology, the processor 550 may be configured to filter out those vertices associated with respective ones of the plurality of raw mesh elements 2004 that are located on representations on interdental papillae, between each pair of adjacent ones of the plurality of preliminary segmentation loops 2202. In other words, the processor 550 may be configured to filter out those vertices associated with respective ones of the plurality of raw mesh elements 2004 that are shared between the adjacent ones of the plurality of preliminary segmentation loops 2202.

For example, a first preliminary segmentation loop 2204 is adjacent to a second preliminary segmentation loop 2205, such that both of them are coupled by a representation of a given interdental papilla 2206. To that end, the representation of the given interdental papilla 2206 may include mesh elements of the plurality of raw mesh elements 2004 shared between the first preliminary segmentation loop 2204 and the second preliminary segmentation loop 2205, which the processor 550 may thus be configured to remove.

In some non-limiting embodiments of the present technology, the processor 550 may be configured to remove all mesh elements of the plurality of raw mesh elements 2004 lying within a circle 2208 of a predetermined radius (not separately numbered) defined at a tip of the representation of the given interdental papilla 2206. A length of the predetermined radius may depend, for example, on a particular configuration of the imaging device 430, and, in certain non-limiting embodiments of the present technology, may be 1 mm. However, in other non-limiting embodiments of the present technology, the length of the predetermined radius of the circle 2208 may take other values, such as 0.5 mm, 1.5 mm, or 3 mm, as an example.

Thus, the processor 550 may be configured to remove mesh elements of the plurality of raw mesh elements 2004 lying on the respective representations of interdental papillae between each pair of adjacent ones of the plurality of preliminary segmentation loops 2202.

Figure 26:
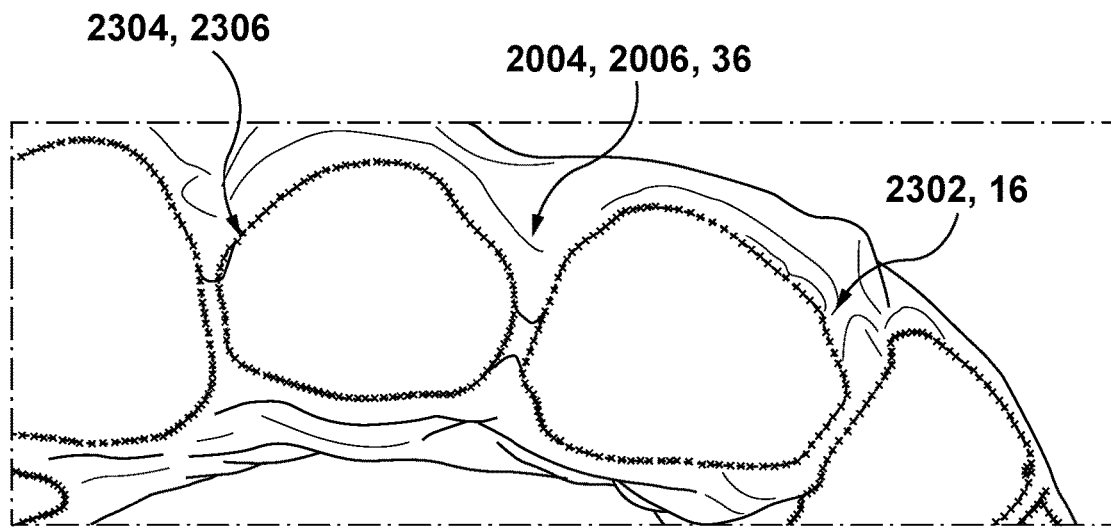

Further, the processor 550 may be configured to close each one of the plurality of preliminary segmentation loops 2202, thereby generating a plurality of closed preliminary segmentation loops 2302, as depicted in FIG. 26, in accordance with certain non-limiting embodiments of the present technology. To close each one of the plurality of preliminary segmentation loops 2202, the processor 550 may be configured to use, for example, linear segments extending between respective ends thereof. However, segments of various curvatures may be used for closing each one of the plurality of preliminary segmentation loops 2202 depending on a particular implementation of the present technology.

Additionally, in some non-limiting embodiments of the present technology, the processor 550 may be further configured to smooth each of the plurality of closed preliminary segmentation loops 2302 using one of the techniques described above in respect of smoothing the closed curve 1304.

Also, in some non-limiting embodiments of the present technology, the processor 550 may be configured to redefine certain mesh elements of the plurality of raw mesh elements 2004 respectively representative of each of the plurality of closed preliminary segmentation loops 2302 such that a plurality of loop vertices 2306 associated with a given closed preliminary segmentation loop 2304 are equally spaced. In some non-limiting embodiments of the present technology, the processor 550 may be further configured to maintain a predetermined number of vertices in the plurality of loop vertices 2306 (such as 90 vertices, for example), based, for example, on a trade-off between a quality of the comprehensive gingiva 3D representation 3100 and computational complexity and/or demand associated with the generation thereof.

Figure 27:
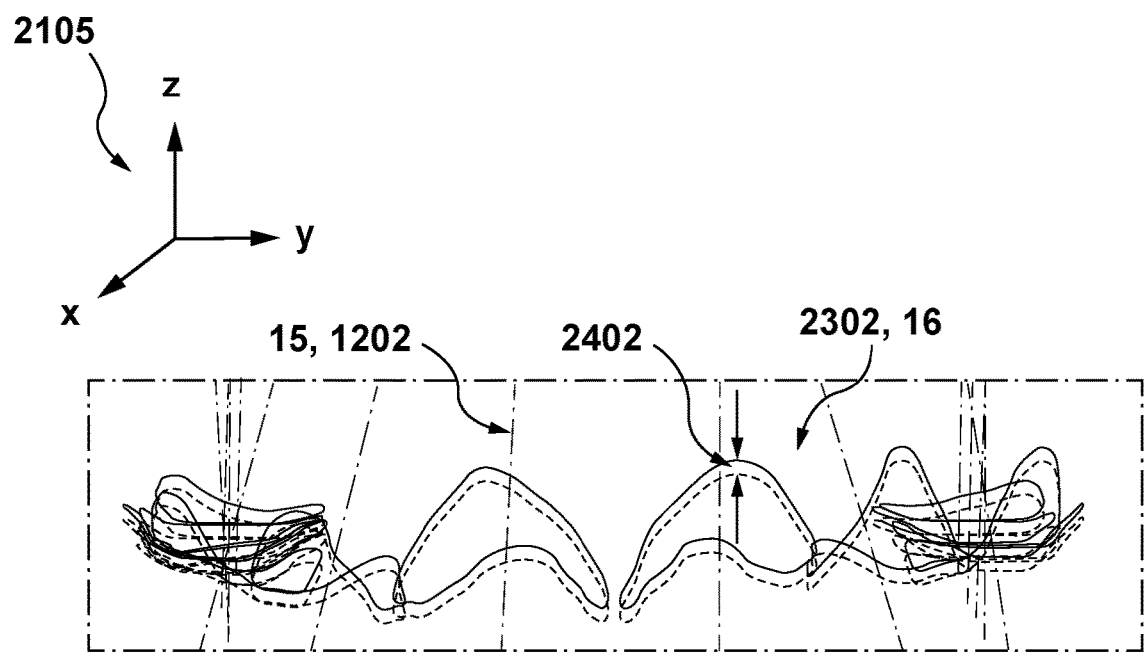

Further, with reference to FIG. 27, according to some non-limiting embodiments of the present technology, the processor 550 may be configured to translate each one of the plurality of closed preliminary segmentation loops 2302 along a respective longitudinal tooth axis (such as the longitudinal tooth axis 1202 associated with the tooth 15 described above with reference to FIG. 14) at a predetermined translation distance 2402. By so doing, the processor 550 may be configured to compensate for a possible chamfer effect produced by the imaging device 430 when generating the raw arch form 3D representation 2000. Thus, a given value of the predetermined translation distance 2402 may depend, inter alia, on a specific configuration of the imaging device 430, and in specific non-limiting embodiments of the present technology, may be, for example, 0.25 mm.

Figure 28:
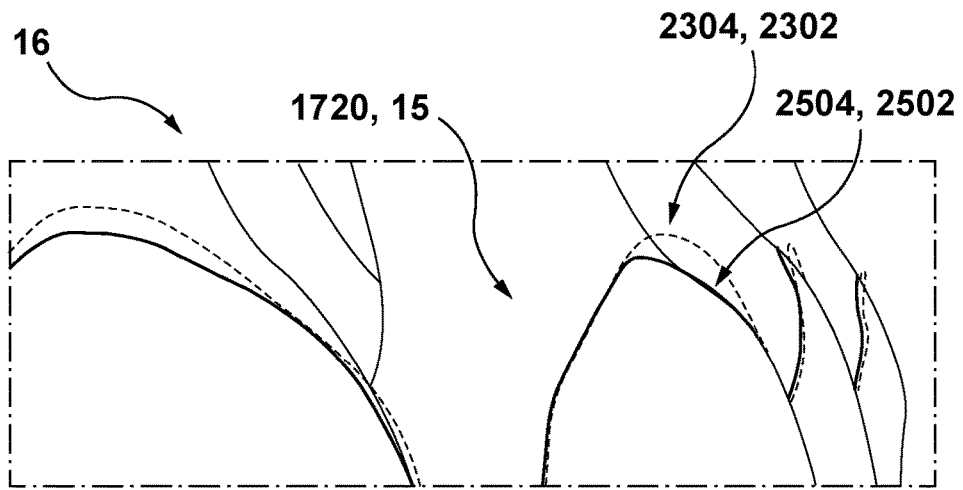

Finally, with reference to FIG. 28, according to some non-limiting embodiments of the present technology, the processor 550 may be configured to project each one of the plurality of closed preliminary segmentation loops 2302 onto a respective one of tooth 3D representations (such as the tooth 3D representation 1720 of the tooth 15 described above with reference to FIG. 19) of the upper teeth 16, thereby generating a plurality of segmentation loops 2502, which may further be used for generating the comprehensive gingiva 3D representation 3100 of the upper gingiva 36.

For example, the processor 550 may be configured to project the given closed preliminary segmentation loop 2304 onto the tooth 3D representation 1720 projecting each vertex (not separately numbered) representative thereof onto the tooth 3D representation 1720 along a respective shortest path thereto, thereby generating a given segmentation loop 2504 of the plurality of segmentation loops 2502.

According to certain non-limiting embodiments of the present technology, the processor 550 may further be configured to generate a central curve through the plurality of segmentation loops 2502.

The method 300 hence advances to step 306.

Figure 29:
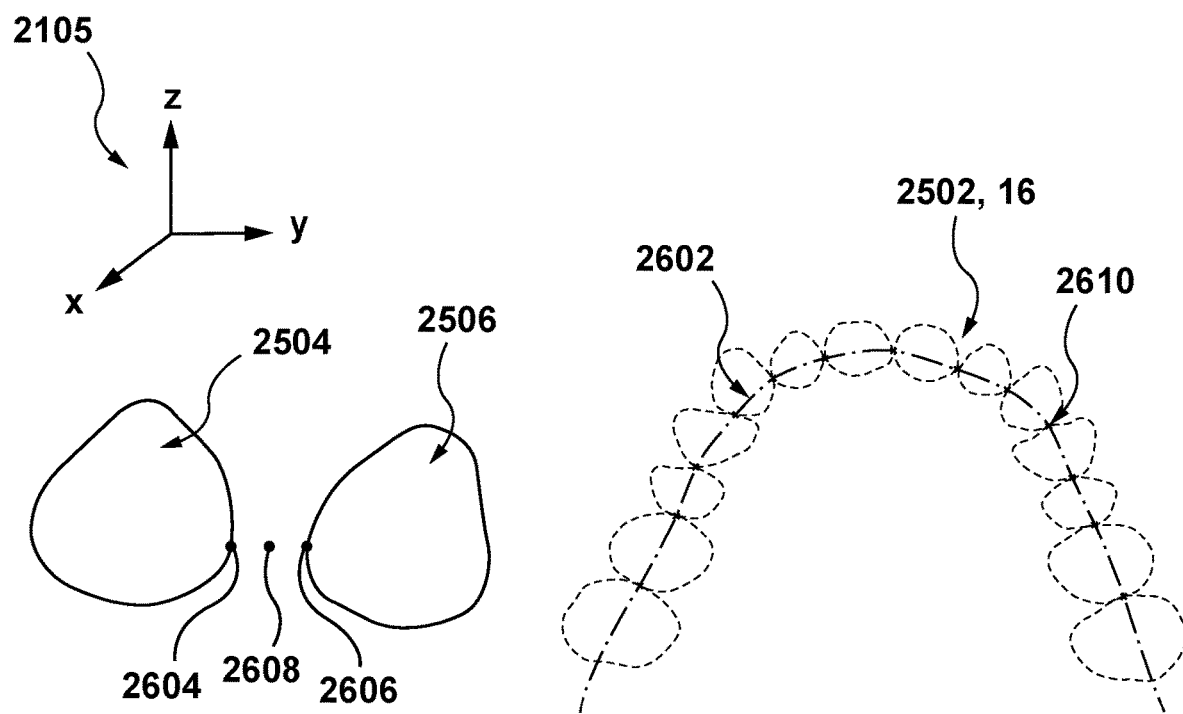
FIG. 29 depicts a schematic diagram of a step of the method of FIG. 22, executed by the processor of FIG. 5, for generating, based on the plurality of segmentation loops of FIG. 28, a primary central curve for generating the comprehensive gingiva 3D representation, in accordance with certain non-limiting embodiments of the present technology.

Step 306: Determining, Between Each Adjacent Two Segmentation Loops of the Plurality of Segmentation Loops, a Midpoint, Thereby Generating a Plurality of Primary Midpoints for the Plurality of Segmentation Loops;

With reference to FIG. 29, at step 306, by the processor 550 may be configured to identify points to generate a primary central curve 2602, in accordance with certain non-limiting embodiments of the present technology.

According to certain non-limiting embodiments of the present technology, the processor 550 may first be configured to identify, for each one of the plurality of segmentation loops 2502, a point thereof that is closest to an adjacent segmentation loop. For example, on the given segmentation loop 2504, the processor 550 may be configured to identify a first closest point 2604 that is closest to an adjacent segmentation loop 2506. By the same token, the processor 550 may be configured to identify, on the adjacent segmentation loop 2506, a second closest point 2606, which is closest to the given segmentation loop 2504 (in other words, to the first closest point 2604).

Further, based on the first closest point 2604 and the second closest point 2606, the processor 550 may be configured to determine a given primary midpoint 2608 of a plurality of primary midpoints 2610. In some non-limiting embodiments of the present technology, the processor 550 may be configured to determine the given primary midpoint 2608, for example, as a midpoint between the first closest point 2604 and the second closest point 2606 within the jaw coordinate system 2105.

The method 300 hence proceeds to step 308.

Step 308: Based on the Plurality of Midpoints, Generating a Primary Central Curve Along a First Horizontal Plane Parallel to the Transverse Plane;

At step 308, based on the plurality of primary midpoints 2610, the processor 550 may be configured to generate the primary central curve 2602. For example, the processor 550 may be configured to generate the primary central curve 2602 by joining each one of the plurality of primary midpoints 2610 by a respective curve segment (not separately depicted). In some non-limiting embodiments of the present technology, the respective curve segment may be a segment of a second order Bezier curve. However, it should be noted that how curvature of the respective curve segment may be defined is not limited, and in other non-limiting embodiments of the present technology, it may also be defined, for example, by a cubic Bezier curve.

Also, in those non-limiting embodiments of the present technology (not depicted) where certain of the upper teeth 16 are missing (previously extracted or destroyed, for example) forming respective blank spaces in the plurality of segmentation loops 2502, the processor 550 may further be configured to extrapolate the primary central curve 2602 within the respective blank spaces based on curvature thereof associated with those of the upper teeth 16 adjacent to the blank spaces. The same applies to those of the plurality of segmentation loops 2502 having no second adjacent segmentation loop, such as those representative of most distal ones of the upper teeth 16 within the upper arch form 20.

Further, according to certain non-limiting embodiments of the present technology, the processor 550 may be configured to join each pair of adjacent ones of the plurality of segmentation loops 2502 by respective arcs representative of interdental papillae of the comprehensive gingiva 3D representation.

Figure 30:
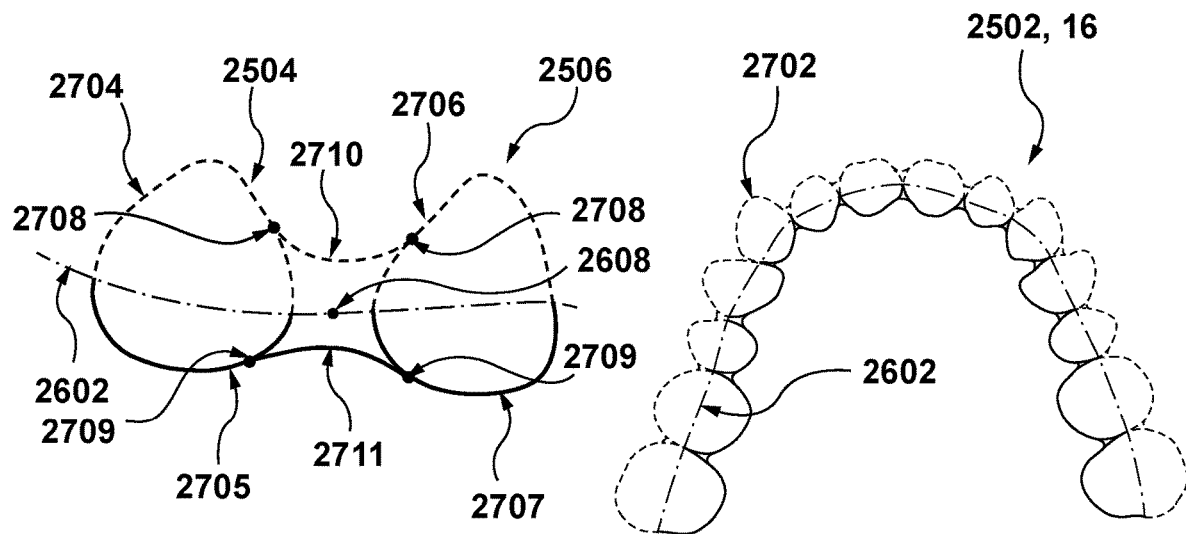
FIGS. 30 and 31 depict schematic diagrams of steps of the method of FIG. 22, executed by the processor of FIG. 5, for generating, based on the primary central curve of FIG. 29, a border curve of the comprehensive gingiva 3D representation associated with upper arch form of FIG. 2, in accordance with certain non-limiting embodiments of the present technology.

With reference to FIG. 30, there is depicted a schematic diagram of a primary border curve 2702 generated by the processor 550 based on joining adjacent ones of the plurality of segmentation loops 2502, in accordance with certain non-limiting embodiments of the present technology.

As it can be appreciated, the primary central curve 2602 divides each one of the given segmentation loop 2504 and the adjacent segmentation loop 2506 into a first outer portion 2704, a first inner portion 2705, a second outer portion 2706, and a second inner portion 2707, respectively. Further, according to some non-limiting embodiments of the present technology, the processor 550 may be configured to determine a respective length of each one of the first outer portion 2704, the first inner portion 2705, the second outer portion 2706, and the second inner portion 2707. Finally, based on the respective length, the processor 550 may further be configured to identify an outer pair of points 2708 and an inner pair of points 2709 to generate an outer arc 2710 and an inner arc 2711, thereby interconnecting the given segmentation loop 2504 with the adjacent segmentation loop 2506.

In some non-limiting embodiments of the present technology, the processor 550 may be configured to identify the outer pair of points 2708 and the inner pair of points 2709 based on predetermined coefficients applied to the respective length of each of the first outer portion 2704, the first inner portion 2705, the second outer portion 2706, and the second inner portion 2707. As such, each one of the outer pair of points 2708 and the inner pair of points 2709 may be located at a predetermined level of the respective length of one of the first outer portion 2704, the first inner portion 2705, the second outer portion 2706, and the second inner portion 2707.

For example, the processor 550 may be configured to identify a first one of the outer pair of points 2708, lying on the first outer portion 2704, and a first one of the inner pair of points 2709, lying on the first inner portion 2705, to be located at a 0.75 level of the respective length associated therewith. By the same token, the processor 550 may be configured to identify a second one of the outer pair of points 2708, lying on the second outer portion 2706, and a second one of the inner pair of points 2709, lying on the second inner portion 2707, to be located on a 0.25 level of the respective length associated therewith. It should be expressly understood that other predetermined coefficients may also be applied, in alternative non-limiting embodiments of the present technology, depending, inter alia, on a specific anatomical configuration (such as a type thereof) of an associated one of the upper teeth 16.

Having identified each one of the outer pair of points 2708 and the inner pair of points 2709, the processor 550 may further be configured to generate the outer arc 2710 and the inner arc 2711 based on curvature of the given segmentation loop 2504 and the adjacent segmentation loop 2506. For example, the processor 550 may be configured to generate one of the outer arc 2710 and the inner arc 2711 maintaining (in a sense, propagating) curvature of one of the given segmentation loop 2504 and the adjacent segmentation loop 2506. By doing so, the processor 550 may be configured to interconnect each pair of adjacent ones of the plurality of segmentation loops 2502 generating the primary border curve 2702.

According to certain non-limiting embodiments of the present technology, after generating the primary border curve 2702, the processor 550 may further be configured to generate, between each pair of adjacent ones of the plurality of segmentation loops 2502, a respective tween curve that may be used for joining gingiva segments (generation of which will be described below) of the comprehensive gingiva 3D representation 3100 with the primary border curve 2702.

Figure 31:
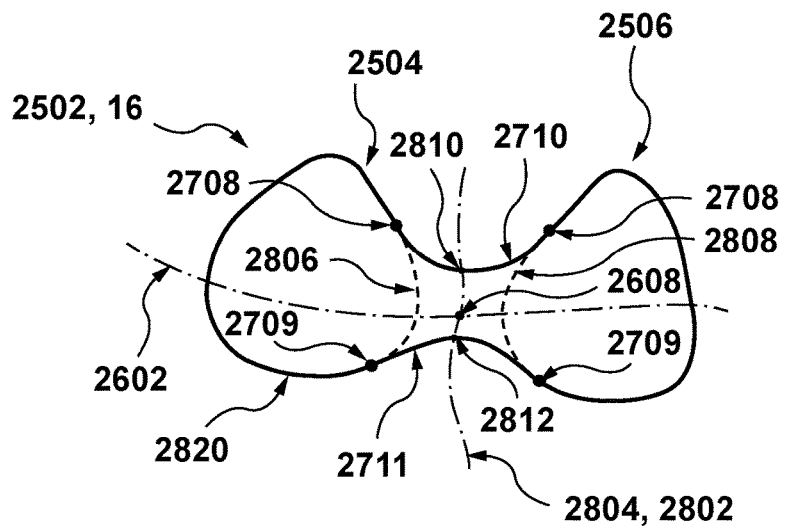
Figure 32A:
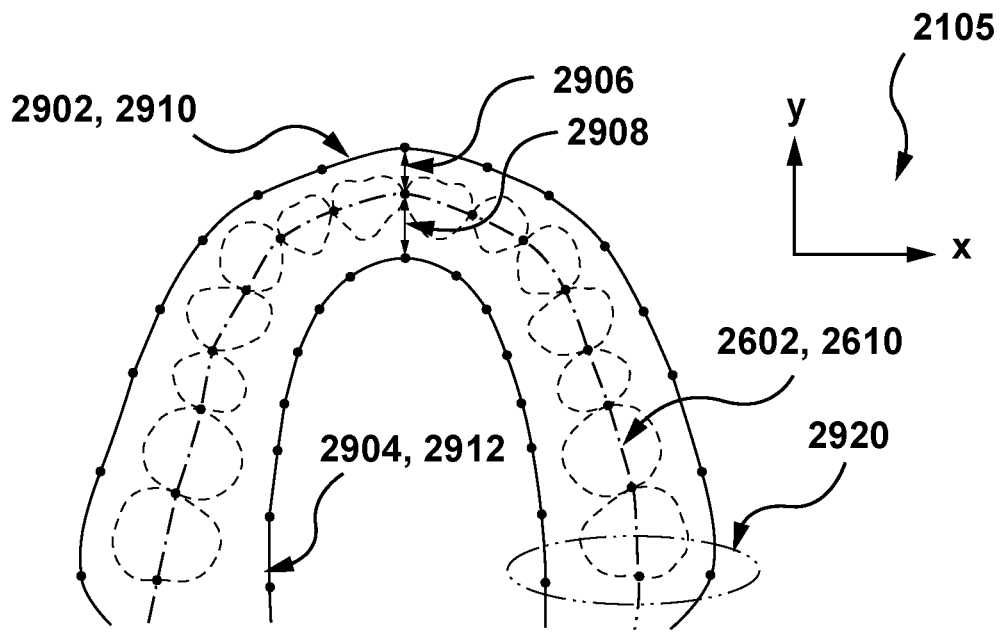
FIGS. 32A and 32B depict schematic diagrams of steps of the method of FIG. 22, executed by the processor of FIG. 5, for generating a first gingiva segment of the comprehensive gingiva 3D representation associated with upper arch form of FIG. 2, in accordance with certain non-limiting embodiments of the present technology.
Figure 32B:
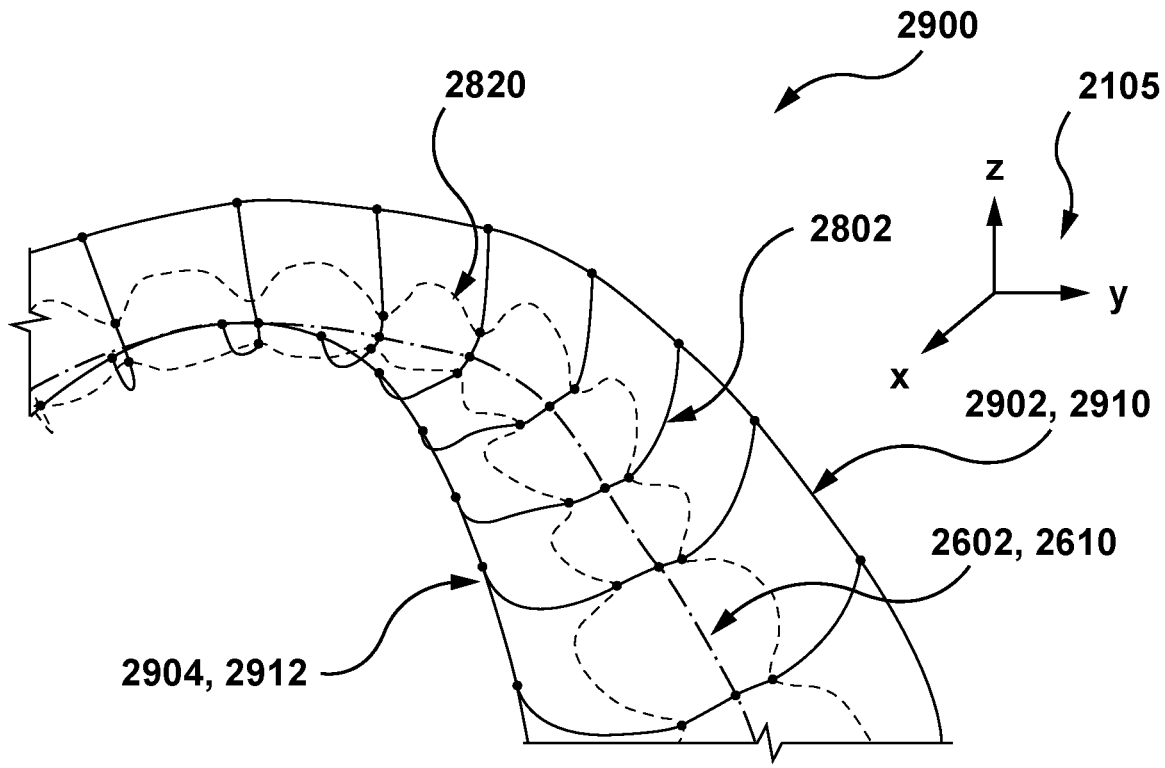

With reference to FIG. 31, there is depicted a schematic diagram of a step of a process for generating, by the processor 550, a given tween curve 2804 of a plurality of tween curves 2802, in accordance with certain non-limiting embodiments of the present technology.

According to certain non-limiting embodiments of the present technology, the processor 550 may be configured to generate the given tween curve 2804 to originate in the given primary midpoint 2608, based on the given segmentation loop 2504 and the adjacent segmentation loop 2506. For example, the processor 550 may be configured to generate the given tween curve 2804 based on a first loop segment 2806 and a second loop segment 2808 respectively defined on the given segmentation loop 2504 and the adjacent segmentation loop 2506 between respective ones of the outer pair of points 2708 and the inner pair of points 2709 lying thereon.

In some non-limiting embodiments of the present technology, the processor 550 may be configured to generate the given tween curve 2804 as an average curve of the first loop segment 2806 and the second loop segment 2808. To that end, according to these embodiments, the processor 550 may be configured to use one or more curve fitting techniques, which may include, without being limited to, one or more of: a linear curve fitting technique, a non-linear curve fitting technique, including, for example, a polynomial curve fitting technique, an exponential curve fitting technique, a logarithmic curve fitting technique, a spline curve fitting technique, and the like.

Additionally, in some non-limiting embodiments of the present technology, the processor 550 may be configured to adjust respective spatial positions of the outer arc 2710 and that of the inner arc 2711 such that they intersect with the given tween curve 2804, for example, in an outer intersection point 2810 and in an inner intersection point 2812. By doing so, the processor 550 may be configured to generate, based on the primary border curve 2702, a border curve 2820.

Having generated the plurality of tween curves 2802, the processor 550 may thus be configured to use it as a frame for generation of the gingiva segments based on the border curve 2820, thereby generating the comprehensive gingiva 3D representation 3100, as will be described immediately below.

According to certain non-limiting embodiments of the present technology, the generating a given gingiva segment may further comprise generating, the processor 550, a respective inner and outer mesh curves, and joining them with the border curve 2820 using the plurality of tween curves 2802.

The method 300 hence advances to step 310.

Step 310: Generating, Based on the Primary Central Curve, a First Inner Mesh Curve and a First Outer Mesh Curve, the First Inner Mesh Curve Positioned Along a Second Horizontal Plane and the First Outer Mesh Curve Positioned Along a Third Horizontal Plane, Both the Second Horizontal Plane and the Third Horizontal Plane being Parallel to the Transverse Plane and being Vertically Offset, Along the Common Vertical Axis, from the First Horizontal Plane With reference to FIGS. 32A and 32B, there is depicted a schematic diagram of executing, by the processor 550, step 310 of the method 300 to generate a first gingiva segment 2900, in accordance with certain non-limiting embodiments of the present technology.

First, the processor 550 may be configured to generate a first outer mesh curve 2902 and a first inner mesh curve 2904. In some non-limiting embodiments of the present technology, the processor 550 may be configured to generate the first outer mesh curve 2902 and the first inner mesh curve 2904 by projecting the primary central curve 2602 onto a first horizontal plane (not depicted) and a second horizontal plane (not depicted), respectively.

In some non-limiting embodiments of the present technology, the processor 550 may be configured to determine the first horizontal plane (not depicted) and the second horizontal plane (not depicted) to be parallel to the XY plane associated with the jaw coordinate system 2105 and vertically offset, along the Z axis, from the border curve 2820. For example, the processor 550 may be configured to determine: (1) the first horizontal plane (not depicted) to be vertically offset from a highest vertex of the border curve 2820 along the Z axis associated with the jaw coordinate system 2105 at a first predetermined vertical distance; and (2) the second horizontal plane (not depicted) to be vertically offset from the highest vertex of the border curve 2820 along the Z axis at a second predetermine vertical distance. Generally speaking, the first predetermined vertical distance and the second predetermined vertical distance have different values, which, in some non-limiting embodiments of the present technology may be, for example, 5 mm and 6 mm, respectively. In other non-limiting embodiments of the present technology, the first predetermined vertical distance and the second predetermined vertical distance may be equal, that is, the first horizontal plane (not depicted) and the second horizontal plane (not depicted) may comprise a same horizontal plane.

Further, having generated the first outer mesh curve 2902 and the first inner mesh curve 2904 in the first horizontal plane (not depicted) and the second horizontal plane (not depicted), respectively, the processor 550 may be configured to offset them horizontally therewithin relative to a horizontal projection of the primary central curve 2602 onto the XY plane associated with the jaw coordinate system 2105, that is, along the Y axis associated with the jaw coordinate system 2105. For example, the processor 550 may be configured to offset the first outer mesh curve 2902 along the Y axis anteriorly relative to the primary central curve 2602 at an anterior horizontal distance 2906. Further, the processor 550 may be configured to offset the first inner mesh curve 2904 along the Y axis posteriorly relative to the primary central curve 2602 at a posterior horizontal distance 2908. Broadly speaking, the anterior horizontal distance 2906 and the posterior horizontal distance 2908 may have different values, and in some non-limiting embodiments of the present technology, may vary within a distance value range from 10 mm to 12 mm, as an example. However, in other non-limiting embodiments of the present technology, the anterior horizontal distance 2906 and the posterior horizontal distance 2908 may be equal.

Additionally, the processor 550 may be configured to modulate each one of the first outer mesh curve 2902 and the first inner mesh curve 2904 adjusting respective curvature thereof accounting for specific anatomical features of the upper gingiva 36 of the subject.

According to certain non-limiting embodiments of the present technology, the processor 550 may further be configured to modulate a respective length of each one of the primary central curve 2602, the first outer mesh curve 2902, and the first inner mesh curve 2904. For example, the processor 550 may be configured to cut each one of the primary central curve 2602, the first outer mesh curve 2902, and the first inner mesh curve 2904 by a perpendicular plane (not separately depicted) parallel to an XZ plane associated with the jaw coordinate system 2105 and located at a predetermined horizontal distance anteriorly, along the Y axis, from a most posterior vertex of the raw gingiva 3D representation 2006 (depicted in FIG. 24). In some non-limiting embodiments of the present technology, this predetermined distance may be, however, not limited to, 2 mm.

The method further proceeds to step 312.

Step 312: Projecting the Plurality of Primary Midpoints onto the First Inner Mesh Curve and the First Outer Mesh Curve, Thereby Generating a First Plurality of Inner Midpoints and a First Plurality of Outer Midpoints At step 312, according to certain non-limiting embodiments of the present technology, based on the plurality of primary midpoints 2610, the processor 550 may be configured to generate a first plurality of outer midpoints 2910 and a first plurality of inner midpoints 2912 respectively associated with the first outer mesh curve 2902 and the first inner mesh curve 2904. To that end, in some non-limiting embodiments of the present technology, the processor 550 may be configured to project the plurality of primary midpoints 2610 onto each one of the first outer mesh curve 2902 and the first inner mesh curve 2904 maintaining same distribution of midpoints of the first plurality of outer midpoints 2910 and the first plurality of inner midpoints 2912 therewithin as that of the plurality of primary midpoints 2610 within the primary central curve 2602. For example, the processor 550 may be configured to calculate relative distances between each neighboring ones of the plurality of primary midpoints 2610, and based on a length of the primary central curve 2602, determine a respective weight coefficient for distributing midpoints of the first plurality of outer midpoints 2910 and the first plurality of inner midpoints 2912 within the first outer mesh curve 2902 and the first inner mesh curve 2904, respectively.

The method further proceeds to step 314.

Step 314: Generating a First Segment of the Reconstructed 3D Representation of the Gingiva by Joining Each One from the Plurality of Primary Midpoints with Respective Ones from the First Plurality of Inner Midpoints and from the First Plurality of Outer Midpoints At step 314, having generated the first plurality of outer midpoints 2910 and the first plurality of inner midpoints 2912, the processor 550 can be said to have generated a plurality of midpoint triplets 2920 including a respective one from the first plurality of outer midpoints 2910, a respective one from the plurality of primary midpoints 2610, and a respective one from the plurality of inner midpoints 2912. Accordingly, by interconnecting each one of the plurality of midpoint triplets 2920 using a respective one of the plurality of tween curves 2802, the processor 550 may be configured to generate the first gingiva segment 2900 of the comprehensive gingiva 3D representation of the upper gingiva 36.

Figure 33:
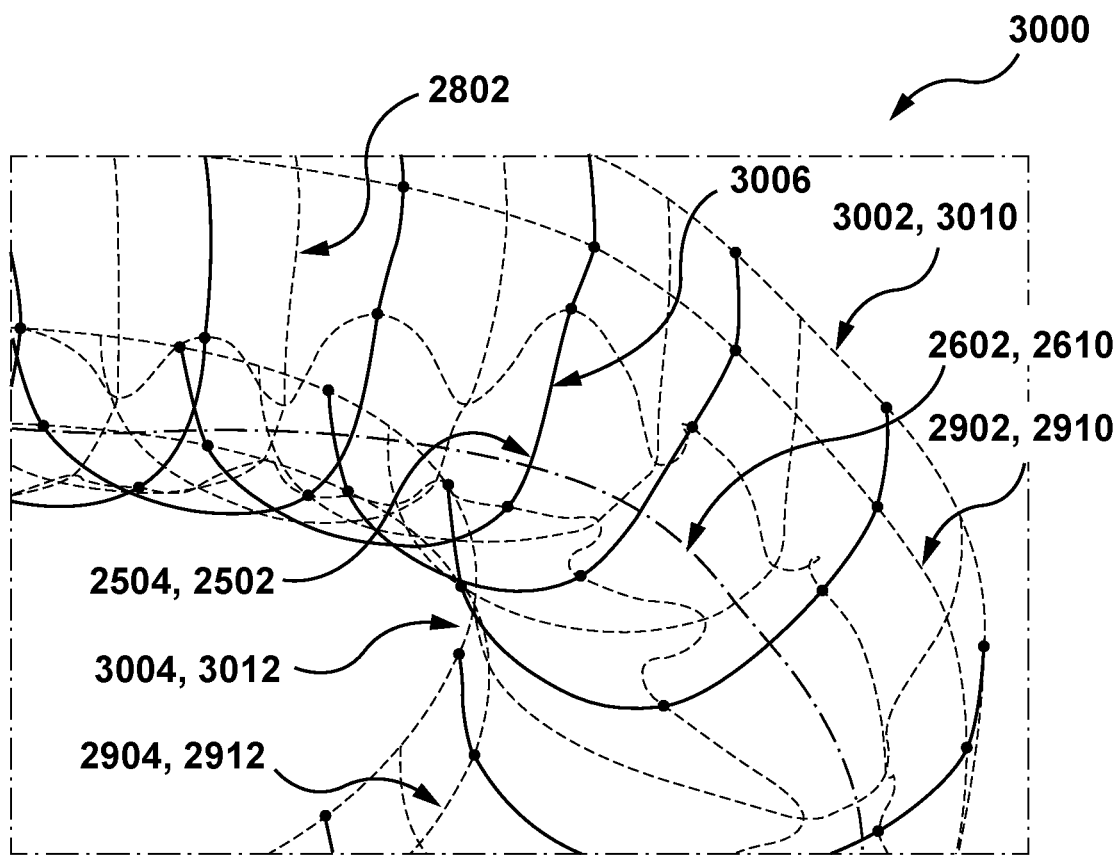
FIG. 33 depicts a schematic diagram of a step of the method of FIG. 22, executed by the processor of FIG. 5, for generating a second gingiva segment of the comprehensive gingiva 3D representation associated with upper arch form of FIG. 2 and additional granulation thereof, in accordance with certain non-limiting embodiments of the present technology.

With reference to FIG. 33, following the same approach described above in respect of generating the first gingiva segment 2900, the processor 550 may be configured to generate a second gingiva segment 3000 of the comprehensive gingiva 3D representation 3100, in accordance with certain non-limiting embodiments of the present technology. To that end, the processor 550 may be configured to generate a second outer mesh curve 3002 and a second inner mesh curve 3004 by projecting the primary central curve 2602 onto a third horizontal plane (not depicted) and a fourth horizontal plane (not depicted), respectively. The processor 550 may be configured to construct the third horizontal plane (not depicted) and the fourth horizontal plane (not depicted) to be parallel to and vertically offset from a respective one of the first horizontal plane (not depicted) and the second horizontal plane (not depicted) at a third predetermined vertical distance that, according to specific non-limiting embodiments of the present technology, may be 0.4 mm, as an example.

Further, the processor 550 may be configured to generate, based on the plurality of primary midpoints 2610, a second plurality of outer midpoints 3010 and a second plurality of inner midpoints 3012 respectively associated with the second outer mesh curve 3002 and the second inner mesh curve 3004 in a similar fashion described above in respect of the first plurality of outer midpoints 2910 and the first plurality of inner midpoints 2912, respectively.

Finally, extending each one of the plurality of tween curves 2802 through a respective one from the first plurality of outer midpoints 2910 and a respective one from the second plurality of outer midpoints 3010; and further through a respective one from the first plurality of inner midpoints 2912 and a respective one from the second plurality of inner midpoints 3012, the processor 550 may thus be configured to generate the second gingiva segment 3000.

In additional non-limiting embodiments of the present technology, the processor 550 may further be configured to generate a second plurality of tween curves 3006. To that end, to generate a given one of the second plurality of tween curves 3006, the processor 550 may be configured to generate, on the given segmentation loop 2504 of the plurality of segmentation loops 2502, an additional pair of points (not depicted). For example, the processor 550 may be configured to generate each one of the additional pair of points (not depicted) to correspond to a 0.5 level of the respective length of the first outer portion 2704 and the first inner portion 2705 (see FIG. 30) of the given segmentation loop 2504. Further, the processor 550 may be configured to generate the given one of the second plurality of tween curves 3006 extending though the additional pair of points (not depicted) on the given segmentation loop 2504 similar to the generating the given tween curve 2804 of the plurality of tween curves 2802.

Finally, the processor 550 may be configured to extend each one of the second plurality of tween curves 3006 through (1) the first outer mesh curve 2902 and the second outer mesh curve 3002; and (2) the first inner mesh curve 2904 and the second inner mesh curve 3004. This is believed to allow achieving a desired level of granularity of the comprehensive gingiva 3D representation 3100 of the upper gingiva 36.

It should be expressly understood that following the above approach to generating the second plurality of tween curves 3006, to achieve a desired level of granularity of the comprehensive gingiva 3D representation 3100, the processor 550 may be configured to generate additional pluralities of tween curves at respective levels of the associated lengths of the first outer portion 2704 and the first inner portion 2705 of the given segmentation loop 2504.

Accordingly, based on predetermined dimensions for the comprehensive gingiva 3D representation 3100 (that in turn may be indicative of an average gingiva height, for example), the processor 550 may be configured to generate additional, such as 3 or 4, gingiva segments following the approach described above in respect of generating the first gingiva segment 2900 and the second gingiva segment 3000. By so doing the processor 550 can be said to use a "scaffolding" technique of generating a respective gingiva segment, thereby generating a base gingiva cage 3102 of the comprehensive gingiva 3D representation 3100 as depicted in FIG. 34, in accordance with certain non-limiting embodiments of the present technology.

As it can be appreciated, the base gingiva cage 3102 is represented by a plurality of ordered quadrilateral mesh elements 3104 allowing the processor 550 to apply textures and colours thereto easier than to the plurality of raw mesh elements 2004 initially provided by the imaging device 430, which, in turn, may significantly save the computational resources of the computer system 410.

Also, in some non-limiting embodiments of the present technology, before the applying the textures and colours to the base gingiva cage 3102, thereby generating the comprehensive gingiva 3D representation 3100, the processor 550 may be configured to apply the Catmull-Clark subdivision surface algorithm to the plurality of ordered quadrilateral mesh elements 3104 to achieve the desired level of granularity and smoothness (such as that corresponding to one of the plurality of augmented crown mesh elements 1022 and plurality of augmented root mesh elements 1824) of a surface of the comprehensive gingiva 3D representation 3100.

The method 300 finally advances to step 316.

Step 316: Causing Display of the First Segment of the Reconstructed 3D Representation of the Gingiva.

Figure 35:
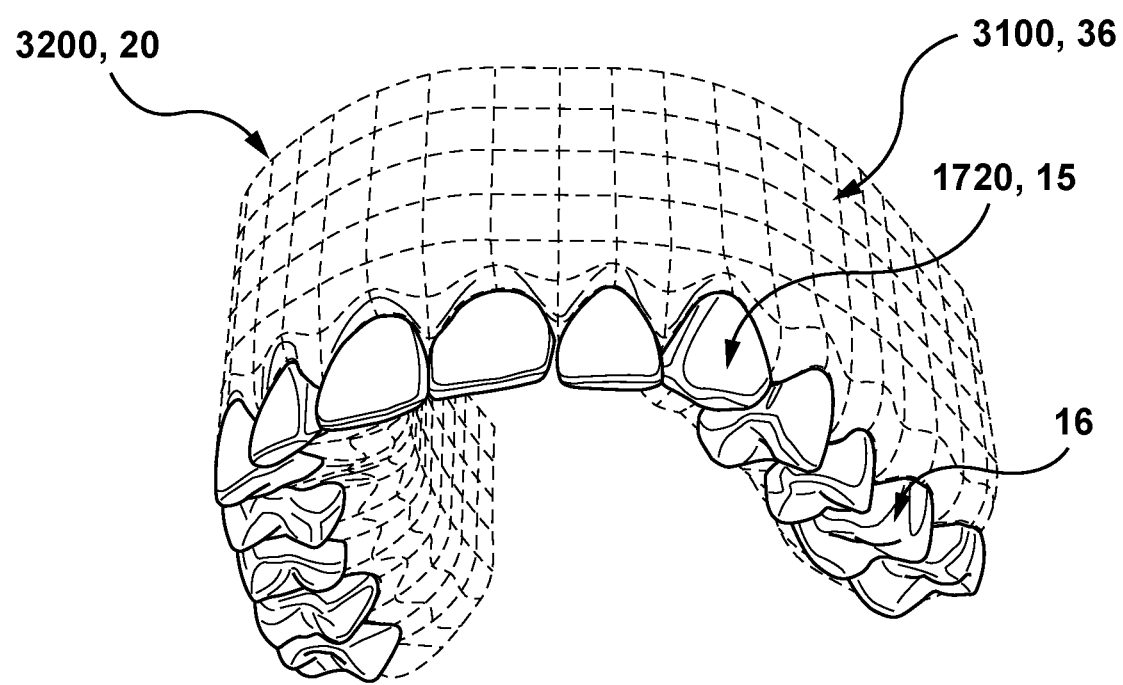
FIG. 35 depicts the comprehensive gingiva 3D representation of FIG. 34 merged with the tooth 3D representations of the plurality of teeth present in FIG. 1 generated, by the processor of FIG. 5, in accordance with the methods of FIGS. 8 and 13, forming a comprehensive 3D representation of the upper arch form of FIG. 2, in accordance with certain non-limiting embodiments of the present technology.

With reference to FIG. 35, according to certain non-limiting embodiments of the present technology, after texturizing the base gingiva cage 3102, thereby generating the comprehensive gingiva 3D representation 3100, at step 316, the processor 550 may further be configured to merge it with the tooth 3D representations (such as the tooth 3D representation 1720 or the augmented tooth 3D representation 1902 of the tooth 15 depicted in FIGS. 19 and 21, respectively, as an example) of the upper teeth 16. By doing so, the processor 550 may be configured to generate the comprehensive 3D representation 3200 of the upper arch form 20.

In additional non-limiting embodiments of the present technology, the processor 550 may further be configured to output the comprehensive 3D representation 3200 of the upper arch form 20 on the screen 422 of the computer system 410. Accordingly, a practitioner having access to the computer system 410 may thus be able to use the comprehensive 3D representation 3200 for modelling the tooth movements of the tooth 15 within the upper arch form 20 considering mutual spatial positions thereof with at least one of the adjacent teeth and effects of the modelled tooth movements, inter alia, onto the upper gingiva 36 ensuring the safer and more efficient orthodontic treatment plan.

Thus, certain embodiments of the method 300 allow for more efficient and accurate reconstruction of a 3D representation of the upper gingiva 36 (such as the comprehensive gingiva 3D representation 3100) based on raw image data indicative thereof and raw image data of the crown portions (such as the raw crown 3D representation 800 of the crown portion 26 of the tooth 15) of the upper teeth 16 provided by a conventional intraoral scanner, without the need for acquiring and further merging additional image data generated by methods of CT- and/or MR-imaging. Accordingly, such an approach allows for a more comprehensive modelling of the tooth movements of the tooth 15 in the course of the planned orthodontic treatment considering spatial positions of the root portion 28 thereof within the upper gingiva 36. In certain embodiments, this allows developing safer and more effective orthodontic treatments with limited computational resources and inaccessibility of additional image data.

Further, certain embodiments of the method 300 allow for more computationally efficient application of textures and colours to the comprehensive gingiva 3D representation 3100 for more effective visualization thereof on the screen 422 of the computer system 410 increasing accuracy of the planned orthodontic treatment.

Finally, certain embodiments of the method 300 allow for a more efficient production (for example, by means of 3D printing) of aligners (such as those made from composite materials), based on the comprehensive gingiva 3D representation 3100, for conducting the so determined orthodontic treatment, as expected overall dimensions thereof may allow more efficient planning of material consumption.

The method 300 hence terminates.

Needless to say that, in additional non-limiting embodiments of the present technology, the processor 550 may be configured to apply, mutatis mutandis, the methods 100, 200, and 300 for crown, root, and gingiva reconstruction, respectively, to generate a comprehensive 3D representation of the lower arch form 21 including that of the lower teeth 27 and the lower gingiva 37, as well as determine another orthodontic treatment based thereon, which is believed to be apparent to one skilled in the art.

It should further be noted that, in some non-limiting embodiments of the present technology, each of the method 100, the method 200, and the method 300 may be executed, by the processor 550, separately and/or independently based on respective input data. However, in other non-limiting embodiments of the present technology, each of these methods may be used in any combination therewith depending on a particular task at hand for reconstructing a respective anatomical structure associated with the subject.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A method for providing an augmented 3D representation of a given tooth of a patient, the method executable by a processor, the method comprising:
   acquiring a raw 3D representation of an arch form of the patient, the arch form comprising a gingiva and at least one tooth of the patient,
   the raw 3D representation comprising a defined portion forming part of a surface of the given tooth, and at least one undefined portion not forming part of the surface of the given tooth;
   the raw 3D representation comprising a 3D mesh having a plurality of vertices comprising:

constrained vertices associated with the defined portion, each constrained vertex having a constrained vertex normal vector;
unconstrained vertices initially associated with the undefined portion, each unconstrained vertex having an unconstrained vertex normal vector;
generating a set of confirmed constrained vertices, including the constrained vertices associated with the defined portion, for providing the augmented 3D representation of the given tooth by:
iteratively, for a given constrained vertex, identifying at least one associated unconstrained vertex which is adjacent to the given constrained vertex in the 3D mesh;
determining an angular difference between the constrained vertex normal vector of the given constrained vertex and the unconstrained vertex normal vector of the at least one associated unconstrained vertex;
in response to the angular difference being equal to or below a predetermined threshold value:
identifying the at least one associated unconstrained vertex to be a constrained vertex associated with the defined portion for inclusion in the set of confirmed constrained vertices;
in response to the angular difference being above the predetermined threshold value:
identifying the at least one associated unconstrained vertex to be an unconstrained vertex associated with the undefined portion for exclusion from the set of confirmed constrained vertices;
causing display of the augmented 3D representation of the given tooth based on the set of confirmed constrained vertices.

2. The method of claim 1, wherein the causing display of the augmented 3D representation comprises:
performing a smoothing operation on the set of confirmed constrained vertices to generate a smooth surface of the given tooth.

3. The method of claim 2, further comprising:
causing a filling of any gaps in the set of confirmed constrained vertices by the smoothing operation.

4. The method of claim 3, wherein the performing the smoothing operation comprises applying a Harmonic Function.

5. The method of claim 1, wherein the defined portion and the undefined portion are determined by applying an erosion function to the raw 3D representation.

6. The method of claim 5, wherein the defined portion is determined by:
determining, based on the erosion function, an edge of the given tooth based on the raw 3D representation of the given tooth; and
determining, based on the erosion function, a location of the defined portion by a predetermined distance, along a horizontal axis associated with the raw 3D representation of the given tooth, from at least one vertical edge of the raw 3D representation of the given tooth.

7. The method of claim 1, wherein the raw 3D representation is of a plurality of teeth of the patient including the given tooth, the method further comprising segmenting the raw 3D representation to separate the representation of the given tooth from other teeth of the plurality of teeth.

8. The method of claim 7, further comprising providing a respective augmented 3D representation for other teeth of the plurality of teeth of the patient.

9. The method of claim 1, further comprising generating an orthodontic treatment plan based on the augmented 3D representation of the given tooth.

10. The method of claim 1, wherein the raw 3D representation of the given tooth of the patient has a crown portion and a root portion, and the defined portion is based on one or more of the crown portion and the root portion.

11. A system for providing an augmented 3D representation of a given tooth of a patient, the system comprising a processor configured to execute a method, the method comprising:
acquiring a raw 3D representation of an arch form of the patient, the arch form comprising a gingiva and at least one tooth of the patient,
the raw 3D representation comprising a defined portion forming part of a surface of the given tooth, and at least one undefined portion not forming part of the surface of the given tooth;
the raw 3D representation comprising a 3D mesh having a plurality of vertices comprising:
constrained vertices associated with the defined portion, each constrained vertex having a constrained vertex normal vector;
unconstrained vertices initially associated with the undefined portion, each unconstrained vertex having an unconstrained vertex normal vector;
generating a set of confirmed constrained vertices, including the constrained vertices associated with the defined portion, for providing the augmented 3D representation of the given tooth by:
iteratively, for a given constrained vertex, identifying at least one associated unconstrained vertex which is adjacent to the given constrained vertex in the 3D mesh;
determining an angular difference between the constrained vertex normal vector of the given constrained vertex and the unconstrained vertex normal vector of the at least one associated unconstrained vertex;
in response to the angular difference being equal to or below a predetermined threshold value:
identifying the at least one associated unconstrained vertex to be a constrained vertex associated with the defined portion for inclusion in the set of confirmed constrained vertices;
in response to the angular difference being above the predetermined threshold value:
identifying the at least one associated unconstrained vertex to be an unconstrained vertex associated with the undefined portion for exclusion from the set of confirmed constrained vertices;
causing display of the augmented 3D representation of the given tooth based on the set of confirmed constrained vertices.

12. The system of claim 11, wherein the causing display of the augmented 3D representation comprises:
performing a smoothing operation on the set of confirmed constrained vertices to generate a smooth surface of the given tooth.

13. The system of claim 12, wherein the method further comprises:
causing a filling of any gaps in the set of confirmed constrained vertices by the smoothing operation.

14. The system of claim 13, wherein the performing the smoothing operation comprises applying a Harmonic Function.

15. The system of claim 11, wherein the defined portion and the undefined portion are determined by applying an erosion function to the raw 3D representation.

16. The system of claim 15, wherein the defined portion is determined by:
- determining, based on the erosion function, an edge of the given tooth based on the raw 3D representation of the given tooth; and
- determining, based on the erosion function, a location of the defined portion by a predetermined distance, along a horizontal axis associated with the raw 3D representation of the given tooth, from at least one vertical edge of the raw 3D representation of the given tooth.

17. The system of claim 11, wherein the raw 3D representation is of a plurality of teeth of the patient including the given tooth, the method further comprising segmenting the raw 3D representation to separate the representation of the given tooth from other teeth of the plurality of teeth.

18. The system of claim 17, wherein the processor is further configured to provide a respective augmented 3D representation for other teeth of the plurality of teeth of the patient.

19. The system of claim 11, wherein the processor is further configured to generate an orthodontic treatment plan based on the augmented 3D representation of the given tooth.

* * * * *